United States Patent
Henmi et al.

(10) Patent No.: US 6,291,399 B1
(45) Date of Patent: Sep. 18, 2001

(54) AGENT FOR CONTROLLING DISEASES AND INSECT PESTS, CONTAINING ALKOXYIMINO-SUBSTITUTED BICYCLIC DERIVATIVE AS ACTIVE INGREDIENT

(75) Inventors: Shinya Henmi; Seiji Kakinuma; Satomi Katoh; Yuriko Shiihashi, all of Tokorozawa (JP)

(73) Assignee: Agro-Kanesho Co., Ltd., Tokyo (JP)

( * ) Notice: Subject to any disclaimer, the term of this patent is extended or adjusted under 35 U.S.C. 154(b) by 0 days.

(21) Appl. No.: 09/482,922

(22) Filed: Jan. 14, 2000

Related U.S. Application Data

(63) Continuation of application No. PCT/JP98/03145, filed on Jul. 14, 1998.

(30) Foreign Application Priority Data

Jul. 15, 1997 (JP) .................................................. 9-190171

(51) Int. Cl.[7] .................................................. A01N 43/42
(52) U.S. Cl. ........................ 504/291; 504/292; 504/294; 549/404; 549/467
(58) Field of Search .................... 549/404, 467; 514/450, 456, 465; 504/291, 292, 294

(56) References Cited

FOREIGN PATENT DOCUMENTS

| | | |
|---|---|---|
| WO97/32842 | 9/1997 | (EP) . |
| 6-239812 | 8/1994 | (JP) . |
| WO98/09956 | 3/1998 | (JP) . |
| WO 98/17632 | 4/1998 | (JP) . |

OTHER PUBLICATIONS

Adams, JL 'Preparation of N–substituted tetrahydronaphthy–N–hydroxyureas and analogs as 5–lipoxygenase inhibitors' CA 116:255341, 1992.*

Koyama, Kunko, et al, Heterocycles, "Synthesis of Alkaloids, Cleistopholine, Oxylopine (Isoursuline), and Ursuline", vol. 29, No. 9, Sep. 1, 1989, HTCYAM ISSN 0385–5414, pp. 1649–1654.

* cited by examiner

*Primary Examiner*—Amelia Owens
(74) *Attorney, Agent, or Firm*—Oblon, Spivak, McClelland, Maier & Neustadt, P.C.

(57) ABSTRACT

Alkoxyimino-substituted bicyclic derivatives or salts thereof having an excellent effect of controlling diseases and insect pests are disclosed. These derivatives are represented by the following formula (I):

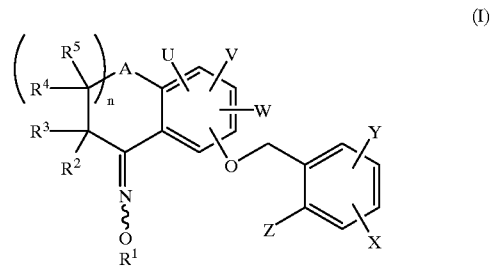

(I)

wherein $R^1$ represents, for example, a hydrogen atom, a C1–C6 alkyl group, a halogenated C1–C6 alkyl group, a C3–C5 alkenyl group, a halogenated C3–C5 alkenyl group, a C3–C5 alkynyl group or a halogenated C3–C5 alkynyl group, $R^2$, $R^3$, $R^4$ and $R^5$ independently represent, for example, a hydrogen atom, a C1–C3 alkyl group or a halogenated C1–C3 alkyl group, A represents, for example, an oxygen atom, n represents 0, 1 or 2, X and Y independently represent, for example, a hydrogen atom, a halogen atom or a C1–C3 alkyl group, Z represents $C(CO_2CH_3)=CHR^8$, $C(CO_2CH_3)=NOCH_3$, $C(CONHCH_3)=NOCH_3$, $C(CSNHCH_3)=NOCH_3$, $N(CO_2CH_3)OCH_3$, $N(CONHCH_3)OCH_3$ ($R^8$ represents, for example, a hydrogen atom, a methyl group, an ethyl group or a methoxy group), and U, V and W independently represent a hydrogen atom, a halogen atom, a C1–C6 alkyl group, a cyano group or a nitro group.

40 Claims, No Drawings

AGENT FOR CONTROLLING DISEASES AND INSECT PESTS, CONTAINING ALKOXYIMINO-SUBSTITUTED BICYCLIC DERIVATIVE AS ACTIVE INGREDIENT

This application is a continuation of PCT/JP98/03145/ filed Jul. 14, 1998.

BACKGROUND OF THE INVENTION

1. Field of the Invention

The present invention relates to alkoxyimino-substituted bicyclic derivatives, a process for producing them, agents for controlling diseases and insect pests containing them as an active ingredient, and intermediates of them.

2. Description of the Background

Various compounds usable as agricultural fungicides have been known hitherto. For example, Japanese Patent Unexamined Published Application (hereinafter referred to as "J. P. KOKAI") No. Hei 4-182461 discloses agricultural fungicides containing alkoxyiminoacetamide compounds as active ingredients. The specific compounds stated in this patent specification include, for example, 2-methoxyimino-2-[2-(indane-5-yloxymethyl)-phenyl]-acetic acid methylamide (compound No. 20).

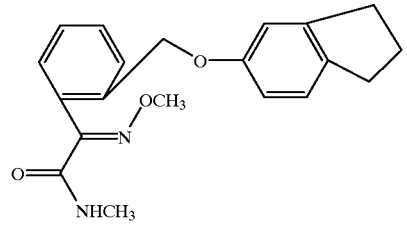

J. P. KOKAI No. Hei 3-17052 discloses 2-methoxyimino-2-[2-(5,6,7,8-tetrahydronaphthalene-2-yloxymethyl)phenyl]-methylacetate (compound No. 1.246) as a specific example of the compounds:

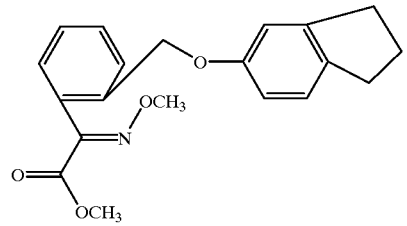

J. P. KOKAI No. Sho 63-216848 discloses propene derivatives usable for fungicide compositions. Specifically, methyl 3-methoxy-2-[2-(dibenzofuran-2-yloxymethyl)-phenyl]-acrylate (compound No. 189) is given in this patent specification.

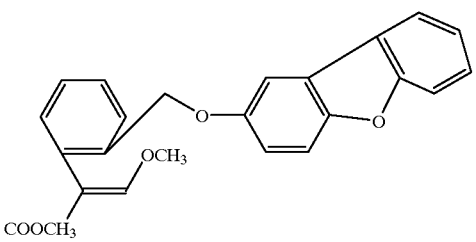

It is known that these compounds are effective in controlling diseases (the effects of controlling insect pests are not described in those specifications). However, the derivatives described therein are utterly different from those of the present invention in that they do not have an alkoxyimino substituent in the polycyclic part thereof. Further, these compounds have no or substantially no penetration and translocation. Under these circumstances, it is demanded to provide an agent for controlling diseases, which has an excellent penetration and translocation.

SUMMARY OF THE INVENTION

The object of the present invention is to provide alkoxyimino-substituted bicyclic derivatives having an effect of controlling diseases or insect pests and also an excellent penetration and translocation.

DETAILED DESCRIPTION OF THE PREFERRED EMBODIMENTS

After intensive investigations on agents for controlling diseases, which have an excellent penetration and translocation, the inventors have found that alkoxyimino-substituted bicyclic derivatives having a specific structure have a high penetration and translocation into plants and an excellent effect of controlling diseases and insect pests. The present invention has been completed on the basis of this finding.

DISCLOSURE OF THE INVENTION

The present invention is as follows:

1. An alkoxyimino-substituted bicyclic derivative having the following formula (I) or salt thereof:

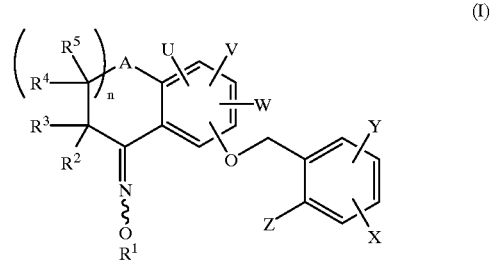

wherein $R^1$ represents a hydrogen atom, a C1–C6 alkyl group, a halogenlated C1–C6 alkyl group, a C3–C5 alkenyl group, a halogenated C3–C5 alkenyl group, a C3–C5 alkynyl group, a halogenated C3–C5 alkynyl group, a cyano-C1–C6 alkyl group, a C1–C4 alkoxy-C1–C6 alkyl group, a C1–C4 alkylcarbonyl-C1–C6 alkyl group, a C1–C4 alkoxycarbonyl-C1–C6 alkyl group, a C3–C6 cycloalkyl group, a C3–C6 cycloalkyl-C1–C6 alkyl group, a phenyl-C1–C6 alkyl group, or a naphthyl-C1–C6 alkyl group, $R^2$, $R^3$, $R^4$ and $R^5$ independently represent a hydrogen atom, a C1–C3 alkyl group or a halogenated C1–C3 alkyl group, A represents an oxygen atom, a sulfur atom or $C(R^6)R^7$, $R^6$ and $R^7$ independently represent a hydrogen atom, a C1–C3 alkyl group or a halogenated C1–C3 alkyl group, n represents 0, 1 or 2, U, V and W independently represent a hydrogen atom, a halogen atom, a C1–C6 alkyl group, a halogenated C1–C6 alkyl group, a C1–C6 alkoxy group, a halogenated C1–C6 alkoxy group, a cyano group or a nitro group, X and Y independently represent a hydrogen atom, a halogen atom, a C1–C3 alkyl group, a halogenated C1–C3 alkyl group, a C1–C3 alkoxy group, a halogenated C1–C3 alkoxy group, a cyano group or a nitro group, Z represents $C(CO_2CH_3)=CHR^8$, $C(CO_2CH_3)=NOCH_3$, $C(CONHCH_3)=NOCH_3$, $C(CSNHCH_3)=NOCH_3$, $N(CO_2CH_3)OCH_3$, $N(CONHCH_3)OCH_3$, $N(CSNHCH_3)OCH_3$, $CH(CO_2CH_3)OCH_3$, $CH(CONHCH_3)OCH_3$ or $CH(CSNHCH_3)OCH_3$, and $R^8$ represents a hydrogen atom, a methyl group, an ethyl group or a methoxyl group.

2. A process for producing an alkoxyimino-substituted bicyclic derivative having the formula (I) set forth in above item 1, which comprises reacting a phenol having the formula (II):

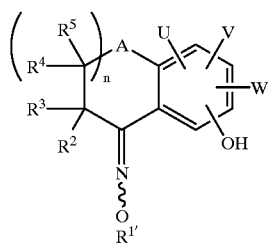

(II)

wherein $R^{1'}$ represents a C1–C6 alkyl group, a halogenated C1–C6 alkyl group, a C3–C5 alkenyl group, a halogenated C3–C5 alkenyl group, a C3–C5 alkynyl group, a halogenated C3–C5 alkynyl group, a cyano-C1–C6 alkyl group, a C1–C4 alkoxy-C1–C6 alkyl group, a C1–C4 alkylcarbonyl-C1–C6 alkyl group, a C1–C4 alkoxycarbonyl-C1–C6 alkyl group, a C3–C6 cycloalkyl group, a C3–C6 cycloalkyl-C1–C6 alkyl group, a phenyl-C1–C6 alkyl group, or a naphthyl-C1–C6-alkyl group, $R^2$, $R^3$, $R^4$ and $R^5$ independently represent a hydrogen atom, a C1–C3 alkyl group or a halogenated C1–C3-alkyl group, A represents an oxygen atom, a sulfur atom or $C(R^6)R^7$, $R^6$ and $R^7$ independently represent a hydrogen atom, a C1–C3 alkyl group or a halogenated C1–C3 alkyl group, n represents 0, 1 or 2, and U, V and W independently represent a hydrogen atom, a halogen atom, a C1–C6 alkyl group, a halogenated C1–C6 alkyl group, a C1–C6 alkoxy group, a halogenated C1–C6 alkoxy group, a cyano group or a nitro group, with a phenyl compound having the formula (III):

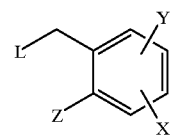

(III)

wherein

X and Y independently represent a hydrogen atom, a halogen atom, a C1–C3 alkyl group, a halogenated C1–C3 alkyl group, a C1–C3 alkoxy group, a halogenated C1–C3 alkoxy group, a cyano group or a nitro group, L represents a leaving group, Z represents $C(CO_2CH_3)=CHR^8$, $C(CO_2CH_3)=NOCH_3$, $C(CONHCH_3)=NOCH_3$, $C(CSNHCH_3)=NOCH_3$, $N(CO_2CH_3)OCH_3$, $N(CONHCH_3)OCH_3$, $N(CSNHCH_3)OCH_3$, $CH(CO_2CH_3)OCH_3$, $CH(CONHCH_3)OCH_3$ or $CH(CSNHCH_3)OCH_3$, and $R^8$ represents a hydrogen atom, a methyl group, an ethyl group or a methoxy group.

3. A process for producing an alkoxyimino-substituted bicyclic derivative having the formula (I) set forth in above item 1, which comprises reacting a substituted bicyclic compound having the formula (IV):

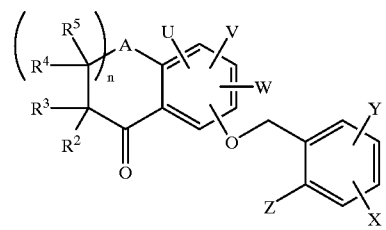

(IV)

wherein $R^2$, $R^3$, $R^4$ and $R^5$ independently represent a hydrogen atom, a C1–C3 alkyl group or a halogenated C1–C3 alkyl group, A represents an oxygen atom, a sulfur atom or $C(R^6)R^7$, $R^6$ and $R^7$ independently represent a hydrogen atom, a C1–C3 alkyl group or a halogenated C1–C3 alkyl group, n represents 0, 1 or 2, U, V and W independently represent a hydrogen atom, a halogen atom, a C1–C6 alkyl group, a halogenated C1–C6 alkyl group, a C1–C6 alkoxy group, a halogenated C1–C6 alkoxy group, a cyano group or a nitro group, X and Y independently represent a hydrogen atom, a halogen atom, a C1–C3 alkyl group, a halogenated C1–C3 alkyl group, a C1–C3 alkoxy group, a halogenated C1–C3 alkoxy group, a cyano group or a nitro group, Z represents $C(CO_2CH_3)=CHR^8$, $C(CO_2CH_3)=NOCH_3$, $C(CONHCH_3)=NOCH_3$, $C(CSNHCH_3)=NOCH_3$, $N(CO_2CH_3)OCH_3$, $N(CONHCH_3)OCH_3$, $N(CSNHCH_3)OCH_3$, $CH(CO_2CH_3)OCH_3$, $CH(CONHCH_3)OCH_3$ or $CH(CSNHCH_3)OCH_3$, and R[8] represents a hydrogen atom, a methyl group, an ethyl group or a methoxy group, with an amine having the formula (V) or a salt thereof:

  (V)

wherein R[1] represents a hydrogen atom, a C1–C6 alkyl group, a halogenated C1–C6 alkyl group, a C3–C5 alkenyl group, a halogenated C3–C5 alkenyl group, a C3–C5 alkynyl group, a halogenated C3–C5 alkynyl group, a cyano-C1–C6 alkyl group, a C1–C4 alkoxy-C1–C6 alkyl group, a C1–C4 alkylcarbonyl-C1–C6 alkyl group, a C1–C4 alkoxycarbonyl-C1–C6 alkyl group, a C3–C6 cycloalkyl group, a C3–C6 cycloalkyl-C1–C6 alkyl group, a phenyl-C1–C6 alkyl group, or a naphthyl-C1–C6 alkyl group.

4. An agent for controlling a disease or an insect pest, comprising the alkoxyimino-substituted bicyclic derivative or salt thereof set forth in above item 1 as an active ingredient.

5. An intermediate having the following formula (II):

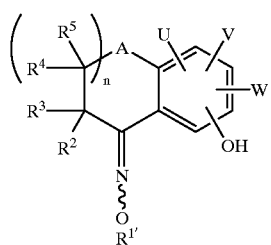  (II)

wherein

R[1] represents a C1–C6 alkyl group, a halogenated C1–C6 alkyl group, a C3–C5 alkenyl group, a halogenated C3–C5 alkenyl group, a C3–C5 alkynyl group, a halogenated C3–C5 alkynyl group, a cyano-C1–C6 alkyl group, a C1–C4 alkoxy-C1–C6 alkyl group, a C1–C4 alkylcarbonyl-C1–C6 alkyl group, a C1–C4 alkoxycarbonyl-C1–C6 alkyl group, a C3–C6 cycloalkyl group, a C3–C6 cycloalkyl-C1–C6 alkyl group, a phenyl-C1–C6 alkyl group, or a naphthyl-C1–C6 alkyl group, R[2], R[3], R[4] and R[5] independently represent a hydrogen atom, a C1–C3 alkyl group or a halogenated C1–C3 alkyl group, A represents an oxygen atom, a sulfur atom or $C(R^6)R^7$, R[6] and R[7] independently represent a hydrogen atom, a C1–C3 alkyl group or a halogenated C1–C3 alkyl group, and U, V and W independently represent a hydrogen atom, a halogen atom, a C1–C6 alkyl group, a halogenated C1–C6 alkyl group, a C1–C6 alkoxy group, a halogenated C1–C6 alkoxy group, a cyano group or a nitro group, and n represents 0, 1 or 2 provided that, when n is 0, U, V and W are not a C1–C6 alkoxy group or a halogenated C1–C6 alkoxy group.

6. An intermediate having the following formula (IV):

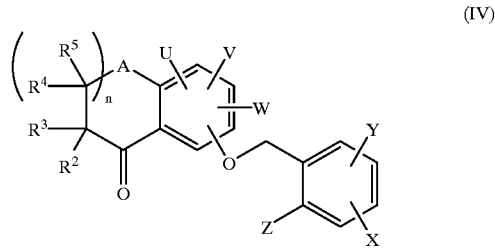  (IV)

wherein

R[2], R[3], R[4] and R[5] independently represent a hydrogen atom, a C1–C3 alkyl group or a halogenated C1–C3 alkyl group, A represents an oxygen atom, a sulfur atom or $C(R^6)R^7$, R[6] and R[7] independently represent a hydrogen atom, a C1–C3 alkyl group or a halogenated C1–C3 alkyl group, n represents 0, 1 or 2, U, V and W independently represent a hydrogen atom, a halogen atom, a C1–C6 alkyl group, a halogenated C1–C6 alkyl group, a C1–C6 alkoxy group, a halogenated C1–C6 alkoxy group, a cyano group or a nitro group, X and Y independently represent a hydrogen atom, a halogen atom, a C1–C3 alkyl group, a halogenated C1–C3 alkyl group, a C1–C3 alkoxy group, a halogenated C1–C3 alkoxy group, a cyano group or a nitro group, Z represents $C(CO_2CH_3)$=$CHR^8$, $C(CO_2CH_3)$=$NOCH_3$, $C(CONHCH_3)$=$NOCH_3$, $C(CSNHCH_3)$=$NOCH_3$, $N(CO_2CH_3)OCH_3$, $N(CONHCH_3)OCH_3$, $N(CSNHCH_3)OCH_3$, $CH(CO_2CH_3)OCH_3$, $CH(CONHCH_3)OCH_3$ or $CH(CSNHCH_3)OCH_3$, and R[8] represents a hydrogen atom, a methyl group, an ethyl group or a methoxy group.

MODE FOR CARRYING OUT THE INVENTION

The detailed description will be made on the present invention.

For R[1], the C1–C6, preferably C1–C4 alkyl groups include straight or branched alkyl groups such as methyl, ethyl, isopropyl, propyl, n-butyl, isobutyl, s-butyl, n-pentyl, isopentyl and n-hexyl groups.

The halogen atoms in the halogenated C1–C6, preferably C1–C4 alkyl groups include fluorine, chlorine and bromine atoms. Therefore, the halogenated C1–C6 alkyl groups include trifluoromethyl, difluoromethyl, 2-trifluoroethyl, 2-chloroethyl and 2-(4,5-dichloro)hexyl groups.

The C3–C5 alkenyl groups may be either straight or branched. They include allyl, 2-butenyl and 1-methyl-2-propenyl groups. The range of the halogen atoms in the halogenated C3–C5 alkenyl groups is the same as that described above.

The C3–C5 alkynyl groups may be either straight or branched. They include propargyl and 2-butynyl groups. The range of the halogen atoms in the halogenated C3–C5 alkynyl groups is the same as that described above.

The cyano-C1–C6 alkyl groups include cyanomethyl, 2-cyanoethyl and 2-(1-cyano)propyl groups. The C1–C4 alkoxy-C1–C6 alkyl groups include methoxymethyl, 1-ethoxyethyl, dimethoxymethyl and 2,2-diethoxyethyl groups. The C1–C4 alkylcarbonyl-C1–C6 alkyl groups include methylcarbonylmethyl, 1-ethylcarbonylethyl and isopropylcarbonylmethyl group. The C1–C4 alkoxycarbonyl-C1–C6 alkyl groups include methoxycarbonylmethyl, ethoxycarbonylmethyl and 2-ethoxycarbonylethyl groups. The C3–C6 cycloalkyl groups include cyclopropyl and cyclohexyl groups. The C3–C6 cycloalkyl-C1–C6 alkyl groups include cyclopropylmethyl and cyclohexylmethyl groups. The phenyl-C1–C6 alkyl groups (the phenyl group may have at least one of halogens, a cyano, a C1–C4 alkoxy groups and a halogenated C1–C4 alkoxy groups) include benzyl, 3,4-dichlorobenzyl, 4-methoxybenzyl and 4-trifluoromethoxybenzyl groups. The naphthyl-C1–C6 alkyl groups (the naphthyl group may have at least one of halogens, a cyano, a C1–C4 alkoxy groups and a halogenated C1–C4 alkoxy groups) include (1-naphthyl)methyl and (5-chloronaphthyl-2-yl)methyl group.

For $R^2$, $R^3$, $R^4$ and $R^5$, the ranges of the C1–C6 alkyl groups and the halogenated alkyl groups thereof are the same as those described above.

A represents an oxygen atom, a sulfur atom or $C(R^6)R^7$ wherein the ranges of $R^6$ and $R^7$ are the same as those of $R^2$, $R^3$, $R^4$ and $R^5$. Preferably, A is an oxygen atom.

n is 0, 1 or 2. When n is 0, the ring structure containing the part in parentheses in the formula (I) is a five-membered ring; and when n is 1, the ring structure containing the part in parentheses in the formula (I) is a six-membered ring.

For X and Y, the ranges of the halogen atoms, C1–C3 alkyl groups and halogenated alkyl groups thereof are the same as those described above. The C1–C3 alkoxy groups or the alkoxy groups in the halogenated alkoxy groups are those having 1 to 3 carbon atom. The C1–C3 alkyl groups in these groups include methyl, ethyl, propyl and isopropyl groups. The C1–C3 alkoxy groups include methoxy, ethoxy, and n-and isopropoxy groups. The halogenated C1–C3 alkoxy groups include difluoromethoxy and 2-chloroethoxy groups.

For U, V and W, the ranges of the halogen atoms, C1–C6 alkyl groups and halogenated alkyl groups are the same as those described above. The C1–C6 alkoxy groups and the alkoxy groups in the halogenated alkoxy groups are those corresponding to the alkyl groups having 1 to 6 carbon atoms. The range of the alkyl groups having 1 to 6 carbon atoms is the same as that described above.

Z represents $C(CO_2CH_3)=CHR^8$, $C(CO_2CH_3)=NOCH_3$, $C(CONHCH_3)=NOCH_3$, $C(CSNHCH_3)=NOCH_3$, $N(CO_2CH_3)OCH_3$, $N(CONHCH_3)OCH_3$, $N(CSNHCH_3)OCH_3$, $CH(CO_2CH_3)OCH_3$, $CH(CONHCH_3)OCH_3$ or $CH(CSNHCH_3)OCH_3$, and $R^8$ represents a hydrogen atom, methyl group, ethyl group or methoxy group.

The alkoxyimino-substituted bicyclic derivatives may be in the form of salts thereof. The salts are, for example, sodium salts and potassium salts.

The alkoxyimino-substituted bicyclic derivatives of the present invention can be produced each in the form of a mixture of isomers such as geometrical isomers [(E)/(Z)], optical isomers and diastereomers. When the alkoxyimino-substituted bicyclic derivatives of the present invention are produced in the form of the isomer mixtures, they can be divided into respective isomers by an ordinary method such as the recrystallization or chromatography. When the geometrical isomers [(E)/(Z)] of Z is formed, the (E) isomer is preferred in view of the effect of controlling diseases or insect pests in many cases, and as for the geometrical isomers [(E)/(Z)] of $=N-OR^1$, both isomers exhibit the excellent controlling effects.

The alkoxyimino-substituted bicyclic derivatives of general formula (I) or salts thereof can be easily produced by, for example, the following method:

Production process (1):

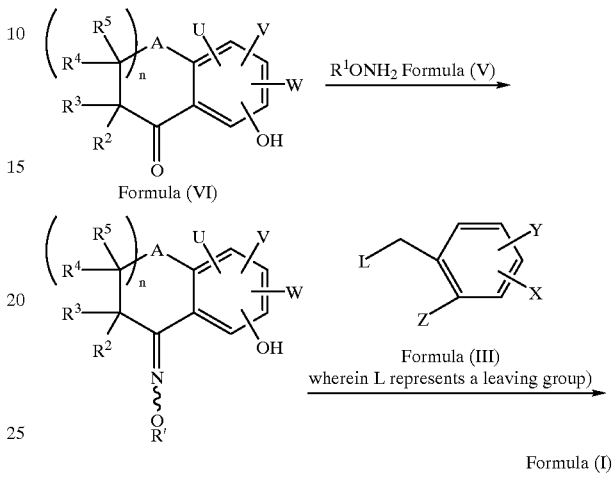

In process (1), the compounds of Formula (I) are produced from compounds of Formula (VI) by a well-known method. As for the compounds of Formula (VI), for example, 3-oxobenzofuran can be produced by a method disclosed in WO 89/05289, 4-oxochroman can be produced by a method disclosed in J. Org. Chem. 59: 1216–1218 (1994) or WO 96/06081, and 1-oxo-indane and 1-oxo-tetrahydronaphthalene can be produced by a method disclosed in WO 91/14674 or U.S. Pat. No. 5,128,362.

The compounds of Formula (II) can be produced by reacting a compound of Formula (VI) with a hydroxyamine compound of Formula (V) or an acid-addition salt (such as hydrochloride or bromate) thereof.

The hydroxyamine compound of Formula (V) or its acid-addition salt is used in an amount of, for example, 1 to 5 equivalents, preferably 1 to 1.5 equivalents, per equivalent of the compound of Formula (VI).

The acids usable for forming the acid-addition salts of the hydroxyamine compounds include inorganic acids such as hydrochloric acid, bromic acid and sulfuric acid, and organic acids such as p-toluenesulfonic acid (tosylic acid).

This reaction can be conducted in a solvent (such as methanol, ethanol or toluene) or in a two-phase (such as toluene/water) system. It is advantageous in some cases to add a base (such as triethylamine, sodium carbonate, potassium carbonate, sodium hydrogencarbonate, potassium hydrogencarbonate, sodium hydroxide or potassium hydroxide) to the reaction mixture. The base is used in an amount of usually 0.05 to 5 equivalents, preferably 1 to 1.5 equivalents, per equivalent of the compound of Formula (VI).

The reaction temperature ranges from −20° C. to a reflux temperature of the solvent, preferably 0 to 50° C., and the reaction time is, for example, 0.5 to 72 hours, preferably 0.5 to 12 hours.

The compounds of Formula (I) can be produced by reacting a compound of Formula (II), thus obtained, with a compound of Formula (III).

The compounds of Formula (III) can be produced by a well-known method. L in Formula (III) is a leaving group such as chlorine atom, bromine atom, p-toluenesulfonate group, methanesulfonate group or trifluoromethanesulfonate group.

Compounds of Formula (III) wherein Z is $C(COOCH_3)=CHR^8$ can be produced by a method disclosed in J. P. KOKAI No. Hei 5-213815, those wherein Z is $C(COOCH_3)=NOCH_3$ can be produced by a method disclosed in EP-386561A; those wherein Z is $CH(COOCH_3)OCH_3$ or $CH(CONHCH_3)OCH_3$ can be produced by a method disclosed in WO 95/27693; and those wherein Z is $N(COOCH_3)OCH_3$ or $N(CONHCH_3)OCH_3$ can be produced by a method disclosed in WO 93/15046.

In the reaction of a compound of Formula (II) with a compound of Formula (III), the former is used in an amount of, for example, 0.5 to 3 equivalents, preferably 0.8 to 1.5 equivalents, per equivalent of the latter.

The reaction of compound (II) with compound (III) can be conducted in the presence of a base (such as triethylamine, sodium carbonate, potassium carbonate, sodium hydrogencarbonate, potassium hydrogencarbonate, sodium hydroxide, potassium hydroxide or sodium hydride) in a solvent (such as acetone, acetonitrile, dimethyl sulfoxide, dimethylformamide, N-methylpyrrolidone or pyridine). The base is used in an amount of 1 to 5 equivalents, preferably 1 to 1.5 equivalents, per equivalent of the compound of Formula (III). It is advantageous in some cases to add a catalyst such as tris-(3,6-dioxoheptyl)amine to the reaction mixture.

The reaction temperature is suitably selected in the range of −20° C. to a refluxing temperature of the solvent, preferably 0 to 50° C., and the reaction time is 0.5 to 72 hours, preferably 0.5 to 12 hours.

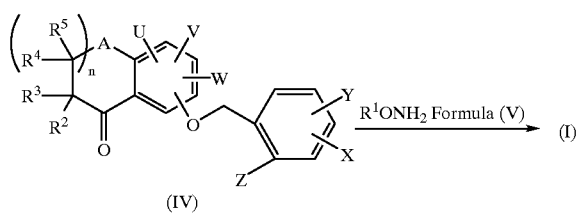

In process (2), each compound of Formula (IV) can be produced by reacting a compound of Formula (VI) with a compound of Formula (III). The compounds of Formula (I) can be produced by reacting a compound of Formula (IV) with a hydroxyamine compound of Formula (V) or an acid addition salt (such as hydrochloride or bromate).

The hydroxyamine compound of Formula (V) or acid addition salt thereof is used in an amount of, for example, 1 to 5 equivalents, preferably 1 to 1.5 equivalents, per equivalent of the compound of Formula (IV).

This reaction can be conducted in a solvent (such as methanol, ethanol or toluene) or in a two-phase (such as toluene/water) system. It is advantageous in some cases to add a base (such as triethylamine, sodium carbonate, potassium carbonate, sodium hydrogencarbonate, potassium hydrogencarbonate, sodium hydroxide or potassium hydroxide) to the reaction mixture. The base is used in an amount of usually 1 to 5 equivalents, preferably 1 to 1.5 equivalents, per equivalent of the compound of Formula (IV).

The reaction temperature is suitably selected in the range of from −20° C. to a reflux temperature of the solvent, preferably 0 to 50° C., and the reaction time is, for example, 0.5 to 72 hours, preferably 0.5 to 12 hours.

Production process (3):

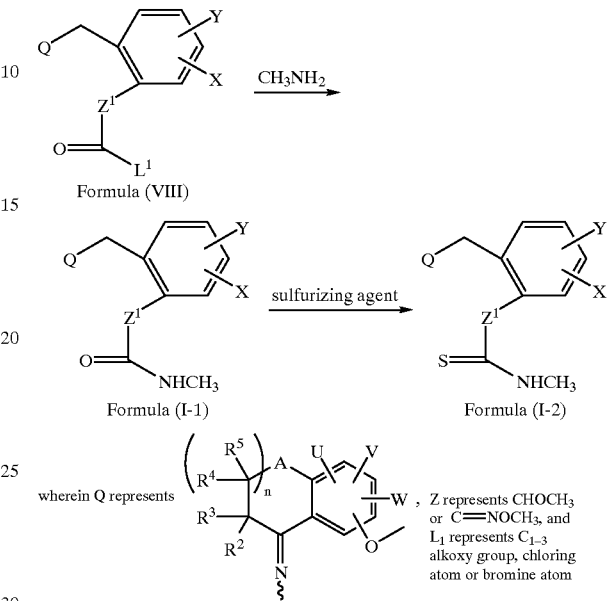

In this process, compounds of Formula (I-1) can be produced by reacting compounds of Formula (VII) with monomethylamine. Monomethylamine is used in an amount of, for example, 1 to 10 equivalents, preferably 1 to 3 equivalents, per equivalent of a compound of formula (VII).

The reaction is preferably conducted in a solvent (such as methanol, ethanol, tetrahydrofuran, diethyl ether or water) at a temperature suitably selected in the range of from −20° C. to a reflux temperature of the solvent, preferably 0 to 50° C., for a reaction time of, for example, 0.5 to 72 hours, preferably 0.5 to 12 hours.

Compounds of Formula (I-2) can be produced by sulfurizing compounds of Formula (I-1). The sulfurizing agent (such as phosphorus pentasulfide or Lawesson's reagent) is used in an amount of, for example, 1 to 5 equivalents, preferably 1 to 2 equivalents, per equivalent of the compound of Formula (I-1).

The reaction is preferably conducted in a solvent (such as toluene, xylene or pyridine) at a temperature suitably selected in the range of from room temperature to a reflux temperature of the solvent, preferably 80 to 150° C., for a reaction time of, for example, 0.5 to 72 hours, preferably 0.5 to 12 hours.

Production process (4):

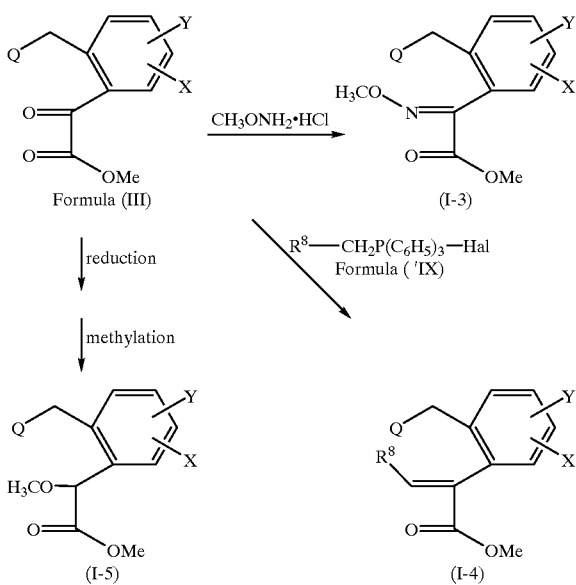

In this process, compounds of Formula (VIII) can be produced by reacting a compound of Formula (II) with methyl (2-bromomethylphenyl)glyoxylate.

The compounds of Formula (I-3) can be produced by reacting a compound of Formula (VIII) with methoxyamine hydrochloride.

The amount of methoxyamine hydrochloride is used in an amount of, for example, 1 to 10 equivalents, preferably 1 to 3 equivalents, per equivalent of the compound of Formula (VIII).

This reaction can be conducted in a solvent (such as methanol, ethanol or toluene) or in two-phase (such as toluene/water) system. It is advantageous in some cases to add a base (such as triethylamine, sodium carbonate, potassium carbonate, sodium hydrogencarbonate, potassium hydrogencarbonate, sodium hydroxide or potassium hydroxide) to the reaction mixture. The base is used in an amount of, for example, 1 to 10 equivalents, preferably 1 to 3 equivalents, per equivalent of the compound of Formula (VIII).

The reaction temperature is suitably selected in the range of from −20° C. to a reflux temperature of the solvent, preferably 0 to 50° C., and the reaction time is, for example, 0.5 to 72 hours, preferably 0.5 to 12 hours.

The compounds of Formula (I-4) can be produced by reacting a compound of Formula (VIII) with a compound of Formula (IX) (Wittig reagent or Wittig/Horner reagent) by a known method (such as a method disclosed in J. P. KOKAI No. Hei 5-213815).

The compound of Formula (VIII) is used in an amount of, for example, 0.1 to 3 equivalents, preferably 0.2 to 1.5 equivalents, per equivalent of the compound of Formula (IX).

The reaction can be conducted in the presence of a base (such as sodium methoxide, potassium t-butoxide or sodium hydride) in a solvent (such as tetrahydrofuran, diethyl ether, dimethyl sulfoxide or dimethylformamide). The base is used in an amount of, for example, 1 to 5 equivalents, preferably 1 to 1.5 equivalents, per equivalent of the compound of Formula (IX).

The reaction temperature is suitably selected in the range of from −20° C. to a reflux temperature of the solvent, preferably −10 to 30° C., and the reaction time is, for example, 0.5 to 72 hours, preferably 0.5 to 12 hours.

The compounds of Formula (I-5) can be produced by reacting a compound of Formula (VIII) with a reducing agent and then methylating the reaction product.

The reducing agent is one usually used for the reduction of ketones, such as sodium borohydride, lithium borohydride or lithium aluminum hydride. The reducing agent is used in an amount of, for example, 0.5 to 5 equivalents, preferably 1 to 1.5 equivalents, per equivalent of the compound of Formula (VIII).

The reaction is preferably conducted in a solvent (such as methanol, ethanol, tetrahydrofuran, diethyl ether or water) or in a two-phase system (such as ethyl acetate/water) at a temperature suitably selected in the range of from −20° C. to a reflux temperature of the solvent, preferably 0 to 50° C., for 0.5 to 72 hours, preferably 0.5 to 6 hours.

A compound of Formula (I-5) can be obtained by methylating the resultant alcohol compound.

The methylating agents usable herein are, for example, methyl chloride, methyl bromide, methyl iodide and dimethylsulfuric acid. The methylating agent is used in an amount of, for example, 0.5 to 5 equivalents, preferably 0.8 to 1.5 equivalents, per equivalent of the obtained alcohol compound.

The reaction can be conducted by using a base (such as sodium methoxide, potassium t-butoxide, sodium hydroxide, potassium hydroxide or sodium hydride) in an inert solvent (such as acetonitrile, tetrahydrofuran, diethyl ether, dimethylformamide or N-methylpyrrolidone). The base is used in an amount of, for example, 1 to 5 equivalents, preferably 1 to 1.5 equivalents, per equivalent of the compound of Formula (III).

The reaction temperature is suitably selected in the range of from −20° C. to a reflux temperature of the solvent, preferably 0 to 50° C., and the reaction time is, for example, 0.5 to 72 hours, preferably 0.5 to 12 hours.

Production process (5):

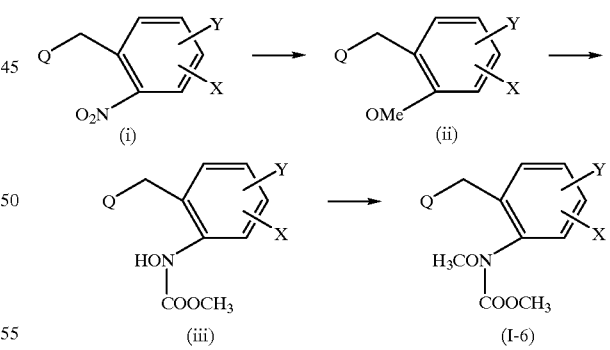

In this process, compounds (i) can be produced by, for example, reacting a compound of Formula (II) with o-nitrobenzyl bromide.

Compound (ii) can be obtained by reacting compound (i) with ammonium chloride in the presence of zinc [Organic Syntheses Coll. Vol. III, p. 668 (1955)]. Then compound (ii) is reacted with methyl chloroformate to obtain compound (iii). A compound of Formula (I-6) can be obtained by treating compound (iii) in the same manner as that of the methylation in production process (4).

Production process (6):

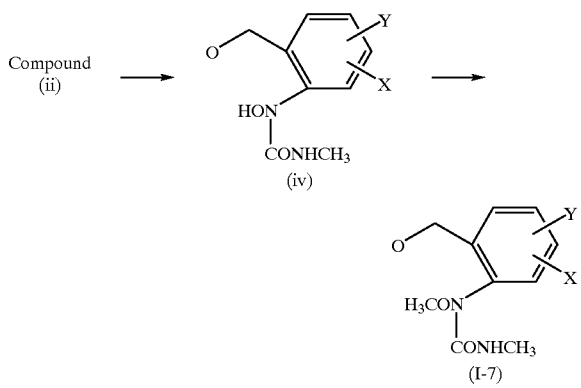

In this process, compounds (iv) can be obtained by reacting compound (ii) with, for example, methyl isocyanate. Compounds of Formula (I-7) can be obtained by methylating compounds (iv) in the same manner as that of the methylation in production process (4).

Production process (7)

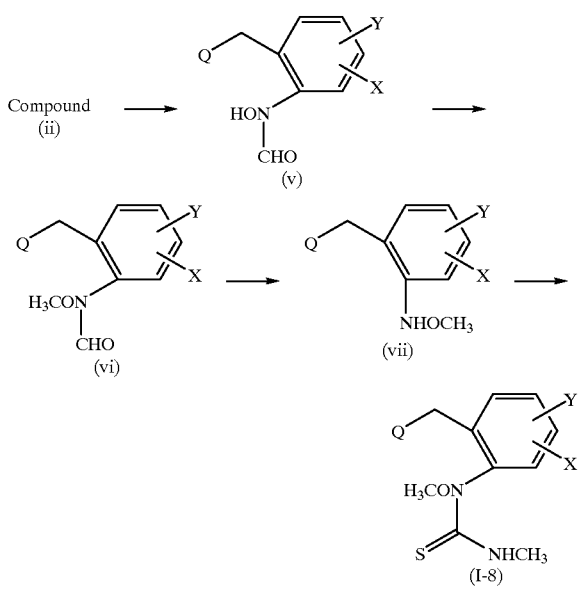

In this process, compound (v) can be obtained by an ordinary method such as a method which comprises formylating compound (ii) with formic acid and acetic anhydride. Compound (vi) can be obtained by methylating compound (v) in the same manner as that of preparation process (4). Then, compound (vi) is hydrolyzed to obtain compound (vii), which is reacted with thiophosgene, and the product is reacted with monomethylamine or methyl thioisocyanate to obtain a compound of Formula (I-8).

The compounds of the present invention even in an extremely low concentration are effective on various harmful insect pests. The insect pests which can be controlled by the compounds of the present invention include, for example, insects of the order of beetles such as scarab beetles, leaf beetles, 28-spotted lady beetles (*Epilachna sparsa orientalis*) and rice water weevil (*Lissorhoptrus oryzophilus*); lepidopterons such as cabbage army worms (*Mamestra brassicae*), common cabbage worms (*Pieris rapae crucivora*), diamond back moth (*Plutella xylostera*), beet semi-looper (*Autographa nigrisigna*), leaf folders and rice borers; insects of Hemiptera such as plant hoppers, leaf hoppers, white flies, aphids and coccidia; thrips such as yellow tea thrips (*Scirtothrips dorsalis*) and *Thrips palmi*; sanitary insect pests such as mosquitoes, flies, cockroaches, fleas and lice, stored grain insect pests, clothes moths, house insect pests, plant parasitic nematodes such as root-knot nematodes and root-lesion nematodes (*Pratylenchus paratensis*); and plant parasitic spider mites such as two-spotted spider mite (*Tetranychus urticae*), kanzawa spider mite (*Tetranychus kanzawai*) and citrus red mite (*Panonychus citri*). They are also effective on soil insect pests. The term "soil insect pests" herein include gastropods such as slugs and snails; and wood lice (isopods) such as pill bugs and sow bugs. Further, they are effective on plant parasitic spider mites which are resistant to Dicofol and organophosphorus pesticides, and aphids and houseflies resistant to organophosphorus pesticides.

The plant diseases which can be controlled by the compounds of the present invention include, for example, Rice blast (*Pyricularia oryzae*), Rice sheath blight (*Rhizoctonia solani*), Rice brown spot (*Chochliobolus miyabeanus*), Wheat eye spot (*Pseudocercosporella herpotrichoides*), powdery mildews of various host plants such as *Erysiphe graminis, Sphaerotheca fuliginea* and *Uncinula necator,* Oat crown rust (*Puccinia coronata*) and rust of other plants, *Botrytis cinerea* of Grape and gray-mold of other plants, Cucumber stem rot (*Sclerotinia sclerotiorum*) and stem rot of other plants, Poteto late blight (*Phytophthora infestans*) and late blight and phytophthora diseases of other plants, downy mildew of various plants such as *Pseudoperonospora cubensis* and *Plasmopara viticola,* scab of various plants such as *Venturia inaequalis* and *Venturia nashicola,* Alternaria diseases of varius plants such as *Alternaria mali* and *Alternaria kikuchiana,* Monilinia disease of varius plants such as Apple blossom blight (*Monilinia mali*) and Peach brown rot (*Monilinia fructicola*), Citrus melanose (*Diaporthe citri*) and Citrus penicillium rot (*Penicillium italicum*). The compounds of the present invention have extremely excellent effects of controlling these diseases and, in particular, the excellent effects of them can be exhibited even in a low concentration.

The agents of the present invention for controlling diseases and insect pests have a remarkable effect of controlling the diseases and insect pests which harm paddy field crops, non-paddy field crops, fruit trees, vegetables and other crops as well as flowering plants. They are used for treating water in paddy fields, and also stems, leaves, soils, seeds and bulbs of fruit trees, vegetables and other crops as well as flowering plants in paddy fields and non-paddy fields before the diseases or insect pests appear or when they are found. The intended effects of the agents of the present invention for controlling diseases and insect pests are thus exhibited.

The concentration and amount of the compounds of the present invention to be used cannot indiscriminately be limited because they vary depending on the crops to be treated, method of the application, form of the preparation and dose. However, in the treatment of stems and leaves, the concentration of the active ingredient is usually 0.1 to 10,000 ppm, desirably 1 to 2,000 ppm. The concentration can be suitably changed depending on the form of the preparation, application method, purpose, period and site of the application, and state of the disease or insect pests. For example, in controlling aquatic insect pests, the range of the concentration of the effective ingredient in water is below the above-described range because the insect pests can be controlled even when the preparation having the concentration in the above-described range is applied. As for the dose per a unit area, the compound to be used as the active ingredient is used in an amount of about 0.1 to 5,000 g, preferably 10 to 1,000 g, for every 10 a. of the field. However, in particular cases, the dose can be not within the range.

The compounds of the present invention can be mixed with or used in combination with other pesticides such as insecticides, acaricides, nematicides and fungicides to exhibit more excellent effects. They can also be mixed with or used in combination with an antiviral agent, attractant, herbicide, plant growth regulator or the like.

The compounds usable as active ingredients of the above-described insecticides, acaricides and nematicides include, for example, organophosphoric ester compounds such as O-(4-bromo-2-chlorophenyl) O-ethyl-S-propylphosphorothioate (common name: Profenofos), O-(2, 2-dichlorovinyl) O,O-dimethylphosphate (common name: Dichlorvos), O-ethyl O-[3-methyl-4-(methylthio)phenyl] N-isopropylphosphoroamidate (common name: Fenamiphos), O,O-dimethyl O-(4-nitro-m-tolyl) phosphorothioate (common name: Fenitrothion), O-ethyl O-(4-nitrophenyl)phenylphosphonothioate (common name: EPN), O,O-diethyl O-(2-isopropyl-6-methylpyrimidine-4-yl)phosphorothioate (common name; Diazinon), O,O-dimethyl O-(3,5,6-trichloro-2-pyridyl)phosphorothioate (common name: Chlorpyrifos-methyl), O,S-dimethyl N-acetylphosphoroamidothioate (common name: Acephate), O-(2,4-dichlorophenyl), O-ethyl S-propylphosphorodithioate (common name: Prothiofos) and (RS)-S-sec-butyl O-ethyl 2-oxo-1,3-thiazolidine-3-ylphosphonothioate (common name: Fosthiazate);

carbamate compounds such as 1-naphthyl N-methylcarbamate (common mane: Carbaryl), 2-isopropoxyphenyl N-methylcarbamate (common name: Propoxur) 2-methyl-2-(methylthio) propionaldehyde O-methylcarbamoyloxime (common name: Aldicarb), 2,3-dihydro-2,2-dimethylbenzofuran-7-yl N-methylcarbamate (common name: Carbofuran), dimethyl N,N'-[thiobis(methylimino)carbonyloxy)] bisethanimidothioate (common name: Thiodicarb), S-methyl N-(methylcarbamoyloxy)thioacetimidate (common name: Methomyl), N,N-dimethyl-2-methylcarbamoyloxyimino-2-(methylthio)acetamide (common name: Oxamyl), 2-(ethylthiomethyl)phenyl N-methylcarbamate (common name; Ethiofencarb), 2-dimethylamino-5,6-dimethylpyrimidinnne-4-yl N,N-dimethylcarbamate (common name: Pirimicarb) and 2-sec-butylphenyl N-methylcarbamate (common name: Fenobucarb);

Nereistoxin derivatives such as S,S'-2-dimethylaminotrimethylene bis(thiocarbamate) (common name: Cartap) and N,N-dimethyl-1,2,3-trithian-5-ylamine (common name: Thiocyclam);

organochlorine compounds such as 2,2,2-trichloro-1,1-bis (4-chlorophenyl)ethanol (common name: Dicofol) and 4-chlorophenyl-2,4,5-trichlorophenyl sulfone (common name: Tetradifon);

organometallic compounds such as bis[tris(2-methyl-2-phenylpropyl)tin] oxide (common name: Fenbutatin Oxide);

pyrethroid compounds such as (RS)-α-cyano-3-phenoxybenzyl(RS)-2-(4-chlorophenyl)-3-methylbutyrate (common name: Fenvalerate), 3-phenoxybenzyl(IRS)-cis, trans-3-(2,2-dichlorovinyl)-2,2-dimethylcyclopropanecarboxylate (common name: Permethrin), (RS)-α-cyano-3-phenoxybenzyl(IRS)-cis, trans-3-(2,2-dichlorovinyl)-2,2-dimethylcyclopropanecarboxylate (common name: Cypermethrin), (S)-α-cyano-3-phenoxybenzyl(IR)-cis-3-(2,2-dibromovinyl)-2,2-dimethylcyclopropanecarboxylate (common name: Deltamethrin), (RS)-α-cyano-3-phenoxybenzyl(IRS)-cis, trans-3-(2-chloro-3,3,3-trifluoropropenyl)-2,2-dimethylcyclopropanecarboxylate (common name: Cyhalothrin), 4-methyl-2,3,5,6-tetrafluorobenzyl-3-(2-chloro-3,3,3-trifluoro-1-propenyl)-2,2-dimethylcyclopropanecarboxylate (common name: Tefluthrin) and 2-(4-ethoxyphenyl)-2-methylpropyl 3-phenoxybenzyl ether (common name: Ethofenprox);

benzoylurea compounds such as 1-(4-chlorophenyl)-3-(2, 6-difluorobenzoyl)urea (common name: Diflubenzuron), 1-[3,5-dichloro-4-(3-chloro-5-trifluoromethyl-2-pyridyloxy)phenyl]-3-(2,6-difluorobenzoyl)urea (common name: Chlorfluazuron), 1-(3,5-dichloro-2,4-difluorophenyl)-3-(2,6-difluorobenzoyl)urea (common name: Teflubenzuron);

juvenile hormone-like compounds such as isopropyl (2E, 4E)-11-methoxy-3,7,11-trimethyl-2,4-dodecadienoate (common name: Methoprene);

pyridazinone compounds such as 2-t-butyl-5-(4-t-butylbenzylthio)-4-chloro-3(2H)-pyridazinone (common name: Pyridaben);

pyrazole compounds such as t-butyl 4-[(1,3-dimethyl-5-phenoxypyrazole-4-yl)methyleneaminoxymethyl] benzoate (common name: Fenpyroximate);

nitro compounds such as 1-(6-chloro-3-pyridylmethyl)-N-nitroimidazolidine-2-ylideneamine (common name: Imidacloprid), 1-[N-(6-chloro-3-pyridylmethyl)-N-ethylamino]-1-methylamino-2-nitroethylene (European Patent Publication No. 302389), 2-methylamino-2-[N-methyl-N-(6-chloro-3-pyridylmethyl)amino]-1-nitroethylene (European Patent Publication No. 302389), 1-(6-chloro-3-pyridylmethyl)amino-1-dimethylamino-2-nitroethylene (European Patent Publication No. 302389), 1-(6-chloro-3-pyridylmethyl)-2-(1-nitro-2-llylthioethylidene)imidazolidine (European Patent Publication No. 437784), 1-(6-chloro-3-pyridylmethyl)-2-(1-nitro-2-ethylthioethylidene) imidazolidine (European Patent Publication No. 437784), 1-(6-chloro-3-pyridylmethyl)-2-(1-nitro-2-β-methylallylthioethylidene)imidazolidine (European Patent Publication No. 437784), 1-(6-chloro-3-pyridylmethyl)-3-methyl-2-nitroguanidine (European Patent Publication No. 383091), 1-(6-chloro-3-pyridylmethyl)-3.3-dimethyl-2-nitroguanidine (European Patent Publication No. 383091), 3-(6-chloro-3-pyridylmethyl)-2-nitromethylene-thiazolidine (European Patent Publication No. 192060), 1-(6-chloro-3-pyridylmethyl)-2-(nitromethylene) imidazolidine (European Patent Publication No. 163855), 6-(6-chloro-3-pyridylmethylamino)-1,3-dimethyl-5-nitro-1,2,3,4-tetrahydropyrimidine (European Patent Publication No. 366085) and 1-(6-chloro-3-pyridylmethyl)-5-nitro-3-methyl-6-methylamino-1,2,3,4-tetrahydropyrimidine (European Patent Publication No. 366085);

dinitro compounds, organosulfur compounds, urea compounds, triazine compounds, hydrazine compounds and other compounds such as 2-tertbutylimino-3-isopropyl-5-phenyl-3,4,5,6-tetrahydro-2H-1,3,5-thiadiazine-4-on (common name: Buprofezin), trans-(4-chlorophenyl)-N-cyclohexyl-4-methyl-2-oxothiazolidinone-3-carboxamide (common name: Hexythiazox), N-methylbis(2,4-xylyliminomethyl)amine (common name: Amitraz), N'-(4-chloro-o-tolyl)-N,N-dimethylformamidine (common name: Chlordimeform) and (4-ethoxyphenyl)-[3-(4-fluoro-3-phenoxyphenyl)propyl](dimethyl)silane (common name: Silafluofen). Further, the compounds of the present invention may also be used in mixture or combination with microbial pesticides such as BT and insect pathogenic viruses, and also antibiotics such as avermectin and milbemycin.

Compounds usable as the active ingredients of the fungicides include pyrimidinamine compounds such as 2-anilino-4-methyl-6-(1-propinyl)pyrimidine (common name: Mepanipyrim) and 4,6-dimethyl-N-phenyl-2-pyrimidinamine (common name: Pyrimethanil);

azole compounds such as 1-(4-chlorophenoxy)-3,3-dimethyl-1-(1H-1,2,4-triazole-1y)butanone (common name: Triadimefon), 1-(biphenyl-4-yloxy)-3,3-dimethyl-1-(1H,1,2,4-triazole-1-yl)butane-2-ol (common name: Bitertanol), 1-[N-(4-chloro-2-trifluoromethylphenyl]-2-propoxyacetimidoyl] imidazole (common name: Triflumizole), 1-[2-(2,4-dichlorophenyl)-4-ethyl-1,3-dioxolane-2-ylmethyl]-1H-1,2,4-triazole (common name: Etaconazole), 1-[2-(2,4-dichlorophenyl)-4-propyl-1,3-dioxolane-2-ylmethyl]-1H-1,2,4-triazole (common name: Propiconazole), 1-[2-(2,4-dichlorophenyl)pentyl]-1H-1,2,4-triazole (common name: Penconazole), bis(4-fluorophenyl)(methyl)(1H-1,2,4-triazole-1-ylmethyl)silane (common name: Flusilazole), 2-(4-chlorophenyl)-2-(1H, 1,2,4-triazole-1-ylmethyl) hexanenitrile (common name: Myclobutanil), (2RS,3RS)-2-(4-chlorophenyl)-3-cyclopropyl-1-(1H-1,2,4-triazole-1-yl)butane-2-ol (common name: Cyproconazole), (RS)-1-(4-chlorophenyl)-4,4-dimethyl-3-(1H-1,2,4-triazole-1-ylmethyl)pentane-3-ol (common name: Terbuconazole), (RS)-2-(2,4-dichlorophenyl)-1-(1H-1,2,4-triazole-1-yl)hexane-2-ol (common name: Hexaconazole), (2RS,5RS)-5-(2,4-dichlorophenyl)tetrahydro-5-(1H-1,2,4-triazole-1-ylmethyl)-2-furyl 2,2,2-trifluoroethyl ether (common name: Furconazole-cis) and N-propyl-N-[2-(2,4,6-trichlorophenoxy)ethyl]imidazole-1-carboxamide (common name: Prochloraz);

quinoxaline compounds such as 6-methyl-1,3-dithiolo[4,5-b]quinoxaline-2-on (common name: Quinomethionate); dithiocarbamate compounds such as manganese ethylene bis(dithiocarbamate) polymer (common name: maneb), zinc ethylene bis (dithiocarbamate) polymer (common name: zineb), complex of zinc with manganese ethylene bis (dithiocarbamate) (maneb) (common name: Mancozeb), dizinc bis(dimethyldithiocarbamato) ethylene bis(dithiocarbamate) (common name: Polycarbamate) and zinc propylene bis (dithiocarbamate) polymer (common name: Propineb);

organochlorine compounds such as 4,5,6,7-tetrachlorophthalide (common name: Fthalide), tetrachloroisophthalonitrile (common name: Chlorothalonil) and pentachloronitrobenzene (common name: Quintozene); benzimidazole compounds such as methyl 1-(butylcarbamoyl)benzimidazole-2-yl carbamate (common name: Benomyl), dimethyl 4,4'-(o-phenylene)bis(3-thioallophanate) (common name: Thiophnate-Methyl) and methyl benzimidazole-2-ylcarbamate (common name: Carbendazim);

Pyridinamine compounds such as 3-chloro-N-(3-chloro-2,6-dinitro-4-α,α,α-trifluorotolyl)-5-trifluoromethyl-2-pyridinamine (common name: Fluazinam); cyanoacetamide compounds such as 1-(2-methoxyiminoacetyl)-3-ethylurea (common name: Cymoxanil);

phenylamide compounds such as methyl N-(2-methoxyacetyl)-N-(2,6-xylyl)-DL-alaninate (common name: Metalaxyl), 2-methoxy-N-(2-oxo-1,3-oxazolidine-3-yl)aceto-2',6'-xylidide (common name: Oxadixyl), (±)-α-2-chloro-N-(2,6-xylylacetamido)-γ-butyrolactone (common name: Ofurace), methyl N-phenylacetyl-N-(2,6-xylyl)-DL-alaninate (common name: Benalaxyl), methyl N-(2-furoyl)-N-(2,6-xylyl)-DL-alaninate (common name: Furalaxyl) and (±)-α-[N-(3-chlorophenyl)cyclopropanecarboxamido]-γ-butyrolactone (common name: Cyprofuram);

sulfenic acid compounds such as N-dichlorofluoromethylthio-N',N'-dimethyl-N-phenylsulfamide (common name: Dichlofluanid); copper compounds such as cupric hydroxide (common name: cupric hydroxide) and copper 8-quinolinolate (common name: Oxine-Copper);

isoxazole compounds such as 5-methylisoxazole-3-ol (common name: Hydroxyisoxazole); organophosphorus compounds such as aluminum tris (ethylphosphonate) (common name: Fosetyl-aluminum), O-2,6-dichloro-p-tolyl-O,O-dimethylphosphorothioate (common name: Tolcofos-methyl), S-benzyl O,O-diisopropyl phosphorothioate, O-ethyl S,S-diphenylphosphorodithioate and aluminum ethyl hydrogenphosphonate;

N-halogenothioalkyl compounds such as N-(trichloromethylthio)cyclohex-4-en-1,2-dicarboximide (common name: Captan), N-(1,1,2,2-tetrachloroethylthio)cyclohex-4-en-1,2-dicarboximide (common name: Captafol) and N-(trichloromethylthio) phthalimide (common name: Folpet);

dicarboxyimide compounds such as N-(3,5-dichlorophenyl)-1,2-dimethylcyclopropane-1,2-dicarboximide (common name: Procymidone), 3-(3,5-dichlorophenyl)-N-isopropyl-2,4-dioxoimidazolidine-1-carboxamide (common name: Iprodione) and (RS)-3-(3,5-dichlorophenyl)-5-methyl-5-vinyl-1,3-oxazolidine-2,4-dion (common name: Vinclozlin);

benzanilide compounds such as α,α,α-trifluoro-3'-isopropoxy-o-toluanilide (common name: Flutolanil) and 3'-isopropoxy-o-toluanilide (common name: Mepronil); benzamide compounds such as 2-(1,3-dimethylpyrazole-4-ylcarbonylamino)-4-methyl-3-pentenenitrile (a compound described in British Patent No. 2,190,375) and α-(nicotinylamino)-(3-fluorophenyl)acetonitrile (a compound described in J. P. KOKAI No. Sho 63-135364);

piperazine compounds such as N,N'-[piperazine-1,4-diylbis(trichloromethyl)methylene]diformamide (common name: Triforine); pyridine compounds such as 2',4'-dichloro-2-(3-pyridyl)acetophenone O-methyloxime (common name: Pyrifenox);

carbinol compounds such as (±)-2,4'-dichloro-α-(pyrimidine-5-yl)benzhydryl alcohol (common name: Fenarimol), (±)-2,4'-difluoro-α-(1H-1,2,4-triazole-1-ylmethyl)benzhydryl alcohol (common name: Flutriafol);

piperidine compounds such as (RS)-1-[3-(4-tert-butylphenyl)-2-methylpropyl]piperidine (common name: Fenpropidine);

morpholine compounds such as (±)-cis-4-[3-(4-tert-butylphenyl)-2-methylpropyl]-2,6-dimethylmorpholine (common name: Fenpropimorph);

organotin compounds such as triphenyltin hydroxide (common name: Fentin hydroxide): triphenyltin acetate (common name: Fentin acetate);

urea compounds such as 1-(4-chlorobenzyl)-1-cyclopentyl-3-phenylurea (common name: Pencycuron);

cinnamic acid compounds such as (E,Z)4-[3-(4-chlorophenyl)-3-(3,4-dimethoxyphenyl)acryloyl] morpholine (common name: Dimethomorph);

phenyl carbamate compounds such as isopropyl 3,4-diethoxycarbanylate (common name: Diethofencarb);

cyanopyrrole compounds such as 3-cyano-4-(2,2-difluoro-1,3-benzodioxol-4-yl)pyrrole (common name: Fludioxonil) and 3-(2',3'-dichlorophenyl)-4-cyanopyrrole (common name: Fenpiclonil);

anthraquinone compounds; crotonic acid compounds; and antibiotics.

The weight ratio of the alkoxyimino-substituted bicyclic derivative of above Formula (I) or its salt to the other component to be used in the form of a mixture or in combination with the former is usually 1:300 to 300:1, desirably 1:100 to 100:1. Particularly when the benzyloxybenzene derivative is used in the form of a mixture thereof with a pyrimidinamine compound, organochlorine compound, pyridinamine compound or cyanopyrrole compound, an excellent effect of controlling various gray molds can be expected.

When the alkoxyimino-substituted bicyclic derivatives or salts thereof of the present invention are used in practice, each of them is usually mixed with a powder, solid carrier, solvent, surfactant and other adjuvants for the preparation to form an emulsion, aqueous solution, microemulsion, wettable powder, dust, aqueous or oily suspension, water-dispersible granule, water-soluble powder or microcapsules and others. These preparations contain 0.002 to 80% by weight, preferably 0.01 to 70% by weight, of the above-described compound.

The solid carriers include kaolin clay, attapulgite clay, bentonite, acid clay, pyrophyllite, talc, diatomaceous earth, calcite, walnut shell powder, urea, ammonium sulfate, synthetic silicic acid hydrate and others.

The solvents are, for example, aromatic and aliphatic hydrocarbons such as xylene, naphthas, methylnaphthalene, paraffins and machine oil; alcohols such as isopropanol, butanol, propylene glycol, ethylene glycol, cellosolve and carbitol; ketones such as acetone, cyclohexanone and isophorone; vegetable oils such as soybean oil and cotton seed oil; dimethyl sulfoxide; N,N-dimethylformamide; N-methylpyrrolidone; acetonitrile; water and others.

The surfactants used for emulsification, dispersion, wetting or the like include anionic surfactants such as lignin sulfonates, alkylnaphthalenesulfonates, naphthalenesulfonates/formaldehyde condensates, alkylsulfates, alkylsulfonates, alkylarylsulfonates, dialkylsulfosuccinates, polyoxyethylene alkylaryl ether sulfates (sulfonates or phosphates), polyoxyethylene alkyl ether sulfates (phosphates or sulfonates), and polyoxyethylene styrenated and benzylated phenyl ether phosphoric acid or phosphates (sulfates, sulfonates); and nonionic surfactants such as polyoxyethylene alkyl ethers, polyoxyethylene alkylaryl ethers, polyoxyethylene fatty acid esters, polyoxyethylene/polyoxypropylene block copolymers, sorbitan fatty acid esters, polyoxyethylene sorbitan fatty acid esters, and polyoxyethylene styrenated or benzylated phenyl ethers.

Other adjuvants include alginates, polyvinyl alcohols, acacia gum, carboxymethylcellulose, Xantham gum, Welan gum, isopropyl hydrogen phosphate, etc.

A wettable powder, which is a typical example of the preparations, can be prepared by mixing about 5 to 50 parts by weight of an alkoxyimino-substituted bicyclic derivative or a salt thereof of the present invention with 2 to 5 parts by weight of an anionic surfactants and solid carriers in an amount sufficient for making the whole amount 100 parts by weight, and pulverizing the mixture.

A dust can be prepared by mixing 0.01 to 10 parts by weight of an alkoxyimino-substituted bicyclic derivative or a salt thereof of the present invention with 0.1 to 0.5 part by weight of the above-surfactants, oils and adjuvants and fine mineral powders selected from among solid carriers.

An emulsifiable concentrate can be prepared by mixing 1 to 70 parts by weight of an alkoxyimino-substituted bicyclic derivative or a salt thereof of the present invention with 5 to 15 parts by weight of non-ionic surfactants, 1 to 10 parts by weight of anionic surfactants and a pharmaceutically acceptable solvent(s) in an amount sufficient for making the whole amount 100 parts by weight.

An aqueous suspension can be prepared by mixing 5 to 50 parts by weight of an alkoxyimino-substituted bicyclic derivative or a salt thereof of the present invention with 1 to 5 parts by weight of a non-ionic surfactant or anionic surfactant and water in an amount sufficient for making the whole amount 100 parts by weight, then wet-milling (grinding) the above mixture until the particle size has been reduced to 0.1 to 3 $\mu$m, preferably 0.5 to 2$\mu$m, and mixing the obtained mixture with 0.1 to 1 part by weight of thickening agent(s), and other additives.

A water-dispersible granule comprises granules composed of 5 to 50 parts by weight of a finely pulverized alkoxyimino-substituted bicyclic derivative or the salt thereof of the present invention, 90 to 40 parts by weight of an inorganic salt and/or fine mineral powder selected from among the solid carriers, 0.1 to 5 parts by weight of a binder and 5 to 10 parts by weight of surfactants. When the granule is fed into water, it is rapidly disintegrated and dispersed therein.

EXAMPLES

The following synthesis examples and application examples will further illustrate the present invention, which by no means limit the scope of the present invention.

Synthesis Example 1

Synthesis of (E) methyl methoxyimino-[2-(3-methoxyimino-2,3-dihydrobenzofuran-6-yloxymethyl)-phenyl]acetate (a-4):

i) Synthesis of 3-methoxyimino-6-hydroxy-2,3-dihydrobenzofuran (intermediate ia-1):

2.5 g of methoxyamine hydrochloride was added to a solution of 4.0 g of 3-oxo-6-hydroxy-2,3-dihydrobenzofuran and 5.0 g of Molecular Sieves (3A) in 50 ml of methanol, and they were reacted at room temperature for 16 hours. After the completion of the reaction, the reaction liquid was filtered, and the filtrate was concentrated. The residue was poured into ice/water, and the solids thus formed were taken by the filtration, washed with water and dried to obtain 3.5 g of crystals [having a m. p. of 150° C. (decomposition) and $^1$H-NMR data shown in the following table].

ii) 3.4 g of (E) methyl methoxyimino-(2-bromomethylphenyl)acetate was added to 9.0 g of potassium carbonate and 1.8 g of 3-methoxyimino-6-hydroxy-2,3-dihydrobenzofuran in 30 ml of N,N-dimethylformamide, and they were reacted at room temperature for 6 hours. After the completion of the reaction, the reaction liquid was poured in ice/water. After the extraction with ethyl acetate, the extract was washed with water, dried over anhydrous magnesium sulfate and concentrated under reduced pressure. The residue thus obtained was purified by the silica gel chromatography (hexane:ethyl acetate) to obtain 3.0 g of the title compound (having a m. p. of 108–110° C. and $^1$H-NMR data shown in the following table).

Synthesis Example 2

Synthesis of (E) methoxyimino-[2-(3-methoxyimino-2,3-dihydro-benzofuran-6-yloxymethyl)phenyl]-N-methyl-acetamide (a-5):

5 ml of 40% monomethylamine/methanol solution was added to a solution of 1.5 g of the methyl acetate compound obtained in Synthesis Example 1 in 10 ml methanol, and the reaction was carried out at room temperature for 6 hours. After the completion of the reaction, the reaction liquid was poured into ice/water, and the solids thus formed were taken by the filtration, washed with water and dried to obtain 1.3 g of the title compound (having a m. p. of 143–145° C. and 1H-NMR data shown in the following table].

Synthesis Example 3

Synthesis of (E) methyl methoxyimino-[2-(3-oxo-2,3-dihydrobenzofuran-6-yloxymethyl)phenyl]acetate (intermediate ib-1):

3.8 g of (E) methyl methoxyimino-(2-bromomethylphenyl) acetate was added to 9.0 g of potassium carbonate and 2.0 g of 3-oxo-6-hydroxy-2,3-dihydrobenzofuran in 30 ml of N,N-dimethylformamide, and the reaction was carried out at room temperature for 6 hours. After the completion of the reaction, the reaction liquid was poured in ice/water. After the extraction with ethyl acetate, the extract was washed with water, dried over anhydrous magnesium sulfate and concentrated under reduced pressure. The residue thus obtained was purified by the silica gel chromatography (hexane:ethyl acetate) to obtain 3.0 g of the title compound (having a m. p. of 134–137° C. and $^1$H-NMR data shown in the following table).

Synthesis Example 4

Synthesis of (E) methoxyimino-[2-(3-oxo-2,3-dihydrobenzofuran-6-yloxymethyl)-phenyl]-N-methyl-acetamide (intermediate ib-2):

20 ml of 40% monomethylamine/methanol solution was added to a solution of 4.5 g of the methyl acetate ester compound obtained in Synthesis Example 3 in 20 ml of methanol, and the reaction was carried out at room temperature for 6 hours. After the completion of the reaction, the reaction liquid was concentrated under reduced pressure, and the residue was poured in 100 ml of 5% aqueous hydrochloric acid solution. After the extraction with ethyl acetate, the extract was washed with water, dried over anhydrous magnesium sulfate and concentrated under reduced pressure. The residue thus obtained was purified by the silica gel chromatography (hexane ethyl acetate) to obtain 2.5 g of the title compound (having a m. p. of 149–151° C. and $^1$H-NMR data shown in the following table).

Synthesis Example 5

Synthesis of (E) methoxyimino-[2-(3-ethoxyimino-2,3-dihydrobenzofuran-6-yloxymethyl)-phenyl]-N-methyl-acetamide (a-37):

1.0 g of ethoxyamine hydrochloride was added to a solution of 0.5 g of the compound obtained in Synthesis Example 4 and 3.0 g of molecular sieves (3A) in 20 ml of methanol, and the reaction was carried out at room temperature for 16 hours. After the completion of the reaction, the reaction liquid was filtered, and the filtrate was concentrated. The residue was poured into ice/water, and the solids thus formed were taken by the filtration, washed with water and dried to obtain 0.240 g of the title compound [having a m.p. of 110–113° C. and $^1$H-NMR data shown in the following table].

Synthesis Example 6

Synthesis of methyl N-[2-(3-methoxyimino-2,3-dihydro-benzofuran-6-yloxymethyl)-phenyl]-N-methoxycarbamate (a-7):

i) A solution of 8.4 g of [2-(3-methoxyimino-2,3-dihydrobenzofuran-6-yl)-2-nitrobenzyl ether and 3.5 g of zinc powder in 300 ml of ethanol was heated to 70° C. A solution of 1.6 g of ammonium chloride in 20 ml of water was slowly dropped into the heated solution. After stirring at 70–80° C. for 5 hours, the reaction mixture was cooled to room temperature and then filtered. The filtrate was concentrated. After the extraction with ether, the organic layer was washed with water, dried over anhydrous magnesium sulfate and evaporated to obtain 4.8 g of N-[2-(3-methoxyimino-2,3-dihydrobenzofuran-6-yloxymethyl)-phenyl]-N-hydroxyamine. [$^1$H-NMR (CDCl$_3$)(ppm): 3.95 (3H, s), 5.07 (2H×2, s), 6.40–7.50 (m)]. The product wa subjected to the subsequent reaction without the purification.

ii) A solution of 4.8 g of N-[2-(3-methoxyimino-2,3-dihydro-benzofuran-6-yloxymethyl)phenyl]-N-hydroxyamine and 1.3 g of pyridine in 50 ml of dichloromethane was cooled to 0° C. 1.4 g of methyl chloroformate was dropped into the solution. The temperature was slowly elevated to room temperature, and the reaction was further carried out for 8 hours. After the completion of the reaction, the reaction liquid was washed with a dilute aqueous hydrochloric acid solution and aqueous NaCl solution and then dried over anhydrous magnesium sulfate. After the concentration under reduced pressure, the obtained residue was dissolved in a mixed solution of 30 ml of methanol and 20 ml of tetrahydrofuran. 1.4 g of anhydrous potassium carbonate was added to the obtained solution, and they were stirred for 4 hours. Water and diethyl ether were added to the reaction solution, and the resultant mixture was neutralized with a dilute aqueous hydrochloric acid solution. After the extraction with diethyl ether, the extract was dried over anhydrous magnesium sulfate and then concentrated under reduced pressure. The residue thus obtained was purified by the silica gel chromatography (hexane:ethyl acetate) to obtain 1.9 g of methyl N-[2-(3- methoxyimino-2,3-dihydrobenzofuran-6-yloxymethyl) phenyl]-N-hydroxycarbamate [$^1$H-NMR (CDCl$_3$) (ppm): 3.77 (3H, s), 3.93 (3H, s), 5.03 (2H, s), 5.13 (2H, s), 6.49–7.50 (m)].

iii) 1.1 g of methyl iodide and 0.88 g of anhydrous potassium carbonate were added to a solution of 1.9 g of methyl N-[2-(3-methoxyimino-2,3-dihydro-benzofuran-6-yloxymethyl)phenyl]-N-hydroxycarbamate in 20 ml of N,N-dimethylformamide, and they were stirred at room temperature for 24 hours. The reaction solution was diluted with 200 ml of diethyl ether, washed with water, dried over anhydrous magnesium sulfate and concentrated under reduced pressure. The residue was purified by the silica gel chromatography (hexane:ethyl acetate) to obtain 1.5 g of the title compound (having a m. p. of 102–103° C. and $^1$H-NMR data shown in the following table].

Synthesis Example 7

Synthesis of N-[2-(3-methoxyimino-2,3-dihydrobenzofuran-6-yloxymethyl)phenyl]-N-methoxy-N'-methylurea (a-8):

0.38 g of methyl isocyanate was added to a solution of 2.0 g of N-[2-(3-methoxyimino-2,3-dihydro-benzofuran-6-yloxymethyl)phenyl]-N-hydroxyamine in 50 ml of tetrahydrofuran, and they were stirred at room temperature for 8 hours. The reaction liquid was concentrated under reduced pressure to obtain 2.3 g of N-2-(3-methoxyimino-2,3-dihydro-benzofuran-6-yloxymethyl)phenyl]-N-hydroxy-N'-methylurea. This product was dissolved in 20 ml of N,N-dimethylformamide. 0.95 g of methyl iodide and 0.93 g of anhydrous potassium carbonate were added to the solution, and they were stirred at room temperature for 4 hours. The reaction solution was diluted with 200 ml of diethyl ether, washed with water, dried over anhydrous magnesium sulfate and concentrated under reduced pressure. The residue was purified by the silica gel chromatography (hexane:ethyl acetate) to obtain 1.4 g of the title compound (having a m.p. of 109–112° C. and $^1$H-NMR data shown in the following table].

Synthesis Example 8

Synthesis of (E) methyl 3-methoxy-2-(4-methoxyimino-chroman-7-yloxymethyl)-phenyl]-acrylate (c-2):

i) Synthesis of 4-methoxyimino-7-hydroxy-chroman (intermediate ia-8):

4.0 g of methoxyamine hydrochloride was added to a solution of 3.0 g of 4-oxo-7-hydroxy-chroman and 5.0 g of molecular sieves (3A) in 80 ml of methanol, and the reaction was carried out at room temperature for 16 hours. After the completion of the reaction, the reaction liquid was filtered and the filtrate was concentrated. The residue was poured into ice/water, and the solids thus formed were taken by the filtration, washed with water and dried to obtain 3.0 g of crystals [having a m. p. of 100–103° C. and $^1$H-NMR data shown in the following table].

ii) 0.456 g of 60% sodium hydride was added to 2.0 g of 4-methoxyimino-7-hydroxy-chroman in 30 ml of N,N-dimethylformamide, and they were stirred for 30 minutes. 3.54 g of (E) methyl 3-methoxy(2-bromomethylphenyl) acrylate was added to the solution, and the reaction was carried out at room temperature for 6 hours. After the completion of the reaction, the reaction solution was diluted with 200 ml of diethyl ether, washed with water, dried over anhydrous magnesium sulfate and concentrated under reduced pressure. The residue was purified by the silica gel chromatography (hexane:ethyl acetate) to obtain 2.8 g of the oily title compound (having $^1$H-NMR data shown in the following table].

Compounds of the present invention were produced in the same manner as that described above, and examples of them are shown in Tables 1 to 22 given below.

Further, examples of the resultant intermediates are also shown in Tables 23 and 24 given below.

TABLE 1

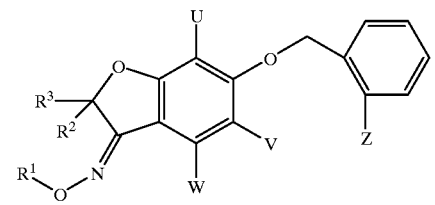

wherein R$^2$, R$^3$ and W each represent H, and the symbols in the table have the following meanings:
Za represents C(CO2CH3)=CHOCH3,
Zb represents C(CO$_2$CH$_3$)=CHCH$_3$,
Zc represents C(CO$_2$CH$_3$)=NOCH$_3$,
Zd represents C(CONHCH$_3$)=NOCH$_3$,
Ze represents C(CSNHCH$_3$)=NOCH$_3$,
Zf represents N(CO$_2$CH$_3$)OCH$_3$,
Zg represents N(CONHCH$_3$)OCH$_3$,
Zh represents N(CSNHCH$_3$)OCH$_3$,
Zi represents CH(CO$_2$CH$_3$)OCH$_3$,
Zj represents CH(CONHCH$_3$)OCH$_3$ or Zk represents CH(CSNHCH$_3$)OCH$_3$,
and the geometrical isomers of Za to Ze are E-isomers.).

| Compound No. | R$^1$ | U | V | Z | Properties (Temp.: m.p.) |
|---|---|---|---|---|---|
| a-1 | H | H | H | Zc | 80–83° C. |
| a-2 | CH$_3$ | H | H | Za | 92–94° C. |
| a-3 | CH$_3$ | H | H | Zb | |

TABLE 1-continued

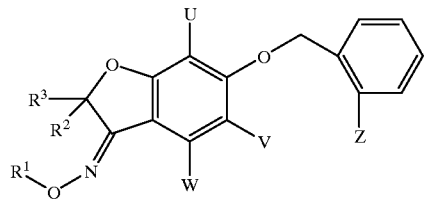

wherein R², R³ and W each represent H, and the symbols in the table have the following meanings:

Za represents C(CO2CH3)=CHOCH3,
Zb represents C(CO$_2$CH$_3$)=CHCH$_3$,
Zc represents C(CO$_2$CH$_3$)=NOCH$_3$,
Zd represents C(CONHCH$_3$)=NOCH$_3$,
Ze represents C(CSNHCH$_3$)=NOCH$_3$,
Zf represents N(CO$_2$CH$_3$)OCH$_3$,
Zg represents N(CONHCH$_3$)OCH$_3$,
Zh represents N(CSNHCH$_3$)OCH$_3$,
Zi represents CH(CO$_2$CH$_3$)OCH$_3$,
Zj represents CH(CONHCH$_3$)OCH$_3$ or Zk represents CH(CSNHCH$_3$)OCH$_3$,
and the geometrical isomers of Za to Ze are E-isomers.).

| Compound No. | R¹ | U | V | Z | Properties (Temp.: m.p.) |
|---|---|---|---|---|---|
| a-4 | CH$_3$ | H | H | Zc | 108–110° C. |
| a-5 | CH$_3$ | H | H | Zd | 143–145° C. |
| a-6 | CH$_3$ | H | H | Ze | |
| a-7 | CH$_3$ | H | H | Zf | 102–103° C. |
| a-8 | CH$_3$ | H | H | Zg | 109–112° C. |
| a-9 | CH$_3$ | H | H | Zh | |
| a-10 | CH$_3$ | H | H | Zi | |
| a-11 | CH$_3$ | H | H | Zj | 120–121° C. |
| a-12 | CH$_3$ | H | H | Zk | |
| a-13 | CH$_3$ | CH$_3$ | H | Za | 164–166° C. |
| a-14 | CH$_3$ | CH$_3$ | H | Zb | |
| a-15 | CH$_3$ | CH$_3$ | H | Zc | 125–130° C. |
| a-16 | CH$_3$ | CH$_3$ | H | Zd | 145–146° C. |
| a-17 | CH$_3$ | CH$_3$ | H | Ze | |
| a-18 | CH$_3$ | CH$_3$ | H | Zf | |
| a-19 | CH$_3$ | CH$_3$ | H | Zg | |
| a-20 | CH$_3$ | CH$_3$ | H | Zh | |
| a-21 | CH$_3$ | CH$_3$ | H | Zi | |
| a-22 | CH$_3$ | CH$_3$ | H | Zj | |
| a-23 | CH$_3$ | CH$_3$ | H | Zk | |
| a-24 | CH$_3$ | H | CH$_3$ | Za | |
| a-25 | CH$_3$ | H | CH$_3$ | Zb | |
| a-26 | CH$_3$ | H | CH$_3$ | Zc | 103–113° C. |
| a-27 | CH$_3$ | H | CH$_3$ | Zd | 140–155° C. |
| a-28 | CH$_3$ | H | CH$_3$ | Ze | |
| a-29 | CH$_3$ | H | CH$_2$CH$_3$ | Zc | 95–96° C. |
| a-30 | CH$_3$ | H | CH$_2$CH$_3$ | Zc | *1) crystals |
| a-31 | CH$_3$ | H | CH$_2$CH$_3$ | Zd | 146–147° C. |
| a-32 | CH$_3$ | H | CH$_2$CH$_3$ | Zd | *2) 170–171° C. |
| a-33 | CH$_3$ | H | Cl | Zj | |
| a-34 | CH$_3$ | H | OCH$_3$ | Zk | |
| a-35 | CH$_2$CH$_3$ | CH$_3$ | H | Zc | 104–110° C. |
| a-36 | CH$_2$CH$_3$ | CH$_3$ | H | Zd | 126–128° C. |
| a-37 | CH$_2$CH$_3$ | H | H | Zd | 110–113° C. |
| a-38 | CH$_2$CF$_3$ | CH$_3$ | H | Zc | |
| a-39 | CH$_2$OCH$_3$ | CH$_3$ | H | Zc | |
| a-40 | CH(CH$_3$)$_2$ | H | H | Zd | glassy |
| a-41 | CH$_2$CH$_2$CH$_3$ | CH$_3$ | H | Zc | |
| a-42 | CH$_2$CH$_2$CH$_3$ | CH$_3$ | H | Zd | 140–142° C. |
| a-43 | CH$_2$(CH$_2$)$_2$CH$_3$ | CH$_3$ | H | Zd | |
| a-44 | CH$_2$(CH$_2$)$_4$CH$_3$ | CH$_3$ | H | Zd | |
| a-45 | CH$_2$CH$_2$(OCH$_3$)$_2$ | CH$_3$ | H | Zd | |
| a-46 | CH$_2$CH$_2$(OCH$_2$CH$_3$)$_2$ | CH$_3$ | H | Zc | |
| a-47 | CH$_2$CH$_2$(OCH$_2$CH$_3$)$_2$ | CH$_3$ | H | Zd | |
| a-48 | CH$_2$CN | CH$_3$ | H | Zc | 135–139° C. |
| a-49 | CH$_2$CN | CH$_3$ | H | Zd | 160–165° C. |
| a-50 | CF$_2$H | CH$_3$ | H | Zd | |
| a-51 | CH$_2$(CH$_2$)$_3$Cl | CH$_3$ | H | Zd | |
| a-52 | C(CH$_3$)$_3$ | CH$_3$ | H | Zd | |
| a-53 | CH$_2$CO$_2$CH$_3$ | CH$_3$ | H | Zc | 104–107° C. |
| a-54 | CH$_2$CO$_2$CH$_3$ | CH$_3$ | H | Zd | 82–90° C. |
| a-55 | CH(CH$_3$)$_2$ | CH$_3$ | H | Zd | |

TABLE 1-continued

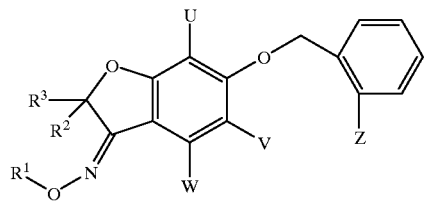

wherein $R^2$, $R^3$ and W each represent H, and the symbols in the table have the following meanings:
Za represents C(CO2CH3)=CHOCH3,
Zb represents $C(CO_2CH_3)$=CHCH$_3$,
Zc represents $C(CO_2CH_3)$=NOCH$_3$,
Zd represents C(CONHCH$_3$)=NOCH$_3$,
Ze represents C(CSNHCH$_3$)=NOCH$_3$,
Zf represents N(CO$_2$CH$_3$)OCH$_3$,
Zg represents N(CONHCH$_3$)OCH$_3$,
Zh represents N(CSNHCH$_3$)OCH$_3$,
Zi represents CH(CO$_2$CH$_3$)OCH$_3$,
Zj represents CH(CONHCH$_3$)OCH$_3$ or Zk represents CH(CSNHCH$_3$)OCH$_3$,
and the geometrical isomers of Za to Ze are E-isomers.).

| Compound No. | $R^1$ | U | V | Z | Properties (Temp.: m.p.) |
|---|---|---|---|---|---|
| a-56 | CH$_2$CH$_2$CH$_3$ | CH$_3$ | H | Zc | |
| a-57 | CH$_2$CH$_2$CH$_3$ | CH$_3$ | H | Zd | |
| a-58 | CH$_2$(CH$_2$)$_2$CH$_3$ | CH$_3$ | H | Zd | |
| a-59 | CH$_2$CH=CH$_2$ | CH$_3$ | H | Zc | 105–114° C. |
| a-60 | CH$_2$CH=CH$_2$ | CH$_3$ | H | Zd | 133–137° C. |
| a-61 | CH$_2$CH=CHCl(trans) | CH$_3$ | H | Zc | 110–115° C. |
| a-62 | CH$_2$CH=CHCl(trans) | CH$_3$ | H | Zd | 110–112° C. |
| a-63 | CH$_2$CH=CHCl(trans) | H | H | Zd | oily |
| a-64 | CH$_2$C(Cl)=CH$_2$ | CH$_3$ | H | Zd | 120–124° C. |
| a-65 | CH$_2$CH=CHCH$_3$(trans) | CH$_3$ | H | Zd | oily |
| a-66 | CH$_2$CH=C(CH$_3$)$_2$ | CH$_3$ | H | Zc | oily |
| a-67 | CH$_2$CH=C(CH$_3$)$_2$ | CH$_3$ | H | Zd | 67–74° C. |
| a-68 | CH$_2$CH=CCl$_2$ | CH$_3$ | H | Zc | |
| a-69 | CH$_2$CH=CCl$_2$ | CH$_3$ | H | Zd | |
| a-70 | CH$_2$C≡CH | CH$_3$ | H | Zc | 90–101° C. |
| a-71 | CH$_2$C≡CH | CH$_3$ | H | Zd | 145–157° C. |
| a-72 | CH$_2$C$_6$H$_5$ | CH$_3$ | H | Zc | 85–95° C. |
| a-73 | CH$_2$C$_6$H$_5$ | CH$_3$ | H | Zd | 138–141° C. |
| a-74 | CH$_2$—C$_6$H$_4$(4-Cl) | CH$_3$ | H | Zd | |
| a-75 | CH$_2$—C$_6$H$_4$(4-OCH$_3$) | CH$_3$ | H | Zd | |
| a-76 | CH$_2$—C$_6$H$_4$(4-C$_2$H$_6$) | CH$_3$ | H | Zd | |
| a-77 | CH$_2$—C$_6$H$_4$(4-CF$_3$) | CH$_3$ | H | Zd | |
| a-78 | CH$_2$—C$_6$H$_3$(3,4-Cl$_2$) | CH$_3$ | H | Zc | 160–165° C. |
| a-79 | CH$_2$—C$_6$H$_3$(3,4-Cl$_2$) | CH$_3$ | H | Zd | 172–173° C. |
| a-80 | CH$_2$—C$_6$H$_4$(3-F) | CH$_3$ | H | Zc | |
| a-81 | CH$_2$—C$_6$H$_4$(3-F) | CH$_3$ | H | Zd | |
| a-82 | CH$_2$—C$_6$F$_5$ | CH$_3$ | H | Zc | |
| a-83 | CH$_2$—C$_6$F$_5$ | CH$_3$ | H | Zd | |
| a-84 | H | CH$_3$ | H | Za | |
| a-85 | H | CH$_3$ | H | Zc | |
| a-86 | H | CH$_3$ | H | Zd | |
| a-87 | CH$_2$—C$_6$H$_4$(2-CN) | CH$_3$ | H | Zc | |
| a-88 | CH$_2$(1-naphthyl) | CH$_3$ | H | Zc | |
| a-89 | CH$_2$(1-naphthyl) | CH$_3$ | H | Zd | |
| a-90 | CH$_2$(2-naphthyl) | CH$_3$ | H | Zd | |

*1) Compound a-30 is a geometrical isomer of a-29 in >= NOR$^1$ part.
*2) Compound a-32 is a geometrical isomer of a-31 in >= NOR$^1$ part.

TABLE 2

(wherein R¹ represents CH₃, and V=W=H.)

| Compound No. | R² | R³ | U | Z | Properties (Temp.: m.p.) |
|---|---|---|---|---|---|
| b-1 | CH₃ | H | H | Za | |
| b-2 | CH₃ | H | H | Zb | |
| b-3 | CH₃ | H | H | Zc | |
| b-4 | CH₃ | H | CH₃ | Za | 59–62° C. |
| b-5 | CH₃ | H | CH₃ | Za | *1) 108–112° C. |
| b-6 | CH₃ | H | CH₃ | Zc | 85–100° C. |
| b-7 | CH₃ | H | CH₃ | Zd | 105–107° C. |

TABLE 2-continued (wherein R¹ represents CH₃, and V=W=H.)

| Compound No. | R² | R³ | U | Z | Properties (Temp.: m.p.) |
|---|---|---|---|---|---|
| b-8 | CH₂CH₃ | H | CH₃ | Za | |
| b-9 | CH₂CH₃ | H | CH₃ | Zb | |
| b-10 | CH₂CH₃ | H | CH₃ | Zc | |
| b-11 | CH₂CH₃ | H | CH₃ | Zd | |
| b-12 | CH₃ | CH₃ | CH₃ | Za | |
| b-13 | CH₃ | CH₃ | CH₃ | Zb | |
| b-14 | CH₃ | CH₃ | CH₃ | Zc | |
| b-15 | CH₃ | CH₃ | CH₃ | Zd | |
| b-16 | CH₃ | CH₃ | CH₃ | Ze | |
| b-17 | CH₃ | CH₃ | CH₃ | Zf | |

*1) Compound b-5 is a geometrical isomer of b-4 in >= NOR¹ part.

TABLE 3

(wherein R², R³, R⁴, R⁵ and W each represents H.)

| Compound No. | R¹ | U | V | Z | Properties (Temp.: m.p.) |
|---|---|---|---|---|---|
| c-1 | H | H | H | Za | |
| c-2 | CH₃ | H | H | Za | oily |
| c-3 | CH₃ | H | H | Zb | |
| c-4 | CH₃ | H | H | Zc | 124–125° C. |
| c-5 | CH₃ | H | H | Zd | 54–57° C. |
| c-6 | CH₃ | H | H | Ze | |
| c-7 | CH₃ | H | H | Zf | oily |
| c-8 | CH₃ | H | H | Zg | oily |
| c-9 | CH₃ | H | H | Zh | |
| c-10 | CH₃ | H | H | Zi | |
| c-11 | CH₃ | H | H | Zj | 60–65° C. |
| c-12 | CH₃ | H | H | Zk | |
| c-13 | CH₃ | CH₃ | H | Za | 88–91° C. |
| c-14 | CH₃ | CH₃ | H | Zb | |
| c-15 | CH₃ | CH₃ | H | Zc | 101–102° C. |
| c-16 | CH₃ | CH₃ | H | Zd | 127–129° C. |
| c-17 | CH₃ | CH₃ | H | Ze | |
| c-18 | CH₃ | CH₃ | H | Zf | |
| c-19 | CH₃ | CH₃ | H | Zg | |
| c-20 | CH₃ | CH₃ | H | Zh | |
| c-21 | CH₃ | CH₃ | H | Zi | |
| c-22 | CH₃ | CH₃ | H | Zj | |
| c-23 | CH₃ | CH₃ | H | Zk | |
| c-24 | CH₃ | H | CH₃ | Za | |
| c-25 | CH₃ | H | CH₃ | Zb | |
| c-26 | CH₃ | H | CH₃ | Zc | oily |
| c-27 | CH₃ | H | CH₃ | Zd | 116–117° C. |
| c-28 | CH₃ | H | CH₃ | Ze | |
| c-29 | CH₃ | CH₂CH₃ | H | Zc | 100–101° C. |
| c-30 | CH₃ | CH₂CH₃ | H | Zd | 148–150° C. |

TABLE 3-continued

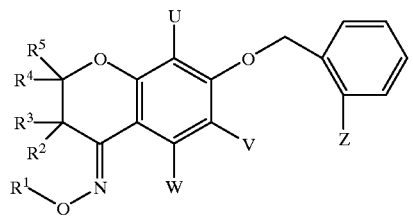

(wherein $R^2$, $R^3$, $R^4$, $R^5$ and W each represents H.)

| Compound No. | $R^1$ | U | V | Z | Properties (Temp.: m.p.) |
|---|---|---|---|---|---|
| c-31 | $CH_3$ | H | $CH_2CH_3$ | Zc | |
| c-32 | $CH_3$ | H | $CH_2CH_3$ | Zd | |
| c-33 | $CH_3$ | H | Cl | Zj | |
| c-34 | $CH_3$ | H | $OCH_3$ | Zk | |
| c-35 | $CH_2CH_3$ | $CH_3$ | H | Zc | |
| c-36 | $CH_2CH_3$ | $CH_3$ | H | Zd | |
| c-37 | $CH_2CH_3$ | H | H | Zd | |
| c-38 | $CH_2CF3$ | $CH_3$ | H | Zc | |
| c-39 | $CH_2OCH_3$ | $CH_3$ | H | Zc | |
| c-40 | $CH(CH_3)2$ | $CH_3$ | H | Zc | |
| c-41 | $CH_2CH_2CH_3$ | $CH_3$ | H | Zc | |
| c-42 | $CH_2CH_2CH_3$ | $CH_3$ | H | Zd | |
| c-43 | $CH_2(CH_2)_2CH_3$ | $CH_3$ | H | Zd | 106–108° C. |
| c-44 | $CH_2(CH_2)_4CH_3$ | $CH_3$ | H | Zd | |
| c-45 | $CH_2CH_2(OCH_3)_2$ | $CH_3$ | H | Zd | |
| c-46 | $CH_2CH_2(OCH_2CH_3)_2$ | $CH_3$ | H | Zc | 69–71° C. |
| c-47 | $CH_2CH_2(OCH_2CH_3)_2$ | $CH_3$ | H | Zd | |
| c-48 | $CH_2CN$ | $CH_3$ | H | Zc | 132–133° C. |
| c-49 | $CH_2CN$ | $CH_3$ | H | Zd | 156–157° C. |
| c-50 | $CF_2H$ | $CH_3$ | H | Zd | |
| c-51 | $CH_2(CH_2)_3Cl$ | $CH_3$ | H | Zd | |
| c-52 | $C(CH_3)_3$ | $CH_3$ | H | Zc | 115–117° C. |
| c-53 | $C(CH_3)_3$ | $CH_3$ | H | Zd | 64–67° C. |
| c-54 | $CH_2CO_2CH_3$ | $CH_3$ | H | Zd | |
| c-55 | $CH(CH_3)_2$ | $CH_3$ | H | Zd | |
| c-56 | $CH_2C(CH_3)_3$ | $CH_3$ | H | Zc | |
| c-57 | $CH_2C(CH_3)_3$ | $CH_3$ | H | Zd | |
| c-58 | $CH_2(CH_2)_2CH_3$ | $CH_3$ | H | Zd | 88–91° C. |
| c-59 | $CH_2CH=CH_2$ | $CH_3$ | H | Zc | |
| c-60 | $CH_2CH=CH_2$ | $CH_3$ | H | Zd | |
| c-61 | $CH_2CH=CHCl$ | $CH_3$ | H | Zc | 64–68° C. |
| c-62 | $CH_2CH=CHCl$ | $CH_3$ | H | Zd | 102–106° C. |
| c-63 | $CH_2CH=CHCl$ | H | H | Zc | 108–113° C. |
| c-64 | $CH_2C(Cl)=CHl$ | $CH_3$ | H | Zd | 108–110° C. |
| c-65 | $CH_2CH=CHCH_3$(trans) | $CH_3$ | H | Zd | |
| c-66 | $CH_2CH=C(CH_3)_2$ | $CH_3$ | H | Zc | |
| c-67 | $CH_2CH=C(CH_3)_2$ | $CH_3$ | H | Zd | 153–154° C. |
| c-68 | $CH_2CH=CCl_2$ | $CH_3$ | H | Zc | |
| c-69 | $CH_2CH=CCl_2$ | $CH_3$ | H | Zd | |
| c-70 | $CH_2C\equiv CH$ | $CH_3$ | H | Zc | |
| c-71 | $CH_2C\equiv CH$ | $CH_3$ | H | Zd | |
| c-72 | $CH_2C_6H_5$ | $CH_3$ | H | Zc | |
| c-73 | $CH_2C_6H_5$ | $CH_3$ | H | Zd | |
| c-74 | $CH_2-C_6H_4(4-Cl)$ | $CH_3$ | H | Zd | |
| c-75 | $CH_2-C_6H_4(4-OCH_3)$ | $CH_3$ | H | Zd | |
| c-76 | $CH_2-C_6H_4(4-C_2H_5)$ | $CH_3$ | H | Zd | |
| c-77 | $CH_2-C_6H_4(4-CF_3)$ | $CH_3$ | H | Zd | |
| c-78 | $CH_2-C_6H_3(3,4-Cl_2)$ | $CH_3$ | H | Zc | 125–126° C. |
| c-79 | $CH_2-C_6H_3(3,4-Cl_2)$ | $CH_3$ | H | Zd | 88–93° C. |
| c-80 | $CH_2-C_6H_4(3-F)$ | $CH_3$ | H | Zc | 74–80° C. |
| c-81 | $CH_2-C_6H_4(3-F)$ | $CH_3$ | H | Zd | 100–102° C. |
| c-82 | $CH_2-C_6F_6$ | $CH_3$ | H | Zc | 135–138° C. |
| c-83 | $CH_2-C_6F_5$ | $CH_3$ | H | Zd | 118–120° C. |
| c-84 | $CH_2-C_6H_4(2-CN)$ | $CH_3$ | H | Za | |
| c-85 | H | $CH_3$ | H | Za | |
| c-86 | H | $CH_3$ | H | Zc | |
| c-87 | H | $CH_3$ | H | Zd | |
| c-88 | $CH_2$(1-naphthyl) | $CH_3$ | H | Zc | oily |
| c-89 | $CH_2$(1-naphthyl) | $CH_3$ | H | Zd | 146–150° C. |
| c-90 | $CH_2$(2-naphthyl) | $CH_3$ | H | Zd | |

TABLE 4

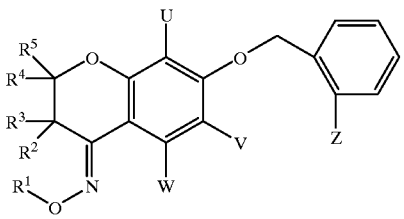

(wherein $R^1$ and U each represents $CH_3$, and V and W each represents H.)

| Compound No. | $R^2$ | $R^3$ | $R^4$ | $R^5$ | Z | Properties (Temp.: m.p.) |
|---|---|---|---|---|---|---|
| d-1 | $CH_3$ | H | H | H | Za | |
| d-2 | $CH_3$ | H | H | H | Zb | |
| d-3 | $CH_3$ | H | H | H | Zc | |
| d-4 | $CH_3$ | H | H | H | Zd | |
| d-5 | H | H | $CH_3$ | $CH_3$ | Za | |
| d-6 | H | H | $CH_3$ | $CH_3$ | Zc | 87–88° C. |
| d-7 | H | H | $CH_3$ | $CH_3$ | Zd | 162–163° C. |
| d-8 | H | H | $CH_3$ | H | Za | oily |
| d-9 | H | H | $CH_3$ | H | Zb | |

TABLE 4-continued

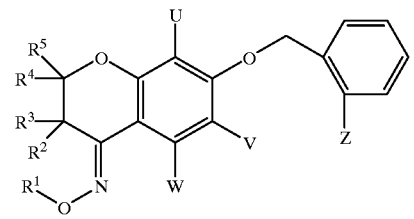

(wherein $R^1$ and U each represents $CH_3$, and V and W each represents H.)

| Compound No. | $R^2$ | $R^3$ | $R^4$ | $R^5$ | Z | Properties (Temp.: m.p.) |
|---|---|---|---|---|---|---|
| d-10 | H | H | $CH_3$ | H | Zc | 136–137° C. |
| d-11 | H | H | CH | H | Zd | 137–138° C. |
| d-12 | $CH_3$ | $CH_3$ | $CH_3$ | $CH_3$ | Za | |
| d-13 | $CH_3$ | $CH_3$ | $CH_3$ | $CH_3$ | Zb | |
| d-14 | $CH_2CH_3$ | $CH_3$ | $CH_3$ | $CH_3$ | Zc | |
| d-15 | $CH_2CH_3$ | $CH_3$ | $CH_3$ | H | Zd | |
| d-16 | H | H | $CH_2CH_3$ | H | Ze | |
| d-17 | H | H | $CH_2CH_3$ | H | Zf | |

TABLE 5

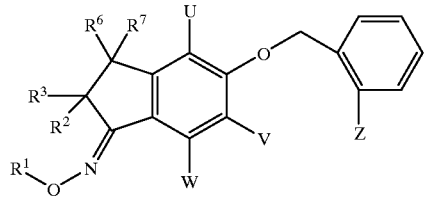

(wherein $R^2$, $R^3$, $R^6$ and $R^7$ each represents H.)

| Compound No. | $R^1$ | U | V | W | Z | Properties (Temp.: m.p.) |
|---|---|---|---|---|---|---|
| e-1 | H | H | H | H | Za | |
| e-2 | $CH_3$ | H | H | H | Za | |
| e-3 | $CH_3$ | H | H | H | Zb | |
| e-4 | $CH_3$ | H | H | H | Zc | |
| e-5 | $CH_3$ | H | H | H | Zd | glassy |
| e-6 | $CH_3$ | H | H | H | Ze | |
| e-7 | $CH_3$ | H | H | H | Zf | |
| e-8 | $CH_3$ | H | H | H | Zg | |
| e-9 | $CH_3$ | H | H | H | Zh | |
| e-10 | $CH_3$ | H | H | H | Zi | |
| e-11 | $CH_3$ | H | H | H | Zj | |
| e-12 | $CH_3$ | H | H | H | Zk | |
| e-13 | $CH_3$ | $CH_3$ | H | H | Za | |
| e-14 | $CH_3$ | $CH_3$ | H | H | Zb | |
| e-15 | $CH_3$ | $CH_3$ | H | H | Zc | 150–152° C. |
| e-16 | $CH_3$ | $CH_3$ | H | H | Zd | 132–133° C. |
| e-17 | $CH_3$ | $CH_3$ | H | H | Ze | |
| e-18 | $CH_3$ | $CH_3$ | H | H | Zf | |
| e-19 | $CH_3$ | $CH_3$ | H | H | Zg | |
| e-20 | $CH_3$ | $CH_3$ | H | H | Zh | |
| e-21 | $CH_3$ | $CH_3$ | H | H | Zi | |
| e-22 | $CH_3$ | $CH_3$ | H | $CH_3$ | Zc | 118–133° C. |
| e-23 | $CH_3$ | $CH_3$ | H | $CH_3$ | Zd | 157–161° C. |
| e-24 | $CH_3$ | H | $CH_3$ | H | Za | |
| e-25 | $CH_3$ | H | $CH_3$ | H | Zb | |
| e-26 | $CH_3$ | H | $CH_3$ | H | Zc | 110–112° C. |
| e-27 | $CH_3$ | H | $CH_3$ | H | Zd | 148–149° C. |
| e-28 | $CH_3$ | H | $CH_3$ | H | Za | |
| e-29 | $CH_3$ | $CH_2CH_3$ | H | H | Zb | |
| e-30 | $CH_3$ | $CH_2CH_3$ | H | H | Zc | |
| e-31 | $CH_3$ | H | $CH_2CH_3$ | H | Zd | |

TABLE 5-continued

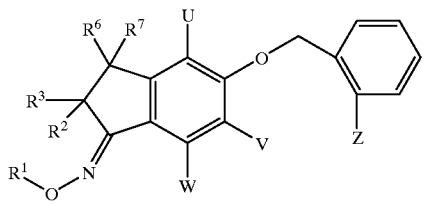

(wherein $R^2$, $R^3$, $R^6$ and $R^7$ each represents H.)

| Compound No. | $R^1$ | U | V | W | Z | Properties (Temp.: m.p.) |
|---|---|---|---|---|---|---|
| e-32 | CH$_3$ | H | CH$_2$CH$_3$ | H | Za | |
| e-33 | CH$_3$ | H | Cl | H | Zb | |
| e-34 | CH$_3$ | H | OCH$_3$ | H | Zc | |
| e-35 | CH$_2$CH$_3$ | H | H | H | Zd | |
| e-36 | CH$_2$CH$_3$ | CH$_3$ | H | H | Za | |
| e-37 | CH$_2$CF$_3$ | CH$_3$ | H | H | Zc | |
| e-38 | CH$_2$OCH$_3$ | CH$_3$ | H | H | Zd | |
| e-39 | CH(CH$_3$)$_2$ | CH$_3$ | H | H | Za | |
| e-40 | CH$_2$CH$_2$CH$_3$ | CH$_3$ | H | H | Zb | |
| e-41 | CH$_2$CH$_2$CH$_3$ | CH$_3$ | H | H | Zc | |
| e-42 | CH$_2$(CH$_2$)$_2$CH$_3$ | CH$_3$ | H | H | Zd | |
| e-43 | CH$_2$(CH$_2$)$_4$CH$_3$ | CH$_3$ | H | H | Za | |
| e-44 | CH$_2$CH$_2$O(CH$_3$)$_2$ | CH$_3$ | H | H | Zb | |
| e-45 | CH$_2$CH$_2$O(CH$_2$CH$_3$)$_2$ | CH$_3$ | H | H | Zc | |
| e-46 | CH$_2$CH$_2$O(CH$_2$CH$_3$)$_2$ | CH$_3$ | H | H | Zd | |
| e-47 | CH$_2$CN | CH$_3$ | H | H | Za | |
| e-48 | CH$_2$CN | CH$_3$ | H | H | Zb | |
| e-49 | CF$_2$H | CH$_3$ | H | H | Zc | |
| e-50 | CH$_2$(CH$_2$)$_3$Cl | CH$_3$ | H | H | Zd | |
| e-51 | C(CH$_3$)$_3$ | CH$_3$ | H | H | Za | |
| e-52 | CH$_2$CO$_2$CH$_3$ | CH$_3$ | H | H | Zc | |
| e-53 | CH(CH$_3$)$_2$ | CH$_3$ | H | H | Zd | |
| e-54 | CH$_2$C(CH$_3$)$_3$ | CH$_3$ | H | H | Za | |
| e-55 | CH$_2$CH=CH$_2$ | CH$_3$ | H | H | Za | |
| e-56 | CH$_2$CH=CHCl(trans) | CH$_3$ | H | CH$_3$ | Zd | 158–159° C. |
| e-57 | CH$_2$CH=CHCl(trans) | CH$_3$ | H | H | Zc | 130–134° C. |
| e-58 | CH$_2$CH=CHCl(trans) | H | H | H | Zd | 128–129° C. |
| e-59 | CH$_2$C≡CH | CH$_3$ | H | CH$_3$ | Zd | 164–165° C. |
| e-60 | CH$_2$C≡CH | CH$_3$ | H | H | Zc | 130–136° C. |
| e-61 | CH$_2$C≡CH | CH$_3$ | H | H | Zd | 166–168° C. |
| e-62 | CH$_2$C$_6$H$_6$ | CH$_3$ | H | H | Zb | |
| e-63 | CH$_2$—C$_6$H$_4$(4-Cl) | CH$_3$ | H | H | Zc | |
| e-64 | CH$_2$—C$_6$H$_4$(4-OCH$_3$) | CH$_3$ | H | H | Zd | |
| e-65 | CH$_2$—C$_6$H$_4$(4-C$_2$H$_5$) | CH$_3$ | H | H | Za | |
| e-66 | CH$_2$—C$_6$H$_4$(4-CF$_3$) | CH$_3$ | H | H | Zb | |

TABLE 6

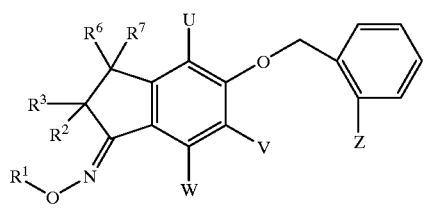

(wherein $R^1$ represents CH$_3$ and W represents H.)

| Compound No. | $R^2$ | $R^3$ | $R^6$ | $R^7$ | U | V | Z | Properties (Temp.: m.p.) |
|---|---|---|---|---|---|---|---|---|
| f-1 | CH$_3$ | H | H | H | H | H | Za | |
| f-2 | CH$_3$ | H | H | H | H | H | Zb | |
| f-3 | CH$_3$ | H | H | H | CH$_3$ | H | Zc | |
| f-4 | CH$_3$ | H | H | H | CH$_3$ | H | Zd | oily |
| f-5 | H | H | H | CH$_3$ | CH$_3$ | H | Za | 93–94° C. |
| f-6 | H | H | CH$_3$ | CH$_3$ | H | H | Zc | |
| f-7 | H | H | CH$_3$ | CH$_3$ | H | H | Zd | |
| f-8 | CH$_3$ | H | CH$_3$ | H | H | CH$_3$ | Za | |
| f-9 | CH$_3$ | H | H | H | H | CH$_3$ | Zc | oily |

TABLE 6-continued

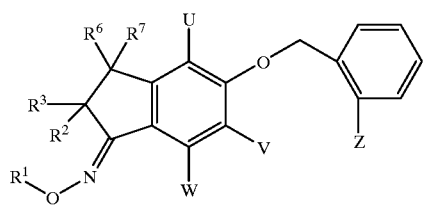

(wherein $R^1$ represents $CH_3$ and W represents H.)

| Compound No. | $R^2$ | $R^3$ | $R^6$ | $R^7$ | U | V | Z | Properties (Temp.: m.p.) |
|---|---|---|---|---|---|---|---|---|
| f-10 | $CH_3$ | H | H | H | H | $CH_3$ | Zc | *1) oily |
| f-11 | $CH_3$ | H | H | H | H | $CH_3$ | Zd | *2) 108–110° C. |
| f-12 | $CH_3$ | H | H | H | H | $CH_3$ | Zd | 89–90° C. |
| f-13 | $CH_3$ | $CH_3$ | $CH_3$ | $CH_3$ | H | H | Zb | |
| f-14 | $CH_2CH_3$ | $CH_3$ | $CH_3$ | $CH_3$ | H | H | Zc | |
| f-15 | $CH_2CH_3$ | $CH_3$ | $CH_3$ | H | H | H | Zd | |
| f-16 | H | H | $CH_2CH_3$ | H | H | H | Ze | |
| f-17 | H | H | $CH_2CH_3$ | H | H | H | Zf | |

*1) Compound f-10 is a geometrical isomer of f-9 in $\geq$ $NOR^1$ part.
*2) Compound f-12 is a geometrical isomer of f-11 in $\geq$ $NOR^1$ part.

TABLE 7

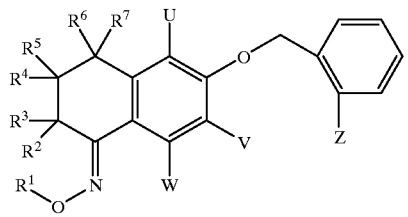

(wherein $R^2$, $R^3$, $R^4$, $R^5$, $R^6$ and $R^7$ each represents H.)

| Compound No. | $R^1$ | U | V | W | Z | Properties (Temp.: m.p.) |
|---|---|---|---|---|---|---|
| g-1 | H | H | H | H | Za | |
| g-2 | $CH_3$ | H | H | H | Za | |
| g-3 | $CH_3$ | H | H | H | Zb | |
| g-4 | $CH_3$ | H | H | H | Zc | 114–115° C. |
| g-5 | $CH_3$ | H | H | H | Zd | oily |
| g-6 | $CH_3$ | H | H | H | Ze | |
| g-7 | $CH_3$ | H | H | H | Zf | |
| g-8 | $CH_3$ | H | H | H | Zg | |
| g-9 | $CH_3$ | H | H | H | Zh | |
| g-10 | $CH_3$ | H | H | H | Zi | |
| g-11 | $CH_3$ | H | H | H | Zj | |
| g-12 | $CH_3$ | H | H | H | Zk | |
| g-13 | $CH_3$ | $CH_3$ | H | H | Za | oily |
| g-14 | $CH_3$ | $CH_3$ | H | H | Zb | |
| g-15 | $CH_3$ | $CH_3$ | H | H | Zc | 134–135° C. |
| g-16 | $CH_3$ | $CH_3$ | H | H | Zd | 120–121° C. |
| g-17 | $CH_3$ | $H_3$ | H | H | Ze | |
| g-18 | $CH_3$ | $CH_3$ | H | H | Zf | |
| g-19 | $CH_3$ | $CH_3$ | H | H | Zg | |
| g-20 | $CH_3$ | $CH_3$ | H | H | Zh | |
| g-21 | $CH_3$ | $CH_3$ | H | H | Zi | |
| g-22 | $CH_3$ | $CH_3$ | H | H | Zj | |
| g-23 | $CH_3$ | $CH_3$ | H | H | Zk | |
| g-24 | $CH_3$ | H | $CH_3$ | H | Za | 70–75° C. |
| g-25 | $CH_3$ | H | $CH_3$ | H | Zb | |
| g-26 | $CH_3$ | H | $CH_3$ | H | Zc | 107–110° C. |
| g-27 | $CH_3$ | H | $CH_3$ | H | Zd | 132–133° C. |
| g-28 | $CH_3$ | H | $CH_3$ | H | Za | |
| g-29 | $CH_3$ | $CH_2CH_3$ | H | H | Zb | |
| g-30 | $CH_3$ | $CH_2CH_3$ | H | H | Zc | |
| g-31 | $CH_3$ | H | $CH_2CH_3$ | H | Zd | |
| g-32 | $CH_3$ | H | $CH_2CH_3$ | H | Za | |
| g-33 | $CH_3$ | H | Cl | H | Zb | |

TABLE 7-continued

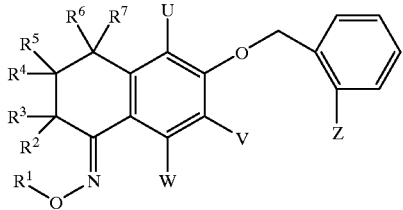

(wherein $R^2$, $R^3$, $R^4$, $R^5$, $R^6$ and $R^7$ each represents H.)

| Compound No. | $R^1$ | U | V | W | Z | Properties (Temp.: m.p.) |
|---|---|---|---|---|---|---|
| g-34 | $CH_3$ | H | $OCH_3$ | H | Zc | |
| g-35 | $CH_2CH_3$ | $CH_3$ | H | H | Zd | |
| g-36 | $CH_2CH_3$ | $CH_3$ | H | H | Za | |
| g-37 | $CH_2CH_3$ | H | H | H | Zb | |
| g-38 | $CH_2CF_3$ | $CH_3$ | H | H | Zc | |
| g-39 | $CH_2OCH_3$ | $CH_3$ | H | H | Zd | |
| g-40 | $CH(CH_3)_2$ | $CH_3$ | H | H | Za | |
| g-41 | $CH_2CH_2CH_3$ | $CH_3$ | H | H | Zb | |
| g-42 | $CH_2CH_2CH_3$ | $CH_3$ | H | H | Zc | |
| g-43 | $CH_2(CH_2)_2CH_3$ | $CH_3$ | H | H | Zd | |
| g-44 | $CH_2(CH_2)_4CH_3$ | $CH_3$ | H | H | Za | |
| g-45 | $CH_2CH_2O(CH_3)_2$ | $CH_3$ | H | H | Zb | |
| g-46 | $CH_2CH_2O(CH_2CH_3)_2$ | $CH_3$ | H | H | Zc | |
| g-47 | $CH_2CH_2O(CH_2CH_3)_2$ | $CH_3$ | H | H | Zd | |
| g-48 | $CH_2CN$ | $CH_3$ | H | H | Za | |
| g-49 | $CH_2CN$ | $CH_3$ | H | H | Zb | |
| g-50 | $CF_2H$ | $CH_3$ | H | H | Zc | |
| g-51 | $CH_2(CH_2)_3Cl$ | $CH_3$ | H | H | Zd | |
| g-52 | $C(CH_3)_3$ | $CH_3$ | H | H | Za | |
| g-53 | $C(CH_3)_3$ | $CH_3$ | H | H | Zb | |
| g-54 | $CH_2CO_2CH_3$ | $CH_3$ | H | H | Zc | |
| g-55 | $CH(CH_3)_2$ | $CH_3$ | H | H | Zd | |
| g-56 | $CH_2Si(CH_3)_3$ | $CH_3$ | H | H | Za | |
| g-57 | $CH_2CH=CH_2$ | $CH_3$ | H | H | Za | |
| g-58 | $CH_2CH=CHCl$(trans) | $CH_3$ | H | H | Zc | 58–60° C. |
| g-59 | $CH_2CH=CHCl$(trans) | H | H | H | Zd | 102–103° C. |
| g-60 | $CH_2C\equiv CH$ | $CH_3$ | H | H | Zc | 137–140° C. |
| g-61 | $CH_2C\equiv CH$ | $CH_3$ | H | H | Zd | 143–144° C. |
| g-62 | $CH_2C_6H_5$ | $CH_3$ | H | H | Za | |
| g-63 | $CH_2-C_6H_4(4\text{-}Cl)$ | $CH_3$ | H | H | Zc | |
| g-64 | $CH_2-C_6H_4(4\text{-}OCH_3)$ | $CH_3$ | H | H | Zd | |
| g-65 | $CH_2-C_6H_4(4\text{-}C_2H_5)$ | $CH_3$ | H | H | Za | |
| g-66 | $CH_2-C_6H_4(4\text{-}CF_3)$ | $CH_3$ | H | H | Zb | |

TABLE 8

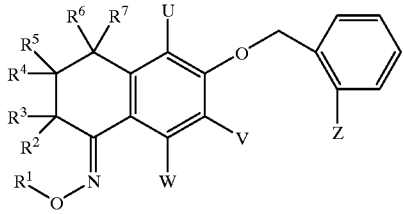

(wherein $R^1$ represents $CH_3$, and $R^4$, $R^5$ and W each represents H.)

| Compound No. | $R^2$ | $R^3$ | $R^6$ | $R^7$ | U | V | Z | Properties (Temp.: m.p.) |
|---|---|---|---|---|---|---|---|---|
| h-1 | $CH_3$ | H | H | H | $CH_3$ | H | Za | oily |
| h-2 | $CH_3$ | H | H | H | $CH_3$ | H | Zb | |
| h-3 | $CH_3$ | H | H | H | $CH_3$ | H | Zc | 99–102° C. |
| h-4 | $CH_3$ | H | H | H | $CH_3$ | H | Zd | 133–134° C. |
| h-5 | H | H | $CH_3$ | $CH_3$ | $CH_3$ | H | Za | |
| h-6 | H | H | $CH_3$ | $CH_3$ | $CH_3$ | H | Zc | |
| h-7 | H | H | $CH_3$ | $CH_3$ | $CH_3$ | H | Zd | |
| h-8 | H | H | $CH_3$ | H | H | H | Za | |
| h-9 | H | H | $CH_3$ | H | H | H | Zb | |

TABLE 8-continued

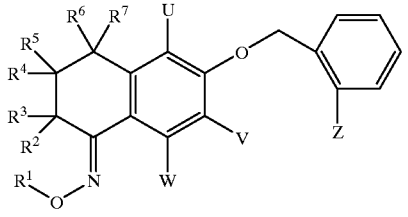

(wherein $R^1$ represents $CH_3$, and $R^4$, $R^5$ and W each represents H.)

| Compound No. | $R^2$ | $R^3$ | $R^6$ | $R^7$ | U | V | Z | Properties (Temp.: m.p.) |
|---|---|---|---|---|---|---|---|---|
| h-10 | H | H | $CH_3$ | H | H | H | Zc | |
| h-11 | H | H | $CH_3$ | H | H | H | Zd | |
| h-12 | $CH_3$ | $CH_3$ | $CH_3$ | $CH_3$ | H | $CH_3$ | Za | |
| h-13 | $CH_3$ | $CH_3$ | $CH_3$ | $CH_3$ | H | $CH_3$ | Zb | |
| h-14 | $CH_2CH_3$ | $CH_3$ | $CH_3$ | $CH_3$ | H | $CH_3$ | Zc | |
| h-15 | $CH_2CH_3$ | $CH_3$ | $CH_3$ | H | H | $CH_3$ | Zd | |
| h-16 | H | H | $CH_2CH_3$ | H | H | $CH_3$ | Ze | |
| h-17 | H | H | $CH_2CH_3$ | H | H | $CH_3$ | Zf | |
| h-18 | $CH_3$ | H | H | H | H | $CH_3$ | Zc | oily |
| h-19 | $CH_3$ | H | H | H | H | $CH_3$ | Zd | 100–105° C. |

TABLE 9

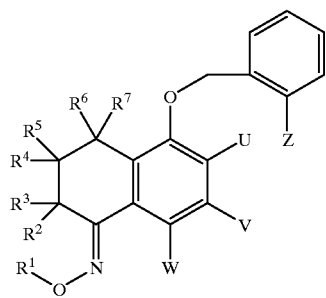

(wherein $R^2$, $R^3$, $R^4$, $R^5$, $R^6$ and $R^7$ each represents H.)

| Compound No. | $R^1$ | U | V | W | Z | Properties (Temp.: m.p.) |
|---|---|---|---|---|---|---|
| i-1 | H | H | H | H | Za | |
| i-2 | $CH_3$ | H | H | H | Za | |
| i-3 | $CH_3$ | H | H | H | Zb | |
| i-4 | $CH_3$ | H | H | H | Zc | 72–74° C. |
| i-5 | $CH_3$ | H | H | H | Zd | 155–157° C. |
| i-6 | $CH_3$ | H | H | H | Ze | |
| i-7 | $CH_3$ | H | H | H | Zf | |
| i-8 | $CH_3$ | H | H | H | Zg | |
| i-9 | $CH_3$ | H | H | H | Zh | |
| i-10 | $CH_3$ | H | H | H | Zi | |
| i-11 | $CH_3$ | H | $CH_3$ | H | Zj | |
| i-12 | $CH_3$ | H | H | $CH_3$ | Zk | |

TABLE 10

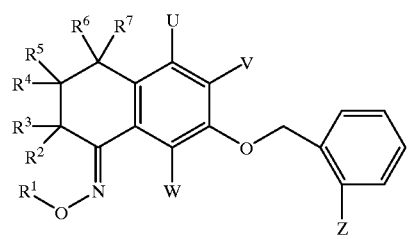

(wherein $R^2$, $R^3$, $R^4$, $R^5$, $R^6$ and $R^7$ each represents H.)

| Compound No. | $R^1$ | U | V | W | Z | Properties (Temp.: m.p.) |
|---|---|---|---|---|---|---|
| j-1 | H | H | H | H | Za | |
| j-2 | $CH_3$ | H | H | H | Za | |
| j-3 | $CH_3$ | H | H | H | Zb | |
| j-4 | $CH_3$ | H | H | H | Zc | crystal |
| j-5 | $CH_3$ | H | H | H | Zd | 86–87° C. |
| j-6 | $CH_3$ | H | H | H | Ze | |
| j-7 | $CH_3$ | H | H | H | Zf | |
| j-8 | $CH_3$ | H | H | H | Zg | |
| j-9 | $CH_3$ | H | H | H | Zh | |
| j-10 | $CH_3$ | H | H | H | Zi | |
| j-11 | $CH_3$ | $CH_3$ | H | H | Zj | |
| j-12 | $CH_3$ | H | $CH_3$ | H | Zk | |

TABLE 11

(wherein W, $R^2$, $R^3$, $R^4$ and $R^5$ each represents H, and $R^1$ represents $CH_3$.)

| Compound No. | A | n | U | V | Z | Properties (Temp.: m.p.) |
|---|---|---|---|---|---|---|
| k-1 | O | 2 | $CH_3$ | H | Za | 117–118° C. |
| k-2 | O | 2 | $CH_3$ | H | Zb | |
| k-3 | O | 2 | $CH_3$ | H | Zc | 134–136° C. |
| k-4 | O | 2 | $CH_3$ | H | Zd | 124–125° C. |
| k-5 | S | 1 | H | $CH_3$ | Za | 120–123° C. |
| k-6 | S | 1 | H | $CH_3$ | Zc | 116–118° C. |

TABLE 11-continued (wherein W, $R^2$, $R^3$, $R^4$ and $R^5$ each represents H, and $R^1$ represents $CH_3$.)

| Compound No. | A | n | U | V | Z | Properties (Temp.: m.p.) |
|---|---|---|---|---|---|---|
| k-7 | S | 1 | H | $CH_3$ | Zd | 147–148° C. |
| k-8 | S | 1 | $CH_3$ | H | Za | |
| k-9 | S | 1 | $CH_3$ | H | Zc | |
| k-10 | S | 1 | $CH_3$ | H | Zd | |
| k-11 | S | 1 | H | H | Za | |
| k-12 | S | 0 | H | H | Zb | |
| k-13 | S | 1 | H | H | Zc | |

TABLE 12

| Compound No. | 1H-NMR (CDCl$_3$) (ppm) |
|---|---|
| a-1 | 2.85(3H, s), 3.89(3H, s), 4.56(1H, s), 4.93(2H, s), 5.13(2H, s), 6.40–6.80(2H, s), 7.20–7.60(5H, m) |
| a-2 | 3.70(3H, s), 3.81(3H, s), 3.95(3H, s), 4.98(2H, s), 5.05(2H, s), 6.42–6.65(2H, m), 7.18–7.58(6H, m) |
| a-4 | 3.86(3H, s), 3.95(3H, s), 4.03(3H, s), 4.97(2H, s), 5.07(2H, s), 6.40–6.70(2H, m), 7.20–7.60(5H, m) |
| a-5 | 2.83(3H, d), 3.93(3H, s), 3.94(3H, s), 4.96(2H, s), 5.07(2H, s), 6.40–6.80(2H, m), 7.20–7.70(5H, m) |
| a-7 | 3.77(3H, s), 3.82(3H, s), 3.97(3H, s), 5.09(2H, s), 5.14(2H, s), 6.51–7.53(7H, m) |
| a-8 | 2.91(3H, d), 3.70(3H, s), 3.97(3H, s), 5.09(2H, s), 5.20(2H, s), 6.20(1H, bs), 6.57–7.50(7H, m) |
| a-11 | 2.81(3H, d), 3.36(3H, s), 3.96(3H, s), 4.96(1H, s), 5.08(2H, s), 5.29(2H, ABq), 6.55–7.55(8H, m) |
| a-13 | 2.12(3H, s), 3.69(3H, s), 3.80(3H, s), 3.92(3H, s), 4.99(2H, s), 5.03(2H, s), 6.44(1H, d), 7.19–7.54(5H, m) |
| a-15 | 2.11(3H, s), 3.82(3H, s), 3.93(3H, s), 4.01(3H, s), 4.97(2H, s), 5.07(2H, s), 6.49–7.46(6H, m) |
| a-16 | 2.10(3H, s), 2.87(3H, d), 3.93(3H, s), 3.94(3H, s), 4.98(2H, s), 5.08(2H, s), 6.41–7.45(7H, m) |
| a-26 | 2.18(3H, s), 3.82(3H, s), 3.94(3H, s), 4.02(3H, s), 4.96(2H, s), 5.01(2H, s), 6.38(1H, s), 7.25–7.47(5H, m) |
| a-27 | 2.17(3H, s), 2.87(3H, d), 3.93(3H×2, s), 4.94(2H, s), 5.01(2H, s), 6.40–7.45(7H, m) |
| a-29 | 1.19(3H, t), 2.60(2H, q), 3.82(3H, s), 3.92(3H, s), 4.03(3H, s), 4.92(2H, s), 5.01(2H, s), 6.36(1H, s), 7.21–7.43(5H, m) |
| a-30 | 1.18(3H, t), 2.62(2H, q), 3.82(3H, s), 3.98(3H, s), 4.02(3H, s), 4.96(2H×2, s), 6.35(1H, s), 7.33–7.79(5H, m) |
| a-31 | 1.18(3H, t), 2.62(2H, q), 2.88(3H, d), 3.93(3H×2, s), 4.93(2H, s), 5.01(2H, s), 6.41–7.45(7H, m) |
| a-32 | 1.16(3H, t), 2.59(2H, q), 2.88(3H, d), 3.93(3H, s), 3.96(3H, s), 4.95(2H×2, s), 6.39–7.79(7H, m) |
| a-35 | 1.29(3H, t), 2.11(3H, s), 3.81(3H, s), 4.00(3H, s), 4.17(2H, q), 4.45(2H, s), 5.06(2H, s), 6.45(1H, d), 7.20–7.45(5H, m) |
| a-36 | 1.29(3H, t), 2.10(3H, s), 2.87(3H, d), 3.91(3H, s), 4.17(2H, q), 4.94(2H, s), 5.05(2H, s), 6.40–7.49(7H, m) |
| a-37 | 1.25(3H, t), 2.85(3H, d), 3.88(3H, s), 4.15(2H, q), 4.91(2H, s), 5.05(2H, s), 6.40–6.80(2H, m), 7.20–7.60(5H, m) |
| a-40 | 1.30(6H, d), 1.78(1H, bs), 2.85(3H, d), 3.91(3H, s), 4.95(2H, s), 5.07(2H, s), 6.45–6.80(2H, m), 7.25–7.70(5H, m) |
| a-42 | 0.93(3H, t), 1.43–1.89(2H, m), 2.10(3H, s), 2.86(3H, d), 3.92(3H, s), 4.08(2H, t), 4.96(2H, s), 5.07(2H, s), 6.40–7.50(7H, m) |

TABLE 12-continued

| Compound No. | 1H-NMR (CDCl₃) (ppm) |
|---|---|
| a-48 | 2.11(3H, s), 3.82(3H, s), 4.02(3H, s), 4.76(2H, s), 4.99(2H, s), 5.08(2H, s), 6.50(1H, d), 7.28–7.51(5H, m) |
| a-49 | 2.10(3H, s), 2.89(3H, d), 3.95(3H, s), 4.76(2H, s), 5.00(2H, s), 5.08(2H, s), 6.50(1H, d), 6.70–6.85(1H, m), 7.29–7.50(5H, m) |
| a-53 | 2.10(3H, s), 3.75(3H, s), 3.80(3H, s), 4.01(3H, s), 4.68(2H, s), 4.98(2H, s), 5.17(2H, s), 6.42(1H, d), 7.20–7.51(5H, m) |
| a-54 | 2.10(3H, s), 2.84(3H, d), 3.79(3H, s), 3.91(3H, s), 4.68(2H, s), 4.98(2H, s), 5.19(2H, s), 6.43(1H, d), 6.71–6.83(1H, m), 7.20–7.50(5H, m) |
| a-59 | 2.11(3H, s), 3.82(3H, s), 4.02(3H, s), 4.63(2H, d), 4.96(2H, s), 5.10(2H, s), 5.35(2H, d), 5.65–5.15(1H, m), 6.45(1H, d), 7.20–7.45(5H, m) |
| a-60 | 2.10(3H, s), 2.86(3H, d), 3.91(3H, s), 4.61(2H, d), 4.95(2H, s), 5.09(2H, s), 5.60(2H, d), 5.72–6.15(1H, m), 6.41–7.50(7H, m) |
| a-61 | 2.11(3H, s), 3.81(3H, s), 4.01(3H, s), 4.57(2H, d), 4.96(2H, s), 5.04(2H, s), 6.09–6.33(2H, m), 6.46(1H, d), 7.20–7.45(4H, m) |
| a-62 | 2.10(3H, s), 2.87(3H, d), 3.92(3H, s), 4.57(2H, d), 4.97(2H, s), 5.05(2H, s), 6.10–6.85(4H, m), 7.13–7.50(5H, m) |
| a-63 | 2.85(3H, s), 3.89(3H, s), 4.55(2H, d), 4.89(2H, s), 5.03(2H, s), 6.00–6.30(2H, m) 6.40–6.70(2H, m), 7.20–7.60(5H, m) |
| a-64 | 2.09(3H, s), 2.90(3H, d), 3.91(3H, s), 4.65(2H, d), 4.96(2H, s), 5.11(2H, s), 5.38(2H, s), 6.51(1H, d), 6.71–6.84(1H, m), 7.25–7.49(5H, m) |
| a-65 | 1.80(3H, d), 2.12(3H, s), 2.89(3H, d), 3.95(3H, s), 4.60(2H, d), 5.00(2H, s), 5.10(2H, s), 5.61–5.92(2H, m), 6.52(1H, d), 6.70–6.85(1H, m), 7.11–7.65(5H, m) |
| a-66 | 1.75(3H×2, s), 2.09(3H, s), 3.80(3H, s), 4.00(3H, s), 4.62(2H, d), 4.96(2H, s), 5.07(2H, s), 5.45(1H, t), 6.45(1H, d), 7.25–7.50(5H, m) |
| a-67 | 1.75(3H×2, s), 2.08(3H, s), 2.88(3H, d), 3.93(3H, s), 4.62(2H, d), 4.95(2H, s), 5.06(2H, s), 5.45(1H, t), 6.48(1H, d), 6.71–6.85(1H, m), 7.25–7.49(5H, m) |
| a-70 | 2.10(3H, s), 2.48(1H, t), 3.80(3H, s), 4.00(3H, s), 4.70(2H, d), 4.98(2H, s), 5.09(2H, s), 6.46(1H, d), 7.20–7.46(5H, m) |
| a-71 | 2.10(3H, s), 2.47(1H, t), 2.87(3H, d), 3.92(3H, s), 4.21(2H, d), 4.98(2H, s), 5.09(2H, s), 6.42–7.44(7H, m) |
| a-72 | 2.10(3H, s), 3.81(3H, s), 4.02(3H, s), 4.97(2H, s), 5.10(2H, s), 5.18(2H, s), 6.42(1H, d), 7.20–7.49(10H, m) |
| a-73 | 2.09(3H, s), 2.89(3H, d), 3.94(3H, s), 4.97(2H, s), 5.10(2H, s), 5.18(2H, s), 6.50(1H, d), 6.69–6.82(1H, m), 7.20–7.50(10H, m) |
| a-78 | 2.10(3H, s), 3.82(3H, s), 4.01(3H, s), 4.98(2H, s), 5.09(2H×2, s), 6.45(1H, d), 7.20–7.49(8H, m) |
| a-79 | 2.09(3H, s), 2.89(3H, d), 3.94(3H, s), 4.99(2H, s), 5.10(2H×2, s), 6.50(1H, d), 6.69–6.82(1H, m), 7.25–7.51(8H, m) |

TABLE 13

| Compound No. | 1H-NMR (CdCl₃) (ppm) |
|---|---|
| b-4 | 1.54(3H, d), 2.11(3H, s), 3.68(3H, s), 3.86(3H, s), 3.92(3H, s), 4.99(2H, s), 5.15(1H, q), 6.40(1H, d), 7.20–7.85(6H, m) |
| b-5 | 1.54(3H, d), 2.11(3H, s), 3.68(3H, s), 3.78(3H, s), 3.89(3H, s), 4.98(2H, s), 6.42(1H, d), 6.85–7.68(6H, m) |
| b-6 | 1.54(3H, d), 2.08(3H, s), 3.80(3H, s), 3.99(3H, s), 4.96(2H, s), 5.27(TH, q), 6.38(1H, d), 7.20–7.85(5H, m) |
| b-7 | 1.56(3H, d), 2.09(3H, s), 2.87(3H, d), 3.92(3H×2, s), 4.98(2H, s), 5.27(1H, q), 6.35–6.85(2H, m), 7.21–7.85(5H, m) |

TABLE 14

| Compound No. | 1H-NMR (CDCl₃) (ppm) |
|---|---|
| c-2 | 2.83(2H, t), 3.70(3H, s), 3.79(3H, s), 3.94(3H, s), 4.16(2H, t), 4.92(2H, s), 6.35–7.83(8H, m) |
| c-4 | 2.79(2H, t), 3.80(3H, s), 3.91(3H, s), 3.99(3H, s), 4.12(2H, q), 4.89(2H, q), 6.30–6.70(2H, m), 7.20–7.90(5H, m) |
| c-5 | 2.80(2H, t), 2.85(3H, d), 3.94(3H, s), 4.13(2H, q), 4.93(2H, s), 6.40–6.70(2H, s), 7.20–7.90(5H, m) |
| c-7 | 2.88(3H, t), 3.77(3H, s), 3.82(3H, s), 3.97(3H, s), 4.20(2H, t), 5.11(2H, s), 6.45–7.91(7H, m) |

TABLE 14-continued

| Compound No. | 1H-NMR (CDCl$_3$) (ppm) |
|---|---|
| c-8 | 2.83(2H, t), 2.86(3H, d), 3.65(3H, s), 3.92(3H, s), 4.14(2H, t), 5.01(2H, s), 5.93(1H, bs), 6.43–7.82(7H, m) |
| c-11 | 2.79(3H, d), 2.85(2H, t), 3.33(3H, s), 3.93(3H, s), 4.18(2H, t), 4.94(1H, s), 5.24(2H, ABq), 6.49–7.86(8H, m) |
| c-13 | 2.11(3H, s), 2.82(2H, t), 3.69(3H, s), 3.79(3H, s), 3.92(3H, s), 4.19(2H, t), 4.97(2H, s), 6.42(1H, d), 7.20–7.70(6H, m) |
| c-15 | 2.07(3H, s), 2.83(2H, t), 3.82(3H, s), 3.93(3H, s), 4.01(3H, s), 4.19(2H, t), 4.97(2H, s), 6.43(1H, d), 7.20–7.85(5H, m) |
| c-16 | 2.07(3H, s), 2.85(2H, t), 2.87(3H, d), 3.93(3Hx2, s), 4.21(2H, t), 4.97(2H, s), 6.40–6.80(2H, m), 7.21–7.73(5H, m) |
| c-26 | 2.14(3H, s), 2.81(2H, t), 3.80(3H, s), 3.92(3H, s), 4.00(3H, s), 4.11(2H, t), 4.89(2H, s), 6.28(1H, s), 7.20–7.71(5H, m) |
| c-27 | 2.13(3H, s), 2.85(3H, d), 2.86(2H, t), 3.91(3H, s), 3.92(3H, s), 4.13(2H, t), 4.89(2H, s), 6.30(1H, s), 6.70(1H, bs), 7.20–7.60(5H, m) |
| c-29 | 1.09(3H, t), 2.49–2.94(4H, m), 3.83(3H, s), 3.92(3H, s), 4.02(3H, s), 4.29(2H, t), 4.93(2H, s), 6.43(1H, d), 7.20–7.72(5H, m) |
| c-30 | 1.07(3H, t), 2.48–2.95(7H, m), 3.92(3Hx2, s), 4.93(2H, s), 6.39–6.80(2H, m), 7.21–7.72(5H, m) |
| c-43 | 0.96(3H, t), 1.35–1.70(4H, m), 2.83(2H, t), 3.82(3H, s), 4.01(3H, s), 4.15–4.40(4H, m), 4.96(2H, s), 6.45(1H, d), 7.20–7.76(5H, m) |
| c-46 | 1.22(3Hx2, t), 2.17(3H, s), 2.90(2H, t), 3.50–3.89(7H, m), 4.10(3H, s), 4.20(3H, s), 4.75(2H, t), 5.28(2H, s), 6.58(1H, d), 7.25–8.10(5H, m) |
| c-48 | 2.09(3H, s), 2.79(2H, t), 3.84(3H, s), 4.02(3H, s), 4.25(2H, t), 4.76(2H, s), 4.97(2H, s), 6.47(1H, d), 7.22–7.74(5H, m) |
| c-49 | 2.09(3H, s), 2.75–2.95(5H, m), 3.95(3H, s), 4.20(2H, t), 4.76(2H, s), 4.98(2H, s), 6.50(1H, d), 6.70–6.81(1H, m), 7.25–7.76(5H, m) |
| c-52 | 1.31(9H, s), 2.09(3H, s), 2.83(2H, t), 3.80(3H, s), 4.00(3H, s), 4.20(2H, t), 4.94(2H, s), 6.44(1H, d), 7.21–7.79(5H, m) |
| c-53 | 1.30(9H, s), 2.04(3H, s), 2.83(2H, t), 2.85(3H, d), 3.89(3H, s), 4.18(2H, t), 4.92(2H, s), 6.46(1H, d), 7.21–7.78(5H, m) |
| c-58 | 0.95(3H, s), 1.36–1.71(4H, m), 2.08(3H, s), 2.78–2.90(5H, m), 3.91(3H, s), 4.15–4.35(4H, m), 4.95(2H, s), 6.46(1H, d), 7.20–7.76(5H, m) |
| c-61 | 2.10(3H, s), 2.84(2H, t), 3.85(3H, s), 4.05(3H, s), 4.24(2H, t), 4.65(2H, d), 4.95(2H, s), 6.11–6.30(2H, m), 6.47(1H, d), 7.22–7.73(5H, m) |
| c-62 | 2.09(3H, s), 2.76–2.96(5H, m), 3.91(3H, s), 4.22(2H, t), 4.65(2H, d), 4.95(2H, s), 6.11–6.29(2H, m,), 6.45(1H, d), 7.21–7.74(5H, m) 6.60–6.78(1H, m) |
| c-63 | 2.08(3H, s), 2.90(2H, t), 3.82(3H, s), 4.01(3H, s), 4.22(2H, t), 4.92(2H, s), 4.96(2H, s), 6.35(1H, s), 6.50(1H, d), 7.15–7.56(5H, m) |
| c-64 | 2.08(3H, s), 2.70–3.02(5H, m), 3.94(3H, s), 4.20(2H, t), 4.70(2H, s), 4.96(2H, s), 6.35(1H, s), 6.50(1H, d), 6.70–6.89(1H, m), 7.19–7.75(5H, m) |
| c-67 | 1.79(3Hx2, s), 2.09(3H, s), 2.79–2.99(5H, m), 3.94(3H, s), 4.20(2H, t), 4.65(2H, d), 4.96(2H, s), 5.40(1H, t), 6.50(1H, d), 6.70–6.81(1H, m), 7.21–7.76(5H, m) |
| c-78 | 2.08(3H, s), 2.89(2H, t), 3.81(3H, s), 4.00(3H, s), 4.19(2H, t), 4.96(2H, s), 5.08(2H, s), 6.45(1H, d), 7.15–7.70(8H, m) |
| c-79 | 2.07(3H, s), 2.80–3.00(5H, m), 3.92(3H, s), 4.20(2H, t), 4.95(2H, s), 5.09(2H, s), 6.48(1H, d), 6.70–6.80(1H, m), 7.19–7.70(8H, m) |
| c-80 | 2.09(3H, s), 2.81(3H, s), 2.90(2H, t), 4.02(3H, s), 4.25(2H, t), 4.95(2H, s), 5.16(2H, s), 6.44(1H, d), 7.10–7.60(9H, m) |
| c-81 | 2.08(3H, s), 2.74–3.00(5H, m), 3.90(3H, s), 4.19(2H, t), 4.95(2H, s), 5.14(2H, s), 6.46(1H, d), 6.64–6.80(1H, m), 7.00–7.72(9H, m) |
| c-82 | 2.08(3H, s), 2.80(2H, t), 3.82(3H, s), 4.02(3H, s), 4.45(2H, t), 4.95(2H, s), 5.20(2H, s), 6.42(1H, d), 7.16–7.55(5H, m) |
| c-83 | 2.08(3H, s), 2.76–2.99(5H, m), 3.95(3H, s), 4.72(2H, d), 4.97(2H, s), 6.18(1H, t), 6.48(1H, d), 6.63–6.81(1H, m), 7.20–7.79(5H, m) |
| c-86 | (d6-DMS0) 1.95(3H, s), 2.65–2.90(2H, m), 3.71(3H, s), 3.92(3H, s), 4.19(2H, t), 4.92(2H, s), 6.61(1H, d), 7.30–8.15(5H, m) |
| c-87 | (d6-DMS0) 1.98(3H, s), 2.66(3H, d), 2.76(2H, t), 3.84(3H, s), 4.16(2H, t), 4.92(2H, s), 6.56(1H, d), 7.00–8.30(5H, m), 10.84(1H, s) |
| c-88 | 2.09(3H, s), 2.87(2H, t), 3.82(3H, s), 4.02(3H, s), 4.20(2H, t), 4.96(2H, s), 5.62(2H, s), 6.46(1H, d), 7.21–8.34(12H, m) |
| c-89 | 2.06(3H, s), 2.65–2.95(5H, m), 3.91(3H, s), 4.14(2H, t), 4.95(2H, s), 5.61(2H, s), 6.47(1H, d), 6.60–6.75(1H, m), 7.15–8.15(12H, m) |

TABLE 15

| Compound No. | 1H-NMR (CDCl$_3$) (ppm) |
|---|---|
| d-6 | 1.35(3H×2, s), 2.06(3H, s), 2.75(2H, s), 3.79(3H, s), 3.90(3H, s), 4.00(3H, s), 4.94(2H, s), 6.40(1H, d), 7.20–7.70(5H, m) |
| d-7 | 0.80–1.56(11H, m), 2.45–2.70(2H, m), 2.84(2H, t), 2.88(3H, d), 3.94(3H×2, s), 4.13(2H, t), 4.89(2H, s), 6.30(1H, s), 6.70(1H, bs), 7.21–7.60(5H, m) |
| d-8 | 1.44(3H, d), 2.11(3H, s), 3.68(3H, s), 3.78(3H, s), 3.91(3H, s), 4.96(2H, s), 6.42(1H, d), 7.10–7.70(6H, m) |
| d-10 | 1.43(3H, d), 2.09(3H, s), 3.01(2H, d), 3.79(3H, s), 3.91(3H, s), 3.99(3H, s), 4.92(2H, s), 6.41(1H, d), 7.20–7.70(5H, m) |
| d-11 | 1.44(3H, d), 2.08(3H, s), 2.80–3.07(5H, m), 3.92(3H×2, s), 4.93(2H, s), 6.39–6.75(2H, m), 7.18–7.70(5H, m) |

TABLE 16

| Compound No. | 1H-NMR (CDCl$_3$) (ppm) |
|---|---|
| e-5 | 2.80(3H, d), 2.85(4H, bs), 3.91(3H, s), 3.93(3H, s), 4.91(2H, s), 6.70–6.90(2H, m), 7.20–7.70(5H, m) |
| e-15 | 2.14(3H, s), 2.89(2H×2, s), 3.81(3H, s), 3.93(3H, s), 4.02(3H, s), 4.96(2H, s), 6.70(1H, d), 7.21–7.51(5H, m) |
| e-16 | 2.12(3H, s), 2.85(3H, d), 2.89(2H×2, s), 3.92(3H, s), 3.94(3H, s), 4.95(2H, s), 6.74(1H, d), 7.21–7.52(5H, m) |
| e-22 | 2.17(3H, s), 2.48(3H, s), 2.83(2H×2, s), 3.82(3H, s), 3.97(3H, s), 4.03(3H, s), 4.91(2H, s), 6.63(1H, s), 7.20–7.50(4H, m) |
| e-23 | 2.19(3H, s), 2.46(3H, s), 2.83–2.91(7H, m), 3.95(3H, s), 3.99(3H, s), 4.93(2H, s), 6.13(1H, s), 7.20–7.49(4H, m) |
| e-26 | 2.21(3H, s), 2.87(2H×2, s), 3.79(3H, s), 3.92(3H, s), 4.00(3H, s), 4.92(2H, s), 6.62(1H, s), 7.20–7.43(5H, m) |
| e-27 | 2.19(3H, s), 2.83(3H, d), 2.88(2H×2, s), 3.92(3H×2, s), 4.94(2H, s), 6.16(1H, s), 7.21–7.50(5H, m) |
| e-56 | 2.18(3H, s), 2.43(3H, s), 2.81(2H×2, s), 2.85(3H, s), 3.91(3H, s), 4.63(2H, d), 4.91(2H, s), 6.21(1H, t), 6.58–6.86(2H, m), 7.20–7.50(4H, m) |
| e-57 | 2.13(3H, s), 2.89(2H×2, s), 3.81(3H, s), 4.01(3H, s), 4.57(2H, d), 4.96(2H, s), 6.10–6.25(2H, m), 6.70(1H, d), 7.20–7.50(5H, m) |
| e-58 | 2.14(3H, s), 2.88(3H, d), 2.90(2H×2, s), 3.94(3H, s), 4.59(2H, d), 4.96(2H, s), 6.10–6.25(2H, m), 6.60–6.81(2H, m), 7.21–7.50(5H, m) |
| e-59 | 2.19(3H, s), 2.45–2.50(4H, m), 2.80–2.91(7H, m), 3.93(3H, s), 4.26(2H, d), 4.91(2H, s), 6.59–6.75(2H, m), 7.20–7.55(4H, m) |
| e-60 | 2.14(3H, s), 2.44(1H, t), 2.90(2H×2, s), 3.80(3H, s), 4.00(3H, s), 4.71(2H, d), 4.97(2H, s), 6.71(1H, d), 7.20–7.52(5H, m) |
| e-61 | 2.12(3H, s), 2.45(1H, t), 2.86(3H, d), 2.91(2H×2, s), 3.92(3H, s), 4.72(2H, d), 4.96(2H, s), 6.60–6.83(2H, m), 7.21–7.54(5H, m) |

TABLE 17

| Compound No. | 1H-NMR (CDCl$_3$) (ppm) |
|---|---|
| f-4 | 1.25(3H, d), 2.11(3H, s), 2.57–3.55(3H, m), 3.79(3H, s), 3.90(3H, s), 3.99(3H, s), 4.94(2H, s), 6.61–7.79(6H, m) |
| f-5 | 1.20–1.35(3H, m), 2.10(3H, s), 2.85(3H, d), 3.91(3H×2, s), 4.95(2H, s), 6.50–6.90(2H, m), 7.20–7.50(5H, m) |
| f-9 | 1.25(3H, d), 2.21(3H, s), 3.10–3.50(2H, m), 3.81(3H, s), 3.91(3H, s), 4.01(3H, s), 4.93(2H, s), 6.62(1H, s), 7.20–7.50(5H, m) |
| f-10 | 1.26(3H, d), 2.23(3H, s), 3.81(3H, s), 3.94(3H, s), 4.01(3H, s), 4.94(2H, s), 6.63(1H, s), 7.21–8.02(5H, m) |
| f-11 | 1.24(3H, d), 2.20(3H, s), 2.85(3H, d), 3.37(1H, m), 3.91(3H×2, s), 4.93(2H, s), 6.65(1H, s), 7.20–7.45(5H, m) |
| f-12 | 1.27(3H, d), 2.20(3H, s), 2.86(3H, d), 3.94(3H, s), 3.96(3H, s), 4.97.(2H, s), 6.67(1H, s), 7.15–8.05(5H, m) |

TABLE 18

| Compound No. | 1H-NMR (CDCl$_3$) (ppm) |
|---|---|
| g-4 | 1.50–2.02(2H, m), 2.58–2.79(4H, m), 3.82(3H, s), 3.93(3H, s), 4.01(3H, s), 4.92(2H, s), 6.61–7.92(7H, m) |
| g-5 | 1.60–2.01(2H, m), 2.58–2.79(4H, m), 2.87(3H, d), 3.92(3H, s), 3.93(3H, s), 4.92(2H, s), 6.61–7.92(8H, m), |
| g-13 | 1.70–2.05(2H, m), 2.18(3H, s), 2.67(2Hx2, t), 3.67(3H, s), 3.87(3H, s), 3.91(3H, s), 4.95(2H, s), 6.65(1H, d), 6.98–7.84(6H, m) |
| g-15 | 1.70–2.05(2H, m), 2.14(3H, s), 2.68(2Hx2, t), 3.80(3H, s), 3.92(3H, s), 4.00(3H, s), 4.93(2H, s), 6.65(1H, d), 7.20–7.84(5H, m) |
| g-16 | 1.60–2.00(2H, m), 2.10(3H, s), 2.67(2Hx2, t), 2.84(3H, d), 3.91(3Hx2, s), 4.91(2H, s), 6.68(1H, d), 7.20–7.84(5H, m) |
| g-24 | 1.67–2.00(2H, m), 2.23(3H, s), 2.68(2Hx2, m), 3.69(3H, s), 3.78(3H, s), 3.94(3H, s), 4.93(2H, s), 6.45(1H, s), 6.90–7.72(6H, m) |
| g-26 | 1.55–1.99(2H, m), 2.21(3H, s), 2.68(2Hx2, t), 3.81(3H, s), 3.93(3H, s), 4.02(3H, s), 4.92(2H, s), 6.47(1H, s), 7.22–7.72(5H, m) |
| g-27 | 1.10–2.00(2H, m), 2.19(3H, s), 2.67(2Hx2, t), 2.86(3H, d), 3.93(3H, s), 3.95(3H, s), 4.92(2H, s), 6.48(1H, s), 6.67(1H, bs), 7.21–7.70(5H, m) |
| g-58 | 1.70–2.01(2H, m), 2.15(3H, s), 2.67(2Hx2, t), 3.79(3H, s), 4.00(3H, s), 4.57(2H, d), 4.94(2H, s), 6.10–6.25(2H, m), 6.65(1H, d), 7.20–7.81(5H, m) |
| g-59 | 1.58–1.95(2H, m), 2.13(3H, s), 2.68(2Hx2, t), 2.87(3H, d), 3.92(3H, s), 4.59(2H, d), 4.93(2H, s), 6.10–6.25(2H, m), 6.55–6.80(2H, m), 7.20–7.84(5H, m) |
| g-60 | 1.70–2.03(2H, m), 2.15(3H, s), 2.43(1H, t), 2.71(2Hx2, t), 3.81(3H, s), 4.01(3H, s), 4.72(2H, d), 4.93(2H, s), 6.66(1H, d), 7.22–7.86(5H, m) |
| g-61 | 1.60–1.98(2H, m), 2.13(3H, s), 2.42(1H, t), 2.55–2.80(4H, m), 2.86(3H, d), 3.92(3H, s), 4.72(2H, d), 4.93(2H, s), 6.55–6.85(2H, m), 7.20–7.90(5H, m) |

TABLE 19

| Compound No. | 1H-NMR (CDCl$_3$) (ppm) |
|---|---|
| h-1 | 1.09(3H, d), 1.56–2.01(2H, m), 2.18(3H, s), 2.69(2H, m), 3.69(3H, s), 3.89(3H, s), 3.92(3H, s), 4.95(2H, s), 6.66(1H, d), 7.20–7.85(6H, m) |
| h-3 | 1.12(3H, d), 1.70–2.00(2H, m), 2.16(3H, s), 2.60–2.85(3H, m), 3.81(3H, s), 3.92(3H, s), 4.00(3H, s), 4.94(2H, s), 6.66(1H, d), 7.20–7.87(5H, m) |
| h-4 | 1.11(3H, d), 1.62–1.93(2H, m), 2.12(3H, s), 2.70(2H, t), 2.85(3H, d), 3.49(1H, m), 3.91(3Hx2, s), 4.92(2H, s), 6.60–6.89(2H, m), 7.20–7.88(5H, m) |
| h-18 | 1.12(3H, d), 1.60–1.85(2H, m), 2.20(3H, s), 2.62(2H, m), 3.32–3.60(1H, m), 3.80(3H, s), 3.92(3H, s), 4.00(3H, s), 4.91(2H, s), 6.44(1H, s), 7.20–7.73(5H, m) |
| h-19 | 1.11(3H, d), 2.19(3H, s), 2.84(3H, d), 3.90(3H, s), 3.93(3H, s), 4.92(2H, s), 6.48(1H, s), 6.70–7.74(5H, m) |

TABLE 20

| Compound No. | 1H-NMR (CDCl$_3$) (ppm) |
|---|---|
| i-4 | 1.50–2.10(2H, m), 2.60–2.90(4H, m), 3.83(3H, s), 4.01(3H, s), 4.04(3H, s), 4.95(2H, s), 6.60–7.75(7H, m) |
| i-5 | 1.66(1H, bs), 1.80(2H, q), 3.60–3.90(4H, m), 3.92(3H, s), 3.97(3H, s), 4.94(2H, s), 6.60–7.70(7H, m) |

TABLE 21

| Compound No. | 1H-NMR (CDCl$_3$) (ppm) |
|---|---|
| j-4 | 1.54–2.00(2H, m), 2.56–2.80(4H, m), 3.80(3H, s), 3.95(3H, s), 3.99(3H, s), 4.91(2H, s), 6.79–7.75(7H, m), |
| j-5 | 1.55–2.00(2H, m), 2.56–2.77(4H, m), 2.86(3H, d), 3.91(3H, s), 3.96(3H, s), 4.92(2H, s), 6.50–7.76(8H, m) |

TABLE 22

| Compound No. | 1H-NMR (CDCl$_3$) (ppm) |
|---|---|
| k-1 | 1.72–2.10(2H, m), 2.18(3H, s), 2.71–2.92(2H, m), 3.70(3H, s), 3.80(3H, s), 3.95(3H, s), 4.12(2H, t), 4.97(2H, s), 6.51(1H, d), 6.75–7.21(6H, m) |
| k-3 | 1.91(2H, t), 2.12(3H, s), 2.65–2.91(2H, m), 3.81(3H, s), 3.93(3H, s), 4.01(3H, s), 4.11(2H, t), 4.93(2H, s), 6.51(1H, d), 7.19–7.45(5H, m) |
| k-4 | 1.80–2.05(2H, m), 2.11(3H, s), 2.80(2H, t), 2.86(3H, d), 3.92(3H, s), 3.94(3H, s), 4.11(2H, t), 4.92(2H, s), 6.47–6.80(2H, m), 7.19–7.43(5H, m) |
| k-5 | 1.22(3H, s), 2.80–3.02(4H, m), 3.69(3H, s), 3.79(3H, s), 3.96(3H, s), 4.92(2H, s), 6.34(1H, d), 7.20–7.91(6H, m) |
| k-6 | 2.20(3H, s), 2.85–3.01(4H, m), 3.82(3H, s), 3.97(3H, s), 4.03(3H, s), 4.91(2H, s), 6.68(1H, s), 7.22–7.75(5H, m) |
| k-7 | 2.18(3H, s), 2.81–2.95(4H, m), 3.93(3H, s), 3.97(3H, s), 4.90(2H, s), 6.61(1H, s), 7.22–7.73(5H, m) |

TABLE 23

Intermediates

| Compound No. | Properties (Temp.: m.p.) |
|---|---|
| ia-1 | 150° C. (decomposition) |
| ia-2 | 154–156° C. |
| ia-3 | 155° C. (decomposition) |
| ia-4 | 158–160° C. |
| ia-5 | |
| ia-6 | |
| ia-7 | |
| ia-8 | 100–103° C. |
| ia-9 | 144–146° C. |
| ia-10 | |
| ia-11 | |
| ia-12 | 154–157° C. |
| ia-13 | |
| ia-14 | |
| ia-15 | 83–85° C. |
| ia-16 | |
| ia-17 | |
| ia-18 | oily |
| ia-19 | oily |
| ia-20 | |
| ia-21 | 142–144° C. |
| ia-22 | 132–135° C. |
| ia-23 | 164–165° C. |
| ia-24 | 131–133° C. |
| ia-25 | 126–128° C. |
| ia-26 | crystal |
| ia-27 | crystal |
| ia-28 | crystal |
| ia-29 | crystal |
| ia-30 | 152–155° C. |
| ia-31 | crystal |
| ia-32 | 109–112° C. |
| ia-33 | crystal |
| ia-34 | crystal |

The structures of the intermediate compounds of the above-described compounds are as follows:

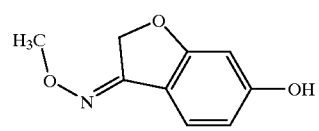
ia-1

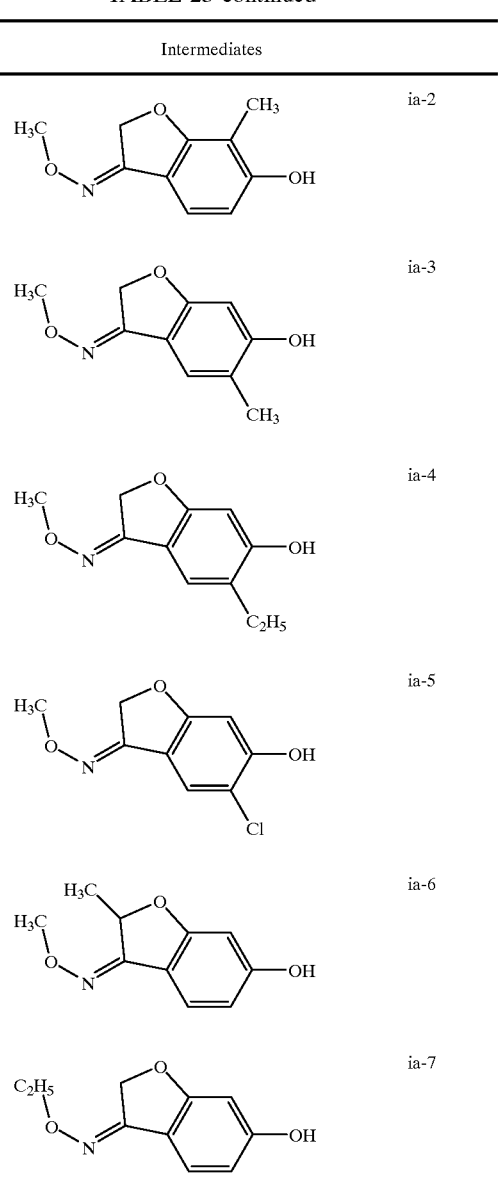

TABLE 23-continued
Intermediates
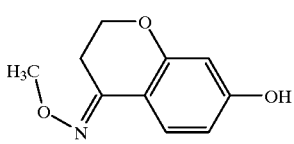 ia-8
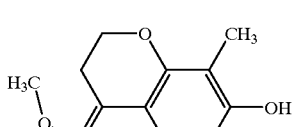 ia-9
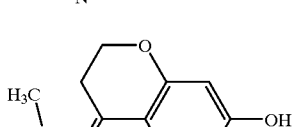 ia-10
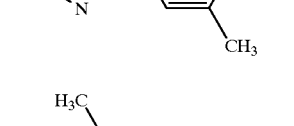 ia-11
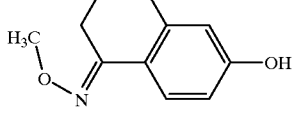 ia-12
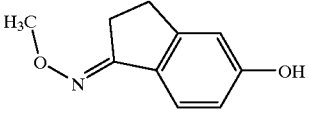 ia-13
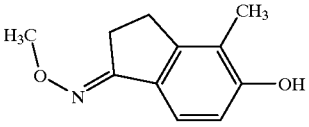 ia-14
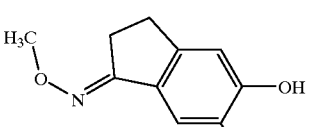 ia-15
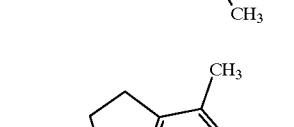 ia-16
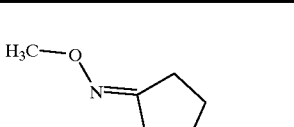 ia-17
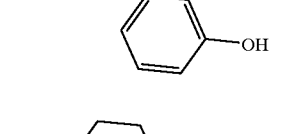 ia-18
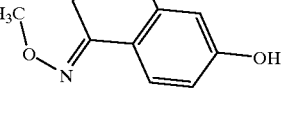 ia-19
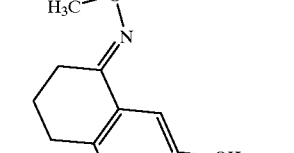 ia-20
 ia-21
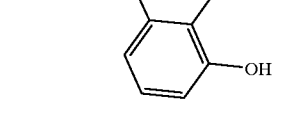 ia-22
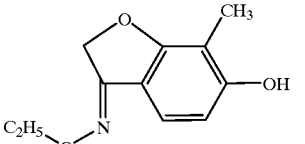 ia-23
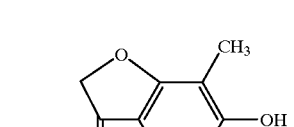 ia-24

TABLE 23-continued

Intermediates

The structures of the intermediate compounds of the above-described compounds are as follows:

Compound
No.  $^1$H-NMR (ppm)

| Compound No. | $^1$H-NMR (ppm) |
|---|---|
| ia-1 | (d$_6$-DMSO): 3.92(3H, s), 5.17(2H, s), 6.48(1H, s), 6.50(1H, d), 7.38(1H, d), 10.18(1H, s) |
| ia-2 | (d$_6$-DMSO): 1.92(3H, s), 3.86(3H, s), 5.09(2H, s), 6.52(1H, d), 7.17(1H, d), 9.94(1H, s) |
| ia-3 | (d$_6$-DMSO): 2.08(3H, s), 3.85(3H, s), 5.06(2H, s), 6.43(1H, s), 7.23(1H, s), 10.10(1H, s) |
| ia-4 | (d$_6$-DMSO): 1.10(3H, t), 2.49(2H, q), 3.83(3H, s), 5.03(2H, s), 6.41(1H, s), 7.20(1H, s), 10.11(1H, s) |
| ia-8 | (d$_6$-DMSO): 2.77(2H, t), 3.86(3H, s), 4.13(2H, t), 6.25–6.52(2H, m), 7.61(1H, d), 9.82(1H, s) |
| ia-9 | (CDCl$_3$ + d$_6$-DMSO): 2.01(3H, s), 2.78(3H, t), 3.89(3H, s), 4.15(2H, t), 6.44(1H, s), 7.54(1H, s), 8.92(1H, s) |
| ia-12 | (CDCl$_3$ + d$_6$-DMSO): 2.88(4H, bs), 6.60–6.85(2H, m), 3.91(1H, s), 7.49(1H, d) |
| ia-13 | (d$_6$-DMSO): 2.05(3H, s), 2.79(2Hx2, s), 3.82(3H, s), 6.47(1H, d), 7.21(1H, d), 9.58(1H, s) |
| ia-15 | (CDCl$_3$ + d$_6$-DMSO): 2.15(3H, s), 2.45(3H, s), 2.80(2Hx2, s), 3.95(3H, s), 6.62(1H, s) |
| ia-18 | (CDCl$_3$): 1.78(2H, q), 2.50–2.80(4H, m), 3.91(3H, s), 6.53–6.70(2H, m), 7.71–7.87(1H, m) |
| ia-19 | (CDCl$_3$): 1.80(2H, q), 2.50–2.80(4H, m), 3.93(3H, s), 6.70–7.20(2H, m), 7.35–7.60(1H, m) |
| ia-21 | (CDCl$_3$ + d$_6$-DMSO): 1.23(3H, t), 2.03(3H, s), 4.16(2H, q), 5.03(2H, s), 6.50(1H, d), 7.20(1H, d), 9.19(1H, s) |
| ia-22 | (CDCl$_3$ + d$_6$-DMSO): 0.93(3H, t), 1.70(2H, m), 2.07(3H, s), 4.06(2H, t), 5.05(2H, s), 6.50(1H, d), 7.20(1H, d), 9.30(1H, s) |
| ia-23 | (CDCl$_3$ + d$_6$-DMSO): 2.03(3H, s), 2.54(1H, t), 4.70(2H, d), 5.08(2H, s), 6.52(1H, d), 7.22(1H, d), 9.31(1H, s) |
| ia-24 | (CDCl$_3$ + d$_6$-DMSO): 2.03(3H, s), 4.56(2H, d), 5.03(2H, s), 6.10–6.30(2H, m), 6.52(1H, d), 7.22(1H, d), 9.30(1H, s) |
| ia-25 | (CDCl$_3$ + d$_6$-DMSO): 2.05(3H, s), 4.10(2H, d), 5.05(2H, s), 5.15–5.40(2H, m), 5.70–6.10(1H, m), 6.50(1H, d), 7.20(1H, d), 9.20(1H, s) |
| ia-26 | (d$_6$-DMSO): 1.60–2.05(2H, m), 2.12(3H, s), 2.68(2Hx2, t), 3.92(3H, s), 6.58(1H, d), 7.73(1H, d) |
| ia-27 | (d$_6$-DMSO): 1.10(3H, d), 1.65–2.00(2H, m), 2.11(3H, s), 2.58–2.85(2H, m), 3.25–3.69(1H, m), 3.92(3H, s), 6.56(1H, d), 7.73(1H, d) |

TABLE 23-continued

Intermediates

| | | |
|---|---|---|
| ia-28 | (d$_6$-DMSO): | 1.55–2.00(2H, m), 2.20(3H, s), 2.55–2.80(4H, m), 3.96(3H, s), 6.48(1H, s), 7.70(1H, s) |
| ia-29 | (d$_6$-DMSO): | 1.13(3H, d), 1.55–2.00(2H, m), 2.19(3H, s), 2.50–2.90(2H, m), 3.30–3.65(1H, m), 3.93(3H, s), 6.47(1H, s), 7.71(1H, s) |
| ia-30 | (d$_6$-DMSO): | 1.75–2.10(2H, m), 2.09(3H, s), 2.78(2H, t), 3.90(3H, s), 4.08(2H, t), 6.53(1H, d), 7.13(1H, d), 8.68(1H, s) |
| ia-31 | (d$_6$-DMSO): | 2.15(3H, s), 2.82–3.00(4H, m), 3.93(3H, s), 5.18(1H, s), 6.53(1H, s), 7.70(1H, s) |
| ia-32 | (d$_6$-DMSO): | 1.35(6H, s), 2.06(3H, s), 2.74(2H, s), 3.91(3H, s), 6.34(1H, d), 7.56(1H, d) |
| ia-33 | (d$_6$-DMSO): | mixture of E and Z 1.27(d), 2.13(s), 2.55–3.48(m), 3.91(s), 3.94(s), 6.67(d), 7.37(d), 8.00(d) |
| ia-34 | (d$_6$-DMSO): | mixture of E and Z 1.23(d), 2.15(s), 2.22(s), 2.51–3.42(m), 3.90(s), 3.90(s), 6.62(s), 7.40(s), 8.03(s) |

TABLE 24

Intermediates

| Compound No. | Q | X | Y | Z | Properties (Temp.: m.p.) |
|---|---|---|---|---|---|
| ib-1 | Q-47 | H | H | Zc | 134–137° C. |
| ib-2 | Q-47 | H | H | Zd | 149–151° C. |
| ib-3 | Q-47 | H | H | Za | |
| ib-4 | Q-47 | H | H | Zb | |
| ib-5 | Q-47 | H | H | Zf | |
| ib-6 | Q-48 | 6-CH$_3$ | H | Zf | |
| ib-7 | Q-48 | H | H | Zg | |
| ib-8 | Q-48 | H | H | Zi | |
| ib-9 | Q-48 | H | H | Zj | |
| ib-10 | Q-49 | H | H | Zc | 109–111° C. |
| ib-11 | Q-50 | H | H | Zd | |
| ib-12 | Q-51 | H | H | Zc | |
| ib-13 | Q-51 | H | H | Za | |
| ib-14 | Q-51 | H | H | Zd | |
| ib-15 | Q-51 | H | H | Zb | |

When Z has a double bond, it is an (E)-isomer.
The structures of groups Q in the above structural formula are as follows:

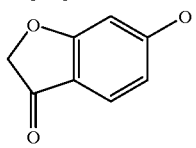

Q-47

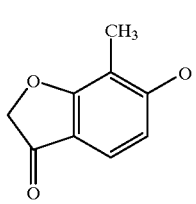

Q-48

TABLE 24-continued

Intermediates

Q-49

Q-50

Q-51

| Compound No. | H-NMR (ppm) | |
|---|---|---|
| ib-1 | (d$_6$-DMSO) | 3.72(3H,s), 3.91(3H,s), 4.72(2H,s), 5.02(2H,s), 6.50–7.58(7H,m) |
| ib-2 | (CDCl$_3$) | 2.85(3H,d), 3.91(3H,s), 4.56(2H,s), 5.03(2H,s), 6.53–7.0(2H,m), 7.2–7.7(5H,m) |
| ib-10 | (CDCl$_3$) | 2.0–3.1(6H,m), 3.82(3H,s), 4.01(3H,s), 4.99(2H,s), 6.9–7.7(7H,m), |
| ib-12 | (CDCl$_3$) | 2.09(3H,s), 2.70(2H,t), 3.81(3H,s), 4.01(3H,s), 4.49(2H,t), 4.99(2H,s), 6.50(1H,d), 7.20–7.78(5H,m) |
| ib-13 | (CDCl$_3$) | 2.11(3H,s), 2.70(2H,t), 3.69(3H,s), 3.80(3H,s), 4.49(2H,t), 5.01(2H,s), 6.49(1H,d), 7.20–7.78(5H,m) |
| ib-14 | (CDCl$_3$) | 2.09(3H,s), 2.60–2.90(2H,m), 2.88(3H,d), 3.92(3H,s), 4.30–4.60(2H,m), 5.00(2H,s), 6.45–6.90(2H,m), 7.22–7.90(5H,m) |

Examples of the preparations containing the derivatives of the present invention as agents for controlling diseases and insect pests are given below, wherein parts are given by weight.

Preparation Example 1

Wettable Powder 50 parts of compound (a-4 or a-8) finely pulverized to a particle diameter of 10 μm with a hammer mill were thoroughly mixed with 3 parts of sodium lignin sulfonate, 2 parts of sodium lauryl sulfate, 10 parts of synthetic silicic acid hydrate and 35 parts of clay by means of a jet mill to obtain a wettable powder in each case.

Preparation Example 2

Emulsifiable Concentrate 10 parts of compound (a-7, 16 or 27) were mixed with 9 parts of polyoxyethylene styrenated phenyl ether, 6 parts of calcium dodecylbenzenesulfonate and 75 parts of xylene to obtain a homogeneous emulsifiable concentrate in each case.

Preparation Example 3

Aqueous Suspension 25 parts of compound (a-5 or 27) finely pulverized to a particle diameter of 5 μm with a hammer mill were mixed with 3 parts of ammonium polyoxyethylene styrenated phenyl ether sulfate, 62 parts of water and a small amount of an antifoaming agent, and the resultant mixture was wet-milled to an average particle size of 2 μm. The mixture thus obtained was mixed with 10 parts of a solution previously prepared from 2 parts of xantham gum, 1 part of an antiseptic, 50 parts of ethylene glycol and 47 parts of water to obtain an aqueous suspension in each case.

Preparation Example 4

Water-dispersible Granule 40 parts of compound (a-5 or 27) finely pulverized to a particle diameter of 5 μm with a hammer mill were mixed with 23 parts of finely pulverized clay, 20 parts of ammonium sulfate powder, 5 parts of sodium lignin sulfonate and 1 part of sodium lauryl sulfate, and the resultant mixture was further pulverized with a jet mill. 15 parts of water were added to the powder to obtain a mixture, which was extruded through a 0.8 mm screen to form grains, which were dried at 70° C. The grains were cut to a length of about 1 to 1.5 mm, and sieved to obtain a water-dispersible granule in each case.

Another preparations were prepared in the same manner as that of Preparation Example 1 except that compound No. 20 disclosed in J. P. KOKAI No. Hei 4-182461 was used.

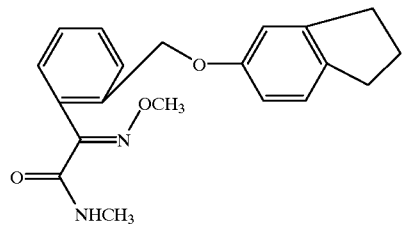

The properties of comparative compound (1) were as follows:

m.p. 121.5~123.5° C.

$^1$H-NMR (CDCl$_3$) (ppm): 2.05 (2H, m), 2.60–3.0 (4H, m), 2.81 (3H, d), 3.88 (3H, s), 4.87 (2H, s), 6.50–7.50 (7H, m)

A preparation was prepared in the same manner as that of above Preparation Example 1 except that compound No. 1.246 in J. P. KOKAI No. Hei 3-17052 was used as comparative compound (2).

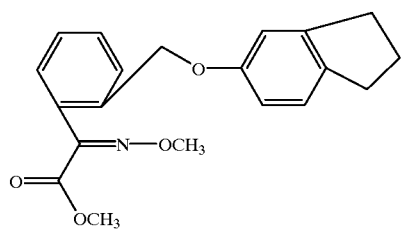

The properties of comparative compound (2) were as follows:

m.p. 80~82° C.

$^1$H-NMR (CDCl$_3$)(ppm): 1.60–1.90(4H, m), 2.50–2.85 (4H, m), 3.80(3H, s), 4.00(3H, s), 4.87(2H, s), 6.52–7.45 (7H, m).

Test Examples confirming the effect of controlling diseases will be given below. The chemical structures of comparative compounds (1) and (2) were utterly different from those of the compounds of the present invention in that the former does not have the alkoxyimino substituent in the bicyclic part. For reference, the experimental data of comparative compounds (1) and (2) are also shown.

Test Example 1

Effects on Barley Powdery Mildew

An emulsion of a compound of the present invention was diluted with water and uniformly sprayed on 5 barley seedlings (variety: Akagi Nijo) in two-leaf stage in each pot having a diameter of 6 cm, with a spray gun. After the natural drying for one day, they were inoculated with *Erysiphe graminis* from which the conidiospore from infected barley were dusted on the test plants, and kept in a greenhouse. Seven days after the inoculation, the numbers of the lesions formed on the leaves were counted, and the preventive rate was calculated according to the following formula (a) to obtain the results shown in Table 25:

Preventive rate (%)=[1-(number of lesions in treated section)/ (number of lesions in untreated section)]×100    (a)

TABLE 25

| Disease to be controlled: Barley powdery mildew | | |
|---|---|---|
| Compound No. | Conc. of active ingredient (ppm) | Preventive rate (%) |
| a-2 | 100 | 100 |
| a-2 | 20 | 79 |
| a-4 | 100 | 100 |
| a-4 | 20 | 93 |
| a-5 | 100 | 100 |
| a-5 | 20 | 95 |
| a-11 | 100 | 100 |
| a-11 | 20 | 88 |
| a-13 | 100 | 100 |
| a-13 | 20 | 100 |
| a-13 | 4 | 100 |
| a-16 | 100 | 100 |
| a-16 | 20 | 100 |
| a-27 | 100 | 100 |
| a-27 | 20 | 100 |
| a-27 | 4 | 100 |
| a-31 | 100 | 100 |
| a-31 | 20 | 99 |
| a-35 | 100 | 100 |
| a-35 | 20 | 100 |
| a-35 | 4 | 98 |
| a-42 | 100 | 100 |

TABLE 25-continued

Disease to be controlled: Barley powdery mildew

| Compound No. | Conc. of active ingredient (ppm) | Preventive rate (%) |
|---|---|---|
| a-42 | 20 | 88 |
| a-59 | 100 | 100 |
| a-59 | 20 | 92 |
| a-60 | 100 | 100 |
| a-60 | 20 | 100 |
| a-61 | 100 | 100 |
| a-61 | 20 | 100 |
| a-61 | 4 | 99 |
| a-62 | 100 | 100 |
| a-62 | 20 | 100 |
| a-62 | 4 | 98 |
| a-63 | 100 | 100 |
| a-63 | 20 | 100 |
| a-63 | 4 | 99 |
| a-64 | 100 | 100 |
| a-64 | 20 | 98 |
| a-64 | 4 | 94 |
| a-70 | 100 | 100 |
| a-70 | 20 | 100 |
| a-71 | 100 | 100 |
| a-71 | 20 | 100 |
| a-73 | 100 | 100 |
| a-73 | 20 | 100 |
| a-73 | 4 | 98 |
| b-4 | 100 | 100 |
| b-4 | 20 | 100 |
| b-4 | 4 | 98 |
| b-5 | 100 | 100 |
| b-5 | 20 | 98 |
| b-5 | 4 | 98 |
| b-6 | 100 | 90 |
| b-6 | 20 | 89 |
| b-7 | 100 | 100 |
| b-7 | 20 | 100 |
| b-7 | 4 | 99 |
| c-2 | 100 | 100 |
| c-2 | 20 | 100 |
| c-13 | 100 | 100 |
| c-13 | 20 | 100 |
| c-13 | 4 | 100 |
| c-15 | 100 | 100 |
| c-15 | 20 | 100 |
| c-15 | 4 | 100 |
| c-16 | 100 | 100 |
| c-16 | 20 | 100 |
| c-16 | 4 | 100 |
| c-27 | 100 | 100 |
| c-27 | 20 | 100 |
| c-27 | 4 | 100 |
| c-29 | 100 | 99 |
| c-29 | 20 | 95 |
| c-30 | 100 | 100 |
| c-30 | 20 | 100 |
| c-30 | 4 | 95 |
| c-58 | 100 | 100 |
| c-58 | 20 | 98 |
| c-62 | 100 | 100 |
| c-62 | 20 | 100 |
| c-62 | 4 | 96 |
| c-64 | 100 | 100 |
| c-64 | 20 | 96 |
| c-67 | 100 | 100 |
| c-67 | 20 | 100 |
| c-79 | 100 | 100 |
| c-79 | 20 | 100 |
| c-81 | 100 | 98 |
| c-81 | 20 | 98 |
| c-82 | 100 | 100 |
| c-82 | 20 | 86 |
| c-83 | 100 | 100 |
| c-83 | 20 | 96 |
| c-89 | 100 | 98 |
| c-89 | 20 | 92 |
| d-8 | 100 | 100 |
| d-8 | 20 | 100 |
| d-8 | 4 | 100 |
| d-11 | 100 | 99 |
| d-11 | 20 | 99 |
| e-5 | 100 | 100 |
| e-5 | 20 | 95 |
| e-16 | 100 | 100 |
| e-16 | 20 | 100 |
| e-16 | 4 | 100 |
| e-23 | 100 | 100 |
| e-23 | 20 | 100 |
| e-23 | 4 | 100 |
| e-26 | 100 | 100 |
| e-26 | 20 | 100 |
| e-27 | 100 | 100 |
| e-27 | 20 | 99 |
| e-27 | 4 | 99 |
| e-58 | 100 | 100 |
| e-58 | 20 | 100 |
| e-61 | 100 | 100 |
| e-61 | 20 | 98 |
| f-5 | 100 | 100 |
| f-5 | 20 | 100 |
| f-5 | 4 | 97 |
| f-11 | 100 | 100 |
| f-11 | 20 | 100 |
| f-11 | 4 | 100 |
| f-12 | 100 | 100 |
| f-12 | 20 | 100 |
| f-12 | 4 | 100 |
| g-5 | 100 | 100 |
| g-5 | 20 | 100 |
| g-5 | 4 | 99 |
| g-13 | 100 | 100 |
| g-13 | 20 | 100 |
| g-13 | 4 | 100 |
| g-16 | 100 | 94 |
| g-16 | 20 | 93 |
| g-24 | 100 | 100 |
| g-24 | 20 | 100 |
| g-24 | 4 | 100 |
| h-1 | 100 | 100 |
| h-1 | 20 | 100 |
| h-1 | 4 | 100 |
| h-4 | 100 | 95 |
| h-4 | 20 | 93 |
| i-4 | 100 | 100 |
| i-4 | 20 | 91 |
| k-1 | 100 | 100 |
| k-1 | 20 | 100 |
| k-1 | 4 | 98 |
| k-4 | 100 | 100 |
| k-4 | 20 | 100 |
| k-4 | 4 | 100 |
| k-5 | 100 | 100 |
| k-5 | 20 | 100 |
| k-5 | 4 | 100 |
| k-7 | 100 | 100 |
| k-7 | 20 | 100 |
| k-7 | 4 | 98 |
| Comp. compd. (1) | 100 | 99 |
| Comp. compd. (1) | 20 | 17 |
| Comp. compd. (2) | 100 | 100 |
| Comp. compd. (2) | 20 | 59 |

Test Example 2

Effect on Wheat Brown Rust

An emulsion of a compound of the present invention was diluted with water and uniformly sprayed on 5 wheat seedlings (variety: Norin No. 61) in two-leaf stage in each pot having a diameter of 6 cm, with a spray gun. After the natural drying for one day, they were inoculated with urediospore suspension of *Puccinia recondita* by the spraying. After leaving them to stand in a high-humidity room at 24° C. for 24 hours, they were kept in a greenhouse. Seven days after the inoculation, the numbers of lesions formed on the leaves were counted, and the preventive rate was calculated according to formula (a) in Test Example 1 to obtain the results shown in Table 26:

TABLE 26

Disease to be controlled: Wheat brown rust

| Compound No. | Conc. of active ingredient (ppm) | Preventive rate (%) |
|---|---|---|
| a-2 | 100 | 100 |
| a-2 | 20 | 100 |
| a-2 | 4 | 98 |
| a-4 | 100 | 98 |
| a-4 | 20 | 94 |
| a-5 | 100 | 100 |
| a-5 | 20 | 100 |
| a-7 | 100 | 100 |
| a-7 | 20 | 99 |
| a-8 | 100 | 100 |
| a-8 | 20 | 99 |
| a-11 | 100 | 100 |
| a-11 | 20 | 88 |
| a-15 | 100 | 100 |
| a-15 | 20 | 96 |
| a-15 | 4 | 96 |
| a-16 | 100 | 100 |
| a-16 | 20 | 100 |
| a-16 | 4 | 100 |
| a-26 | 100 | 100 |
| a-26 | 20 | 100 |
| a-26 | 4 | 100 |
| a-27 | 100 | 100 |
| a-27 | 20 | 100 |
| a-27 | 4 | 98 |
| a-36 | 100 | 100 |
| a-36 | 20 | 100 |
| a-36 | 4 | 100 |
| a-37 | 100 | 100 |
| a-37 | 20 | 99 |
| a-40 | 100 | 100 |
| a-40 | 20 | 97 |
| a-42 | 100 | 100 |
| a-42 | 20 | 100 |
| a-42 | 4 | 100 |
| a-48 | 100 | 100 |
| a-48 | 20 | 100 |
| a-48 | 4 | 100 |
| a-49 | 100 | 100 |
| a-49 | 20 | 100 |
| a-49 | 4 | 100 |
| a-53 | 100 | 100 |
| a-53 | 20 | 98 |
| a-53 | 4 | 98 |
| a-54 | 100 | 100 |
| a-54 | 20 | 100 |
| a-54 | 4 | 100 |
| a-59 | 100 | 100 |
| a-59 | 20 | 98 |
| a-59 | 4 | 90 |
| a-60 | 100 | 100 |
| a-60 | 20 | 100 |
| a-60 | 4 | 100 |
| a-61 | 100 | 100 |
| a-61 | 20 | 100 |
| a-61 | 4 | 91 |
| a-62 | 100 | 100 |
| a-62 | 20 | 100 |
| a-62 | 4 | 100 |
| a-64 | 100 | 100 |
| a-64 | 20 | 100 |
| a-64 | 4 | 100 |
| a-65 | 100 | 100 |
| a-65 | 20 | 100 |
| a-66 | 100 | 100 |

TABLE 26-continued

Disease to be controlled: Wheat brown rust

| Compound No. | Conc. of active ingredient (ppm) | Preventive rate (%) |
|---|---|---|
| a-66 | 20 | 100 |
| a-66 | 4 | 100 |
| a-67 | 100 | 100 |
| a-67 | 20 | 100 |
| a-67 | 4 | 100 |
| a-70 | 100 | 100 |
| a-70 | 20 | 100 |
| a-70 | 4 | 99 |
| a-71 | 100 | 100 |
| a-71 | 20 | 100 |
| a-71 | 4 | 100 |
| a-72 | 100 | 100 |
| a-72 | 20 | 100 |
| a-73 | 100 | 100 |
| a-73 | 20 | 100 |
| a-73 | 4 | 100 |
| a-78 | 100 | 100 |
| a-78 | 20 | 100 |
| a-78 | 4 | 95 |
| a-79 | 100 | 100 |
| a-79 | 20 | 98 |
| a-79 | 4 | 98 |
| b-4 | 100 | 100 |
| b-4 | 20 | 100 |
| b-4 | 4 | 100 |
| b-5 | 100 | 100 |
| b-5 | 20 | 100 |
| b-5 | 4 | 100 |
| b-7 | 100 | 100 |
| b-7 | 20 | 100 |
| b-7 | 4 | 99 |
| c-2 | 100 | 100 |
| c-2 | 20 | 100 |
| c-2 | 4 | 93 |
| c-4 | 100 | 100 |
| c-4 | 20 | 98 |
| c-5 | 100 | 100 |
| c-5 | 20 | 96 |
| c-7 | 100 | 100 |
| c-7 | 20 | 99 |
| c-11 | 100 | 99 |
| c-11 | 20 | 93 |
| c-13 | 100 | 100 |
| c-13 | 20 | 100 |
| c-13 | 4 | 100 |
| c-15 | 100 | 100 |
| c-15 | 20 | 100 |
| c-16 | 100 | 100 |
| c-16 | 20 | 100 |
| c-26 | 100 | 99 |
| c-26 | 20 | 98 |
| c-27 | 100 | 100 |
| c-27 | 20 | 100 |
| c-27 | 4 | 96 |
| c-29 | 100 | 100 |
| c-29 | 20 | 100 |
| c-29 | 4 | 96 |
| c-30 | 100 | 100 |
| c-30 | 20 | 100 |
| c-30 | 4 | 100 |
| c-43 | 100 | 100 |
| c-43 | 20 | 93 |
| c-48 | 100 | 100 |
| c-48 | 20 | 100 |
| c-48 | 4 | 100 |
| c-49 | 100 | 94 |
| c-49 | 20 | 93 |
| c-49 | 4 | 91 |
| c-52 | 100 | 100 |
| c-52 | 20 | 93 |
| c-58 | 100 | 100 |
| c-58 | 20 | 100 |
| c-58 | 4 | 98 |
| c-61 | 100 | 100 |

TABLE 26-continued

Disease to be controlled: Wheat brown rust

| Compound No. | Conc. of active ingredient (ppm) | Preventive rate (%) |
|---|---|---|
| c-61 | 20 | 100 |
| c-61 | 4 | 99 |
| c-62 | 100 | 100 |
| c-62 | 20 | 100 |
| c-62 | 4 | 100 |
| c-63 | 100 | 100 |
| c-63 | 20 | 99 |
| c-64 | 100 | 100 |
| c-64 | 20 | 99 |
| c-64 | 4 | 99 |
| e-67 | 100 | 100 |
| c-67 | 20 | 100 |
| c-67 | 4 | 100 |
| c-78 | 100 | 100 |
| c-78 | 20 | 96 |
| c-79 | 100 | 100 |
| c-79 | 20 | 100 |
| c-79 | 4 | 97 |
| c-80 | 100 | 100 |
| c-80 | 20 | 98 |
| c-81 | 100 | 100 |
| c-81 | 20 | 99 |
| c-81 | 4 | 98 |
| c-82 | 100 | 100 |
| c-82 | 20 | 96 |
| c-83 | 100 | 100 |
| c-83 | 20 | 100 |
| c-83 | 4 | 95 |
| c-89 | 100 | 100 |
| c-89 | 20 | 100 |
| c-89 | 4 | 96 |
| d-6 | 100 | 99 |
| d-6 | 20 | 92 |
| d-8 | 100 | 100 |
| d-8 | 20 | 100 |
| d-8 | 4 | 100 |
| d-11 | 100 | 100 |
| d-11 | 20 | 100 |
| d-11 | 4 | 100 |
| e-5 | 100 | 100 |
| e-5 | 20 | 99 |
| e-15 | 100 | 99 |
| e-15 | 20 | 98 |
| e-16 | 100 | 100 |
| e-16 | 20 | 100 |
| e-23 | 100 | 100 |
| e-23 | 20 | 100 |
| e-26 | 100 | 98 |
| e-26 | 20 | 98 |
| e-27 | 100 | 100 |
| e-27 | 20 | 100 |
| e-27 | 4 | 100 |
| e-58 | 100 | 100 |
| e-58 | 20 | 100 |
| e-61 | 100 | 100 |
| e-61 | 20 | 100 |
| e-61 | 4 | 100 |
| f-5 | 100 | 100 |
| f-5 | 20 | 100 |
| f-5 | 4 | 100 |
| f-11 | 100 | 100 |
| f-11 | 20 | 100 |
| f-11 | 4 | 100 |
| f-12 | 100 | 100 |
| f-12 | 20 | 100 |
| f-12 | 4 | 100 |
| g-5 | 100 | 100 |
| g-5 | 20 | 100 |
| g-5 | 4 | 100 |
| g-13 | 100 | 100 |
| g-13 | 20 | 100 |
| g-13 | 4 | 100 |
| g-15 | 100 | 100 |
| g-15 | 20 | 100 |
| g-15 | 4 | 99 |
| g-16 | 100 | 100 |
| g-16 | 20 | 99 |
| g-24 | 100 | 100 |
| g-24 | 20 | 100 |
| g-24 | 4 | 100 |
| g-58 | 100 | 100 |
| g-58 | 20 | 99 |
| g-58 | 4 | 94 |
| g-59 | 100 | 94 |
| g-59 | 20 | 94 |
| g-60 | 100 | 100 |
| g-60 | 20 | 100 |
| g-60 | 4 | 99 |
| g-61 | 100 | 94 |
| g-61 | 20 | 93 |
| h-1 | 100 | 100 |
| h-1 | 20 | 100 |
| h-1 | 4 | 100 |
| h-3 | 100 | 100 |
| h-3 | 20 | 99 |
| h-3 | 4 | 99 |
| h-4 | 100 | 99 |
| h-4 | 20 | 96 |
| i-4 | 100 | 100 |
| i-4 | 20 | 96 |
| i-5 | 100 | 100 |
| i-5 | 20 | 99 |
| j-4 | 100 | 100 |
| j-4 | 20 | 96 |
| j-5 | 100 | 100 |
| j-5 | 20 | 98 |
| j-5 | 4 | 97 |
| k-1 | 100 | 100 |
| k-1 | 20 | 100 |
| k-1 | 4 | 100 |
| k-3 | 100 | 100 |
| k-3 | 20 | 100 |
| k-3 | 4 | 96 |
| k-4 | 100 | 100 |
| k-4 | 20 | 100 |
| k-4 | 4 | 100 |
| k-5 | 100 | 100 |
| k-5 | 20 | 100 |
| k-5 | 4 | 100 |
| k-7 | 100 | 100 |
| k-7 | 20 | 100 |
| k-7 | 4 | 100 |
| Comp. compd. (1) | 100 | 99 |
| Comp. compd. (1) | 20 | 86 |
| Comp. compd. (2) | 100 | 100 |
| Comp. compd. (2) | 20 | 70 |

Test Example 3

Effect on Tomato Late Blight

An emulsion of a compound of the present invention was diluted with water and uniformly sprayed on a tomato seedling (variety: Ogata-Fukuju) in two-leaf stage in each pot having a diameter of 6 cm, with a spray gun. After the natural drying for one day, they were sprayed with zoospore suspension of *Phytophthora infestans*. They were left to stand in a high-humidity room at 20° C. for 24 hours, and then kept in a greenhouse. Five days after the inoculation, the rate of the area of lesions formed on the leaves was calculated, and the preventive rate was calculated according to the following formula (b) to obtain the results shown in Table 27:

Preventive rate (%)=[1-(area rate of lesions in treated section)/(area rate of lesions in untreated section)]×100    (b)

TABLE 27

Disease to be controlled: Tomato late blight

| Compound No. | Conc. of active ingredient (ppm) | Preventive rate (%) |
|---|---|---|
| a-2 | 100 | 100 |
| a-2 | 20 | 97 |
| a-2 | 4 | 97 |
| a-5 | 100 | 100 |
| a-5 | 20 | 97 |
| a-13 | 100 | 100 |
| a-13 | 20 | 100 |
| a-15 | 100 | 94 |
| a-15 | 20 | 81 |
| a-16 | 100 | 100 |
| a-16 | 20 | 97 |
| a-16 | 4 | 91 |
| a-26 | 100 | 100 |
| a-26 | 20 | 81 |
| a-27 | 100 | 95 |
| a-27 | 20 | 95 |
| a-27 | 4 | 95 |
| a-32 | 100 | 91 |
| a-32 | 20 | 98 |
| a-36 | 100 | 98 |
| a-36 | 20 | 91 |
| a-42 | 100 | 98 |
| a-42 | 20 | 98 |
| a-48 | 100 | 94 |
| a-48 | 20 | 81 |
| a-49 | 100 | 97 |
| a-49 | 20 | 97 |
| a-60 | 100 | 97 |
| a-60 | 20 | 97 |
| a-61 | 100 | 91 |
| a-61 | 20 | 89 |
| a-62 | 100 | 98 |
| a-62 | 20 | 97 |
| a-64 | 100 | 100 |
| a-64 | 20 | 84 |
| a-65 | 100 | 100 |
| a-65 | 20 | 97 |
| a-67 | 100 | 100 |
| a-67 | 20 | 88 |
| a-70 | 100 | 95 |
| a-70 | 20 | 95 |
| b-4 | 100 | 97 |
| b-4 | 20 | 97 |
| b-5 | 100 | 97 |
| b-5 | 20 | 91 |
| b-6 | 100 | 94 |
| b-6 | 20 | 92 |
| b-7 | 100 | 100 |
| b-7 | 20 | 95 |
| c-2 | 100 | 98 |
| c-2 | 20 | 98 |
| c-2 | 4 | 84 |
| c-4 | 100 | 97 |
| c-4 | 20 | 97 |
| c-5 | 100 | 94 |
| c-5 | 20 | 88 |
| c-13 | 100 | 100 |
| c-13 | 20 | 100 |
| c-13 | 4 | 95 |
| c-15 | 100 | 100 |
| c-15 | 20 | 94 |
| c-15 | 4 | 84 |
| c-16 | 100 | 100 |
| c-16 | 20 | 100 |
| c-16 | 4 | 84 |
| c-27 | 100 | 100 |
| c-27 | 20 | 98 |
| c-58 | 100 | 100 |
| c-58 | 20 | 92 |
| c-62 | 100 | 100 |
| c-62 | 20 | 100 |
| e-5 | 100 | 98 |
| e-5 | 20 | 95 |
| e-16 | 100 | 100 |
| e-16 | 20 | 100 |
| e-23 | 100 | 100 |
| e-23 | 20 | 100 |
| e-26 | 100 | 100 |
| e-26 | 20 | 97 |
| e-27 | 100 | 100 |
| e-27 | 20 | 100 |
| e-27 | 4 | 100 |
| e-58 | 100 | 100 |
| e-58 | 20 | 98 |
| e-61 | 100 | 100 |
| e-61 | 20 | 98 |
| f-5 | 100 | 100 |
| f-5 | 20 | 100 |
| f-5 | 4 | 92 |
| f-9 | 100 | 98 |
| f-9 | 20 | 93 |
| f-10 | 100 | 98 |
| f-10 | 20 | 97 |
| f-11 | 100 | 100 |
| f-11 | 20 | 100 |
| f-11 | 4 | 100 |
| f-12 | 100 | 100 |
| f-12 | 20 | 100 |
| f-12 | 4 | 98 |
| g-4 | 100 | 100 |
| g-4 | 20 | 75 |
| g-5 | 100 | 100 |
| g-5 | 20 | 100 |
| g-5 | 4 | 81 |
| g-13 | 100 | 100 |
| g-13 | 20 | 100 |
| g-13 | 4 | 95 |
| g-15 | 100 | 97 |
| g-15 | 20 | 94 |
| g-16 | 100 | 100 |
| g-16 | 20 | 100 |
| g-16 | 4 | 94 |
| g-24 | 100 | 100 |
| g-24 | 20 | 100 |
| g-24 | 4 | 98 |
| g-26 | 100 | 96 |
| g-26 | 20 | 95 |
| g-27 | 100 | 100 |
| g-27 | 20 | 100 |
| g-27 | 4 | 95 |
| g-59 | 100 | 91 |
| g-59 | 20 | 88 |
| g-61 | 100 | 98 |
| g-61 | 20 | 91 |
| h-1 | 100 | 100 |
| h-1 | 20 | 98 |
| h-4 | 100 | 100 |
| h-4 | 20 | 100 |
| k-4 | 100 | 97 |
| k-4 | 20 | 88 |
| k-5 | 100 | 100 |
| k-5 | 20 | 97 |
| Comp. compd. (1) | 100 | 94 |
| Comp. compd. (1) | 20 | 63 |
| Comp. compd. (2) | 100 | 100 |
| Comp. compd. (2) | 20 | 38 |

Test Example 4

Effect on Cucumber Downy Mildew

An emulsion of a compound of the present invention was diluted with water and uniformly sprayed on a cucumber seedling (variety: Sagami Han Shiro Fushi Nari) in 1.5-leaf stage in each pot having a diameter of 6 cm, with a spray gun. After the natural drying for one day, they were sprayed with a zoospore suspension of *Pseudoperonospora cubensis*. They were left to stand in a high-humidity room at 24° C. for 24 hours, and then kept in a greenhouse. Seven days after the inoculation, the rate of the area of lesions formed on the leaves were calculated, and preventive rate was calculated according to formula (b) in Test Example 3 to obtain the results shown in Table 28:

TABLE 28

Disease to be controlled: Cucumber downy mildew

| Compound No. | Conc. of active ingredient (ppm) | Preventive rate (%) |
|---|---|---|
| a-2 | 100 | 100 |
| a-2 | 20 | 100 |
| a-4 | 100 | 94 |
| a-4 | 20 | 94 |
| a-5 | 100 | 94 |
| a-5 | 20 | 88 |
| a-7 | 100 | 97 |
| a-7 | 20 | 94 |
| a-8 | 100 | 94 |
| a-8 | 20 | 88 |
| a-8 | 4 | 75 |
| a-13 | 100 | 100 |
| a-13 | 20 | 96 |
| a-16 | 100 | 100 |
| a-16 | 20 | 100 |
| a-16 | 4 | 100 |
| a-26 | 100 | 100 |
| a-26 | 20 | 100 |
| a-29 | 100 | 97 |
| a-29 | 20 | 97 |
| a-32 | 100 | 97 |
| a-32 | 20 | 81 |
| a-36 | 100 | 100 |
| a-36 | 20 | 100 |
| a-37 | 100 | 100 |
| a-37 | 20 | 100 |
| a-40 | 100 | 100 |
| a-40 | 20 | 97 |
| a-42 | 100 | 100 |
| a-42 | 20 | 100 |
| a-42 | 4 | 100 |
| a-48 | 100 | 100 |
| a-48 | 20 | 100 |
| a-49 | 100 | 100 |
| a-49 | 20 | 100 |
| a-49 | 4 | 88 |
| a-60 | 100 | 100 |
| a-60 | 20 | 100 |
| a-60 | 4 | 100 |
| a-62 | 100 | 100 |
| a-62 | 20 | 100 |
| a-62 | 4 | 94 |
| a-63 | 100 | 100 |
| a-63 | 20 | 100 |
| a-64 | 100 | 100 |
| a-64 | 20 | 100 |
| a-64 | 4 | 100 |
| a-65 | 100 | 100 |
| a-65 | 20 | 94 |
| a-67 | 100 | 100 |
| a-67 | 20 | 100 |
| a-70 | 100 | 91 |
| a-70 | 20 | 88 |
| a-71 | 100 | 100 |
| a-71 | 20 | 100 |
| a-71 | 4 | 100 |
| a-73 | 100 | 88 |
| a-73 | 20 | 88 |
| b-6 | 100 | 100 |
| b-6 | 20 | 100 |
| b-7 | 100 | 96 |
| b-7 | 20 | 93 |
| b-7 | 4 | 89 |
| c-2 | 100 | 100 |
| c-2 | 20 | 97 |
| c-4 | 100 | 100 |
| c-4 | 20 | 94 |

TABLE 28-continued

Disease to be controlled: Cucumber downy mildew

| Compound No. | Conc. of active ingredient (ppm) | Preventive rate (%) |
|---|---|---|
| c-5 | 100 | 100 |
| c-5 | 20 | 100 |
| c-7 | 100 | 100 |
| c-7 | 20 | 94 |
| c-13 | 100 | 100 |
| c-13 | 20 | 100 |
| c-13 | 4 | 100 |
| c-15 | 100 | 100 |
| c-15 | 20 | 100 |
| c-15 | 4 | 81 |
| c-26 | 100 | 100 |
| c-26 | 20 | 100 |
| c-27 | 100 | 96 |
| c-27 | 20 | 93 |
| c-27 | 4 | 86 |
| d-11 | 100 | 100 |
| d-11 | 20 | 96 |
| d-11 | 4 | 93 |
| e-5 | 100 | 100 |
| e-5 | 20 | 100 |
| e-15 | 100 | 100 |
| e-15 | 20 | 95 |
| e-16 | 100 | 100 |
| e-16 | 20 | 100 |
| e-23 | 100 | 100 |
| e-23 | 20 | 96 |
| e-26 | 100 | 100 |
| e-26 | 20 | 100 |
| e-26 | 4 | 75 |
| e-27 | 100 | 100 |
| e-27 | 20 | 100 |
| e-27 | 4 | 100 |
| e-57 | 100 | 100 |
| e-57 | 20 | 94 |
| e-58 | 100 | 100 |
| e-58 | 20 | 100 |
| e-58 | 4 | 100 |
| e-60 | 100 | 100 |
| e-60 | 20 | 88 |
| e-61 | 100 | 100 |
| e-61 | 20 | 100 |
| e-61 | 4 | 100 |
| f-4 | 100 | 100 |
| f-4 | 20 | 100 |
| f-4 | 4 | 100 |
| f-5 | 100 | 100 |
| f-5 | 20 | 100 |
| f-5 | 4 | 99 |
| f-9 | 100 | 100 |
| f-9 | 20 | 100 |
| f-9 | 4 | 100 |
| f-10 | 100 | 100 |
| f-10 | 20 | 100 |
| f-10 | 4 | 100 |
| f-11 | 100 | 100 |
| f-11 | 20 | 100 |
| f-11 | 4 | 100 |
| f-12 | 100 | 100 |
| f-12 | 20 | 100 |
| f-12 | 4 | 100 |
| g-4 | 100 | 100 |
| g-4 | 20 | 100 |
| g-5 | 100 | 100 |
| g-5 | 20 | 100 |
| g-13 | 100 | 100 |
| g-13 | 20 | 100 |
| g-13 | 4 | 100 |
| g-15 | 100 | 100 |
| g-15 | 20 | 94 |
| g-16 | 100 | 100 |
| g-16 | 20 | 100 |
| g-16 | 4 | 100 |
| g-24 | 100 | 100 |
| g-24 | 20 | 100 |

TABLE 28-continued

Disease to be controlled: Cucumber downy mildew

| Compound No. | Conc. of active ingredient (ppm) | Preventive rate (%) |
|---|---|---|
| g-24 | 4 | 100 |
| g-26 | 100 | 100 |
| g-26 | 20 | 100 |
| g-26 | 4 | 100 |
| g-27 | 100 | 100 |
| g-27 | 20 | 100 |
| g-27 | 4 | 96 |
| g-59 | 100 | 100 |
| g-59 | 20 | 100 |
| g-59 | 4 | 100 |
| g-61 | 100 | 100 |
| g-61 | 20 | 100 |
| g-61 | 4 | 100 |
| h-1 | 100 | 100 |
| h-1 | 20 | 100 |
| h-1 | 4 | 100 |
| h-4 | 100 | 100 |
| h-4 | 20 | 100 |
| h-4 | 4 | 100 |
| h-18 | 100 | 100 |
| h-18 | 20 | 100 |
| h-18 | 4 | 96 |
| i-4 | 100 | 94 |
| i-4 | 20 | 88 |
| i-5 | 100 | 100 |
| i-5 | 20 | 100 |
| i-5 | 4 | 100 |
| j-4 | 100 | 100 |
| j-4 | 20 | 100 |
| j-5 | 100 | 100 |
| j-5 | 20 | 100 |
| Comp. compd. (1) | 100 | 81 |
| Comp. compd. (1) | 20 | 30 |
| Comp. compd. (2) | 100 | 93 |
| Comp. compd. (2) | 20 | 70 |

Test Example 5
Effect on Rice Blast

An emulsion of a compound of the present invention was diluted with water and uniformly sprayed on 5 rice plant seedlings (variety: Koshihikari) in 4-leaf stage in each pot having a diameter of 6 cm, with a spray gun. After the natural drying for one day, they were sprayed with conidiospore suspension of *Pyricularia oryzae*. They were left to stand in a high-humidity room at 24° C. for 24 hours, and then kept in a greenhouse. Seven days after the inoculation, the numbers of the lesions formed on the leaves were counted, and the preventive rate was calculated according to formula (a) in Test Example 1 to obtain the results shown in Table 29:

TABLE 29

Disease to be controlled: Rice blast

| Compound No. | Conc. of active ingredient (ppm) | Preventive rate (%) |
|---|---|---|
| a-2 | 100 | 97 |
| a-2 | 20 | 95 |
| a-4 | 100 | 90 |
| a-4 | 20 | 86 |
| a-5 | 100 | 96 |
| a-5 | 20 | 90 |
| a-16 | 100 | 96 |
| a-16 | 20 | 89 |
| a-16 | 4 | 86 |
| a-27 | 100 | 82 |
| a-27 | 20 | 77 |
| a-36 | 100 | 99 |
| a-36 | 20 | 90 |
| a-42 | 100 | 98 |
| a-42 | 20 | 90 |
| a-60 | 100 | 91 |
| a-60 | 20 | 86 |
| a-71 | 100 | 91 |
| a-71 | 20 | 89 |
| b-4 | 100 | 95 |
| b-4 | 20 | 89 |
| b-5 | 100 | 95 |
| b-5 | 20 | 84 |
| b-6 | 100 | 88 |
| b-6 | 20 | 84 |
| b-7 | 100 | 100 |
| b-7 | 20 | 89 |
| c-4 | 100 | 90 |
| c-4 | 20 | 86 |
| c-5 | 100 | 99 |
| c-5 | 20 | 97 |
| c-13 | 100 | 100 |
| c-13 | 20 | 94 |
| c-15 | 100 | 100 |
| c-15 | 20 | 80 |
| c-16 | 100 | 100 |
| c-16 | 20 | 91 |
| c-27 | 100 | 100 |
| c-27 | 20 | 95 |
| c-30 | 100 | 100 |
| c-30 | 20 | 100 |
| c-64 | 100 | 98 |
| c-64 | 20 | 80 |
| d-6 | 100 | 92 |
| d-6 | 20 | 77 |
| d-6 | 4 | 71 |
| d-8 | 100 | 100 |
| d-8 | 20 | 83 |
| d-8 | 4 | 77 |
| d-11 | 100 | 95 |
| d-11 | 20 | 78 |
| d-11 | 4 | 68 |
| e-5 | 100 | 100 |
| e-5 | 20 | 97 |
| f-5 | 100 | 94 |
| f-5 | 20 | 89 |
| f-5 | 4 | 72 |
| f-10 | 100 | 90 |
| f-10 | 20 | 85 |
| f-10 | 4 | 85 |
| f-11 | 100 | 100 |
| f-11 | 20 | 83 |
| f-11 | 4 | 72 |
| f-12 | 100 | 89 |
| f-12 | 20 | 83 |
| f-12 | 4 | 77 |
| g-13 | 100 | 100 |
| g-13 | 20 | 100 |
| g-13 | 4 | 94 |
| g-16 | 100 | 99 |
| g-16 | 20 | 98 |
| g-16 | 4 | 92 |
| g-27 | 100 | 92 |
| g-27 | 20 | 93 |
| g-27 | 4 | 89 |
| g-59 | 100 | 98 |
| g-59 | 20 | 92 |
| g-59 | 4 | 84 |
| g-61 | 100 | 81 |
| g-61 | 20 | 84 |
| g-61 | 4 | 66 |
| h-1 | 100 | 100 |
| h-1 | 20 | 94 |
| h-1 | 4 | 88 |

TABLE 29-continued

Disease to be controlled: Rice blast

| Compound No. | Conc. of active ingredient (ppm) | Preventive rate (%) |
|---|---|---|
| h-4 | 100 | 92 |
| h-4 | 20 | 92 |
| h-4 | 4 | 86 |
| i-4 | 100 | 96 |
| i-4 | 20 | 88 |
| k-1 | 100 | 100 |
| k-1 | 20 | 100 |
| k-4 | 100 | 89 |
| k-4 | 20 | 89 |
| Comp. compd. (1) | 100 | 63 |
| Comp. compd. (1) | 20 | 48 |
| Comp. compd. (2) | 100 | 55 |
| Comp. compd. (2) | 20 | 49 |

Test Example 6

Effect on Rice Brown Spot

An emulsion of a compound of the present invention was diluted with water and uniformly sprayed on 5 rice plant seedlings (variety: Koshihikari) in 4-leaf stage in each pot having a diameter of 6 cm, with a spray gun. After the natural drying for one day, they were sprayed with conidiospore suspension of *Chochliobolus miyabeanus*. They were left to stand in a high-humidity room at 24° C. for 24 hours, and then kept in a greenhouse. Seven days after the inoculation, the numbers of the lesions formed on the leaves were counted, and the preventive rate was calculated according to formula (a) in Test Example 1 to obtain the results shown in Table 30:

TABLE 30

Disease to be controlled: Rice brown spot

| Compound No. | Conc. of active ingredient (ppm) | Preventive rate (%) |
|---|---|---|
| a-2 | 100 | 96 |
| a-2 | 20 | 93 |
| a-4 | 100 | 80 |
| a-4 | 20 | 75 |
| a-5 | 100 | 96 |
| a-5 | 20 | 89 |
| a-13 | 100 | 96 |
| a-13 | 20 | 88 |
| a-16 | 100 | 98 |
| a-16 | 20 | 95 |
| a-16 | 4 | 75 |
| a-27 | 100 | 83 |
| a-27 | 20 | 77 |
| a-36 | 100 | 96 |
| a-36 | 20 | 93 |
| a-36 | 4 | 69 |
| a-42 | 100 | 91 |
| a-42 | 20 | 85 |
| a-61 | 100 | 91 |
| a-61 | 20 | 72 |
| a-61 | 4 | 49 |
| a-62 | 100 | 88 |
| a-62 | 20 | 83 |
| b-6 | 100 | 90 |
| b-6 | 20 | 70 |
| b-7 | 100 | 96 |
| b-7 | 20 | 95 |
| b-7 | 4 | 56 |
| c-4 | 100 | 80 |
| c-4 | 20 | 80 |
| c-5 | 100 | 100 |
| c-5 | 20 | 35 |

TABLE 30-continued

Disease to be controlled: Rice brown spot

| Compound No. | Conc. of active ingredient (ppm) | Preventive rate (%) |
|---|---|---|
| c-13 | 100 | 100 |
| c-13 | 20 | 93 |
| c-13 | 4 | 82 |
| c-15 | 100 | 100 |
| c-15 | 20 | 97 |
| c-15 | 4 | 87 |
| e-5 | 100 | 90 |
| e-5 | 20 | 84 |
| e-23 | 100 | 98 |
| e-23 | 20 | 98 |
| e-26 | 100 | 91 |
| e-26 | 20 | 71 |
| e-27 | 100 | 99 |
| e-27 | 20 | 99 |
| e-27 | 4 | 96 |
| e-61 | 100 | 90 |
| e-61 | 20 | 90 |
| e-61 | 4 | 84 |
| f-4 | 100 | 90 |
| f-4 | 20 | 70 |
| f-4 | 4 | 68 |
| f-5 | 100 | 98 |
| f-5 | 20 | 94 |
| f-5 | 4 | 53 |
| f-12 | 100 | 89 |
| f-12 | 20 | 81 |
| f-12 | 4 | 60 |
| g-13 | 100 | 97 |
| g-13 | 20 | 85 |
| g-13 | 4 | 52 |
| g-15 | 100 | 96 |
| g-15 | 20 | 75 |
| g-15 | 4 | 40 |
| g-16 | 100 | 96 |
| g-16 | 20 | 85 |
| g-16 | 4 | 81 |
| g-27 | 100 | 87 |
| g-27 | 20 | 68 |
| g-27 | 4 | 63 |
| h-4 | 100 | 91 |
| h-4 | 20 | 77 |
| h-4 | 4 | 63 |
| i-4 | 100 | 78 |
| i-4 | 20 | 50 |
| i-5 | 100 | 89 |
| i-5 | 20 | 67 |
| k-1 | 100 | 75 |
| k-1 | 20 | 65 |
| k-1 | 4 | 60 |
| k-4 | 100 | 93 |
| k-4 | 20 | 74 |
| Comp. compd. (1) | 100 | 64 |
| Comp. compd. (1) | 20 | 0 |
| Comp. compd. (2) | 100 | 85 |
| Comp. compd. (2) | 20 | 20 |

Test Example 7

Effect on Rice Sheath Blight

An emulsion of a compound of the present invention prepared in Preparation Example 2 was diluted with water and uniformly sprayed on 5 rice plant seedlings (variety: Koshihikari) in 4.5-leaf stage in each plastic pot having a diameter of 6 cm, with a spray gun. One day after the spraying, the seedlings were bundled at the second sheath with a string. Colonies of *Rhizoctonia solani* previously cultured in PSA culture medium were bored with a cork borer to obtain pieces having a diameter of 4 mm. The piece was put in the bundle, and kept in a high-humidity room at 25° C. until the examination. Ten days after the inoculation, the degree of the disease was examined, and the preventive rate (effect of inhibiting the disease) was calculated on the basis of the following standard:

Severity=B'/A'
   A': Number of leaves used for the test
   B': 100×a+50×b+25×c+12.5×d+6.25×e
      a: Number of leaves in which the lesions were found in at least 50% of the second and third sheaths.
      b: Number of leaves in which the lesions were found in 25–50% of the second and third sheaths.
      c: Number of leaves in which the lesions were found in 12.5–25% of the second and third sheaths.
      d: Number of leaves in which the lesions were found in 6.25–12.5% of the second and third sheaths.
      E: The disease was recognized, and the number of leaves in which the lesions were found in the second and third sheaths was below 6.25%.

Preventive rate=[1−D'/C']×100
   C': Severity in untreated section
   D': Severity in treated section.

The results are shown in Table 31.

TABLE 31

Disease to be controlled: Rice sheath blight:

| Compound No. | Conc. of active ingredient (ppm) | Preventive rate (%) |
|---|---|---|
| a-4 | 100 | 92 |
| a-4 | 20 | 93 |
| a-5 | 100 | 84 |
| a-5 | 20 | 70 |
| a-13 | 100 | 97 |
| a-13 | 20 | 97 |
| a-16 | 100 | 92 |
| a-16 | 20 | 50 |
| a-35 | 100 | 84 |
| a-35 | 20 | 80 |
| a-59 | 100 | 72 |
| a-59 | 20 | 60 |
| a-61 | 100 | 96 |
| a-61 | 20 | 60 |
| a-62 | 100 | 98 |
| a-62 | 20 | 91 |
| a-70 | 100 | 90 |
| a-70 | 20 | 80 |
| b-7 | 100 | 98 |
| b-7 | 20 | 86 |
| c-4 | 100 | 98 |
| c-4 | 20 | 53 |
| c-5 | 100 | 89 |
| c-5 | 20 | 39 |
| c-27 | 100 | 94 |
| c-27 | 20 | 93 |
| c-30 | 100 | 98 |
| c-30 | 20 | 56 |
| c-83 | 100 | 81 |
| c-83 | 20 | 79 |
| d-11 | 100 | 96 |
| d-11 | 20 | 75 |
| e-23 | 100 | 69 |
| e-23 | 20 | 64 |
| g-15 | 100 | 99 |
| g-15 | 20 | 70 |
| g-16 | 100 | 89 |
| g-16 | 20 | 76 |
| g-59 | 100 | 83 |
| g-59 | 20 | 58 |
| g-61 | 100 | 73 |
| g-61 | 20 | 41 |
| h-4 | 100 | 82 |
| h-4 | 20 | 68 |
| i-4 | 100 | 70 |
| i-5 | 100 | 70 |
| Comp. compd. (1) | 100 | 24 |
| Comp. compd. (1) | 20 | 0 |

TABLE 31-continued

Disease to be controlled: Rice sheath blight:

| Compound No. | Conc. of active ingredient (ppm) | Preventive rate (%) |
|---|---|---|
| Comp. compd. (2) | 100 | 0 |
| Comp. compd. (2) | 20 | 0 |

Test Example 8

Effect on Cucumber Gray Mold

An emulsion of a compound of the present invention prepared in Preparation Example 2 was diluted with water and uniformly sprayed on a cucumber seedling (variety: Sagami-Han shiro Fushi nari) in 1.5-leaf stage in each plastic pot having a diameter of 6 cm, with a spray gun. One day after the spraying, the cotyledons were cut out of the seedling, and inoculated with a conidiospore suspension of *Botrytis cinerea* soaked in a paper disc having a diameter of 6 mm, and they were left to stand in a high-humidity room at 25° C. until the examination. Three days after the inoculation, the diameter of each lesion was measured, and severity value was calculated according to the following standard, and the preventive rate was also calculated as follows:

Diameter of developed lesion=E'−F'
   E': diameter of lesion
   F': diameter of paper disc Preventive rate=[1—H'/G']×100
   G': diameter of developed lesion in untreated section
   D': diameter of developed lesion in treated section.

The results are shown in Table 32.

TABLE 32

Disease to be controlled: Cucumber graymold:

| Compound No. | Conc. of active ingredient (ppm) | Preventive rate (%) |
|---|---|---|
| a-7 | 100 | 97 |
| a-7 | 20 | 56 |
| a-11 | 100 | 87 |
| a-11 | 20 | 40 |
| a-13 | 100 | 100 |
| a-13 | 20 | 96 |
| a-15 | 100 | 96 |
| a-15 | 20 | 73 |
| a-16 | 100 | 87 |
| a-16 | 20 | 84 |
| a-16 | 4 | 42 |
| a-26 | 100 | 87 |
| a-26 | 20 | 72 |
| a-37 | 100 | 100 |
| a-37 | 20 | 100 |
| a-40 | 100 | 100 |
| a-40 | 20 | 100 |
| a-59 | 100 | 76 |
| a-59 | 20 | 73 |
| a-61 | 100 | 85 |
| a-61 | 20 | 91 |
| a-62 | 100 | 100 |
| a-62 | 20 | 96 |
| a-63 | 100 | 100 |
| a-63 | 20 | 100 |
| a-70 | 100 | 85 |
| a-70 | 20 | 53 |
| a-71 | 100 | 100 |
| a-71 | 20 | 100 |
| c-13 | 100 | 58 |
| c-13 | 20 | 49 |

TABLE 32-continued

Disease to be controlled: Cucumber graymold:

| Compound No. | Conc. of active ingredient (ppm) | Preventive rate (%) |
|---|---|---|
| c-15 | 100 | 77 |
| c-15 | 20 | 75 |
| c-16 | 100 | 60 |
| c-16 | 20 | 49 |
| e-23 | 100 | 96 |
| e-23 | 20 | 86 |
| Comp. compd. (1) | 100 | 44 |
| Comp. compd. (1) | 20 | 25 |
| Comp. compd. (2) | 100 | 21 |
| Comp. compd. (2) | 20 | 11 |

Test Example 9
Penetration and Translocation

⅔ (tip) of each leaf of five wheat seedlings (variety: Norin No. 61), in 1.5-leaf stage in each pot having a diameter of 6 cm, was covered with an aluminum foil, and the boundary between the covered part and uncovered part was marked. An emulsion of a compound of the present invention was diluted with water and uniformly sprayed thereon with a spray gun. One day after the spraying, the aluminum foil was removed, and the leaves were uniformly inoculated with urediniospore suspension of Puccinia recondita by means of a spray gun, then left to stand in a high-humidity room at 24° C. for 24 hours, and kept in a greenhouse. Seven days after the spraying, the number of lesions formed in the area from the mark to the tip of the leaf was counted, and the preventive rate was calculated according to formula (a) in Test Example 1.

Preventive rate (%) = [1 − (number of lesions in treated section)/(number of lesions in untreated section)] × 100  (a)

Further, the distance from the mark to the lesion closest to the mark (or when no lesion was formed, the distance from the mark to the tip of the leaf) was measured, and a rate of translocation at the perfect preventive concentration was calculated according to the following formula:

Rate of translocation at the perfect preventive concentration (%) = H/Γ×100

H: distance from the mark to the tip
Γ: distance from the mark to the tip
The results are shown in Table 33.

TABLE 33

| Compd. No. | Conc. of active ingredient (ppm) | Number of lesions formed within the mark to the tip | Preventive rate (%) | Rate of the translocation perfect preventive conc. (%) |
|---|---|---|---|---|
| a-5 | 200 | 0 | 100 | 100 |
| a-16 | 200 | 0 | 100 | 100 |
| a-27 | 200 | 0 | 100 | 100 |
| c-5 | 200 | 0 | 100 | 100 |
| e-5 | 200 | 0 | 100 | 100 |
| c-13 | 100 | 0 | 100 | 100 |
| d-10 | 100 | 0 | 100 | 100 |
| e-16 | 100 | 0 | 100 | 100 |
| e-27 | 100 | 0 | 100 | 100 |
| Comp. compd. (1) | 200 | 48 | 23 | 4.4 |
| Mancozeb WP 75% | 930 | 57 | 8 | 1.3 |
| Untreated Zone | — | 62 | — | — |

Test Example 10
Penetration and Translocation

Four points were marked at random on the first leaf of each cucumber seedling (variety: Shogoin aonaga fushinari) in two-leaf stage in each pot having a diameter of 6 cm. 10 μl of the emulsion of a compound of the present invention diluted with water was dropped on each of the marked points on the back of the leaf. The leaf was kept in a greenhouse for one day and then uniformly inoculated with a zoospore suspension of Pseudoperonospora cubenis by means of a spray gun, then left to stand in a high-humidity room at 24° C. for 24 hours, and kept in a greenhouse. The area of the disease-free part 5 days after the spraying was represented in terms of the index.

Index:
 3: At least 40% of the area of the leaf was free from the disease.
 2: 20 to 40% of the area of the leaf was free from the disease.
 1: An area larger than the spot of the drop but smaller than 20% of the area of the leaf was free from the disease.
 0: Only the spot of the drop was free from the disease.
The results are shown in Table 34.

TABLE 34

| Compound No. | Conc. of active ingredient (ppm) | Index |
|---|---|---|
| a-5 | 200 | 3 |
| a-16 | 200 | 3 |
| c-5 | 200 | 3 |
| e-5 | 200 | 3 |
| Comp. compd. (1) | 200 | 0 |
| Mancozeb WP 75% | 930 | 0 |
| Untreated | — | 0 |

Test Examples confirming the effect of controlling insect pests will be given below. For reference, comparative compounds (1) and (2) used in the tests for the effect of controlling diseases did not exhibit the effect of controlling insect pests in the following Test Examples 11 to 15.

Test Example 11
Effect on Tetranychus kanzawai

A piece (3 cm×5 cm) of green bean leaf was placed with the backside up, on a filter paper wet with water so as to prevent the leaf from drying, and inoculated with 10 female imagoes of Tetranychus kanzawai per a leaf. 24 hours after the inoculation, 500 ppm of a compound of the present invention in the form of an emulsion diluted with water was sprayed thereon. After air-drying, the piece was left to stand in a room kept at 26° C. for 24 hours and then the numbers of the living imagoes and dead ones were counted, and the rate of dead imagoes was calculated (repetition: twice). As a result, compound Nos. a-65, a-66, b-4, b-5, b-6, c-13, c-15, c-29, c-58, c-61, c-62, c64, c-78, c-80, c-82, c-83, c-89, d-8, d-10, f-4, f-9, f-10, f-12, g-13, g-24, g-27, g-59, h-1, h-3, h-4, h-18, h-19 and k-5 of the present invention gave a death rate of at least 90%.

Test Example 12

Effect on *Spodoptera litura*

500 ppm of a compound of the present invention in the form of an emulsion diluted with water was sprayed on a leaf of chinese cabbage seedling in 3- to 4-leaf stage. After air-drying, the leaf was placed in a plastic vessel having a size of 21 cm(length)×13 cm(width)×3 cm (depth). Ten larvae of *Spodoptera litura* of the third instar were put therein. The lid was put on the vessel, which was then left in a room kept at 26° C. for 48 hours and then the numbers of the living imagoes and dead ones were counted, and the rate of dead imagoes was calculated (repetition: twice). As a result, compound Nos. a-60, a-65, b-4, b-5, b-7, c-13, c-16, c-27, c-30, c-62, d-8, d-11, e-27, f-4, f-11, f-12, g-24, g-26, g-27, h-1, h-19, k-4 and k-7 of the present invention gave a death rate of at least 90%.

Test Example 13

Effect on *Plutella xylostella*

500 ppm or 50 ppm of a compound of the present invention in the form of an emulsion diluted with water was sprayed on a leaf of Chinese cabbage seedling in 3- to 4-leaf stage. After air-drying, the leaf was placed in a plastic vessel having a size of 9 cm (inner diameter)×6.5 cm (depth). Ten larvae of *Plutella xylostella* of the third instar were put therein. The lid was put on the vessel, which was then left in a room kept at 26° C. for 48 hours and then the numbers of the living imagoes and dead ones were counted, and the rate of dead imagoes was calculated (repetition: twice). As a result, compound Nos. a-62, a-65, b-4, b-5, b-7, c-13, c-15, c-16, c-30, c-62, c-64, c-79, d-8, e-27, f-11, f-12, g-24, g-26, g-27, h-18, h-19 and k-5 of the present invention gave a death rate of at least 90% when the concentration was 500 ppm. Compound Nos. c-13, c-15 and c-16 of the present invention gave a death rate of at least 90% when the concentration was 50 ppm.

Test Example 14

Effect on *Nephotettix cincticeps*

Rice plant seedlings were immersed in 500 ppm or 50 ppm of a compound of the present invention in the form of an emulsion diluted with water for 10 seconds. After air-drying, the root of each seedling was covered with a wet absorbent cotton and the seedling was put in a test tube. Ten larvae of *Nephotettix cincticeps* of the second instar were put therein. The opening of the test tube was covered with a gauze, and the test tube was then left in a room kept at 26° C. for 48 hours and then the numbers of the living imagoes and dead ones were counted, and the rate of dead imagoes was calculated (repetition: twice). As a result, compound Nos. b-4, b-5, c-13, c-15, c-16, c-48, c-58, c-83, d-8, d-10, d-11, f-9, f-10, f-12, g-13, g-24 and h-4 of the present invention gave a death rate of at least 90% when the concentration was 500 ppm. Compound Nos. c-13, c-15, c-16, d-8, d-10 and d-11 of the present invention gave a death rate of at least 90% when the concentration was 50 ppm.

Test Example 15

Effect on *Aphis gossypii*

5 or 6 imagoes of *Aphis gossypii* were released on a cucumber seedling of 1- or 2-leaf stage in a pot. Two days after, the larvae were confirmed and the imagoes were removed. Then 500 ppm or 50 ppm of a compound of the present invention in the form of an emulsion diluted with water was sprayed on the cucumber seedling. After air-drying, the leaves were cut and put in a plastic vessel having a size of 9 cm (inner diameter)×6.5 cm (depth). The lid was put on the vessel, which was then left in a room kept at 26° C. for 48 hours and then the numbers of the living imagoes and dead ones were counted, and the rate of dead imagoes was calculated (repetition: twice). As a result, compound Nos. c-13, c-15 and c-16 of the present invention gave a death rate of at least 90% when the concentration was 500 ppm. Compound Nos. c-13, c-15 and c-16 of the present invention gave a death rate of at least 90% when the concentration was 50 ppm.

It is clear from the above Test Examples that the effects of the agents of the present invention for controlling diseases are superior than those of conventional germicides, in other words, they exhibit excellent effects of controlling diseases or insect pests even at a low concentration.

What is claimed is:

1. An alkoxyimino-substituted bicyclic compound having the following formula (I):

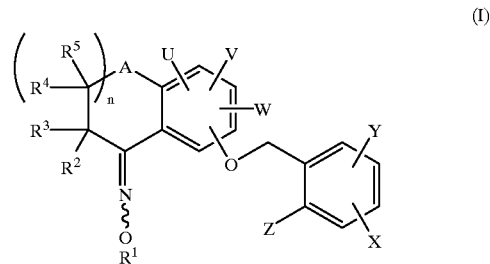

wherein:

R$^1$ represents hydrogen, C1–C6 alkyl, halogenated C1–C6 alkyl, C3–C5 alkenyl, halogenated C3–C5 alkenyl, C3–C5 alkynyl, halogenated C3–C5 alkynyl, cyano-C1–C6 alkyl, C1–C4 alkoxy-C1–C6 alkyl, C1–C4 alkylcarbonyl-C1–C6 alkyl, C1–C4 alkoxycarbonyl-C1–C6 alkyl, C3–C6 cycloalkyl, C3–C6 cycloalkyl-C1–C6 alkyl, phenyl-C1–C6 alkyl, or naphthyl-C1–C6 alkyl;

R$^2$, R$^3$, R$^4$ and R$^5$ each independently represents hydrogen, C1–C3 alkyl or halogenated C1–C3 alkyl;

A represents an oxygen atom;

R$^6$ and R$^7$ each independently represents hydrogen, C1–C3 alkyl or halogenated C1–C3 alkyl;

n represents 0, 1 or 2;

U, V and W each independently represents hydrogen, halogen, C1–C6 alkyl, halogenated C1–C6 alkyl, C1–C6 alkoxy, halogenated C1–C6 alkoxy, cyano or nitro;

X and Y independently represents hydrogen, halogen, C1–C3 alkyl, halogenated C1–C3 alkyl, C1–C3 alkoxy, halogenated C1–C3 alkoxy, cyano or nitro;

Z represents C(CO$_2$CH$_3$)=CHR$^8$, C(CO$_2$CH$_3$) =NOCH$_3$, C(CONHCH$_3$)=NOCH$_3$, C(CSNHCH$_3$) =NOCH$_3$, N(CO$_2$CH$_3$)OCH$_3$, N(CONHCH$_3$)OCH$_3$, N(CSNHCH$_3$)OCH$_3$, CH(CO$_2$CH$_3$)OCH$_3$, CH(CONHCH$_3$)OCH$_3$ or CH(CSNHCH$_3$)COH$_3$; and R$^8$ represents hydrogen, methyl, ethyl or methoxy.

2. The compound of claim 1, wherein Z is $C(CO_2CH_3)=CHOCH_3$, $C(CO_2CH_3)=CHCH_3$, $C(CO_2CH_3)=NOCH_3$ or $C(CONHCH_3)=NOCH_3$.

3. The compound of claim 1, wherein n is 0.

4. The compound of claim 3, wherein:

$R^1$ comprises hydrogen, methyl, ethyl, trifluoroethyl, methoxymethyl, propyl, isopropyl, butyl, hexyl, dimethoxyethyl, diethoxyethyl, difluormoethyl, cyanomethyl, chlorobutyl, tert-butyl, methyl acetyl, trans-chloropropenyl, 2-chloro-propenyl, trans-2-butenyl, dichloropropenyl, methylacetylenyl, benzyl, 4-chlorobenzyl, 4-methoxybenzyl, 4-ethylbenzyl or 4-fluorobenzyl;

U comprises hydrogen or methyl;

V comprises hydrogen, methyl, ethyl, chloro or methoxy;

Z comprises $-C(CO_2CH_3)=(CHOCH_3)$, $-C(CO_2CH_3)=CHCH_3$, $-C(CO_2CH_3)=NOCH_3$, $-C(CONHCH_3)=NOCH_3$, $-C(CSNHCH_3)=NOCH_3$, $-N(CO_2CH_3)OCH_3$, $-N(CONHCH_3)OCH_3$, $-N(CSNHCH_3)OCH_3$, $-CH(CO_2CH_3)OCH_3$, $-CH(CONHCH_3)OCH_3$ or $-CH(CSNHCH_3)OCH_3$.

5. The compound of claim 1, wherein n is 1.

6. The compound of claim 5, wherein:

$R^1$ comprises hydrogen, methyl, ethyl, trifluoroethyl, methoxymethyl, propyl, isopropyl, butyl, hexyl, dimethoxyethyl, diethoxyethyl, difluoroethyl, cyanomethyl, chlorobutyl, tert-butyl, methyl acetyl, trans-chloropropenyl, 2-chloro-propenyl, trans-2-butenyl, dichloropropenyl, methylacetylenyl, benzyl, 4-chlorobenzyl, 4-methoxybenzyl, 4-ethylbenzyl or 4-fluorobenzyl;

U comprises hydrogen or methyl;

V comprises hydrogen, methyl, ethyl, chloro or methoxy;

Z comprises $-C(CO_2CH_3)=(CHOCH_3)$, $-C(CO_2CH_3)=CHCH_3$, $-C(CO_2CH_3)=NOCH_3$, $-C(CONHCH_3)=NOCH_3$, $-C(CSNHCH_3)=NOCH_3$, $-N(CO_2CH_3)OCH_3$, $-N(CONHCH_3)OCH_3$, $-N(CSNHCH_3)OCH_3$, $-CH(CO_2CH_3)OCH_3$, $-CH(CONHCH_3)OCH_3$ or $-CH(CSNHCH_3)OCH_3$.

7. A composition for controlling a plant disease, comprising an alkoxyimino-substituted bicyclic compound of claim 1, as an active ingredient, and a carrier, said composition being in the form of a preparation.

8. The composition of claim 7, wherein the alkoxyimino-substituted bicyclic compound is contained in an amount of 0.1 to 10,000 ppm therein.

9. The composition of claim 7, wherein the alkoxyimino-substituted bicyclic compound is contained in an amount of 1 to 2,000 ppm therein.

10. The composition of claim 7, wherein the preparation is in the form of dust, emulsifiable concentrate, aqueous solution, microcapsule, microemulsion, wettable powder, aqueous or oily suspension, water-dispersible granule or water-soluble powder.

11. The composition of claim 10, wherein the alkoxyimino-substituted bicyclic compound is contained in an amount of 0.002 to 80% by weight therein.

12. A composition for controlling an insect pest, comprising an alkoxyimino-substituted bicyclic compound of claim 1, as an active ingredient, and a carrier, said composition being in the form of a preparation.

13. The composition of claim 12, wherein the alkoxyimino-substituted bicyclic compound is contained in an amount of 0.1 to 10,000 ppm therein.

14. The composition of claim 12, wherein the preparation is in the form of dust, emulsifiable concentrate, aqueous solution, microcapsule, microemulsion, wettable powder, aqueous or oily suspension, water-dispersible granule or water-soluble powder.

15. A method of controlling a plant disease, which comprises the step of applying an effective amount of a compound of claim 1, to a plant or to soil or water containing said plant.

16. The method of claim 15, wherein said compound is applied to water.

17. The method of claim 15, wherein said compound is applied to soil.

18. The method of claim 15, wherein said compound is applied to said plant.

19. The method of claim 18, wherein said compound is applied to stems, leaves, seeds or bulbs of said plant.

20. The method of claim 15, wherein said compound is applied before or while said disease occurs.

21. The method of claim 15, wherein said plant is flowering plant.

22. The method of claim 15, wherein said plant is a fruit tree.

23. The method of claim 15, wherein said plant is a crop plant.

24. The method of claim 15, wherein said plant is a vegetable.

25. The method of claim 15, wherein said plant disease comprises rice blast, rice sheath blight, rice brown spot, wheat eye spot, powdery mildews, oat crown rust, molds, stem rot, downy mildews, scabs, apple blossom blight, peach brown rot, citrus melanose, or citrus penicillium rot.

26. The method of claim 15, wherein said compound is applied to said plant as a composition in a concentration of 0.1 to 10,000 ppm.

27. The method of claim 15, wherein said compound is applied to said soil or water in an amount of about 0.1 to 5,000 g for 10 a. of area.

28. A method of controlling an insect pest, which comprises the step of applying an effective amount of a compound of claim 1, to a plant or to soil or water containing said plant.

29. The method of claim 15, wherein said compound is applied to water.

30. The method of claim 15, wherein said compound is applied to soil.

31. The method of claim 15, wherein said compound is applied to said plant.

32. The method of claim 15, wherein said compound is applied to stems, leaves, seeds or bulbs of said plant.

33. The method of claim 15, wherein said compound is applied before or while said disease occurs.

34. The method of claim 15, wherein said plant is flowering plant.

35. The method of claim 15, wherein said plant is a fruit tree.

36. The method of claim 15, wherein said plant is a crop plant.

37. The method of claim 15, wherein said plant is a vegetable.

38. The method of claim 15, wherein said insect pest comprises beetles, rice water weevils, cabbage army worms, diamond back moth, beet semi-looper, leaf folders, rice borers, plant hoppers, leaf hoppers, while flier, aphids, thrips, mosquitoes, flies, cockroaches, fleas, lice, clothing moths, plant parasitic rematodes, plant parasitic spider mites, shegs, snails or wood lice.

39. The method of claim 15, wherein said compound is applied to said plant as a composition in a concentration of 0.1 to 10,000 ppm.

40. The method of claim 15, wherein said compound is applied to said soil or water is an amount of about 0.1 to 5,000 g for 10 a. of area.

* * * * *